United States Patent
Varughese et al.

(10) Patent No.: US 12,377,711 B2
(45) Date of Patent: Aug. 5, 2025

(54) VEHICLE FEATURE CONTROL SYSTEMS AND METHODS BASED ON SMOKING

(71) Applicant: DENSO International America, Inc., Southfield, MI (US)

(72) Inventors: Sibu Varughese, Sterling Heights, MI (US); Martín Nespolo, Grosse Pointe Woods, MI (US); Thomas Krzyzak, Livonia, MI (US); Gareth Webb, New Hudson, MI (US); Wilson Yim, Troy, MI (US); Matthew Johnson, Royal Oak, MI (US)

(73) Assignee: DENSO International America, Inc., Southfield, MI (US)

( * ) Notice: Subject to any disclaimer, the term of this patent is extended or adjusted under 35 U.S.C. 154(b) by 553 days.

(21) Appl. No.: 17/369,130

(22) Filed: Jul. 7, 2021

(65) Prior Publication Data

US 2022/0055440 A1     Feb. 24, 2022

Related U.S. Application Data

(60) Provisional application No. 63/067,932, filed on Aug. 20, 2020.

(51) Int. Cl.
| | |
|---|---|
| *B60H 1/00* | (2006.01) |
| *B60N 2/56* | (2006.01) |
| *G01N 33/00* | (2006.01) |
| *G06V 20/59* | (2022.01) |

(52) U.S. Cl.
CPC ......... *B60H 1/008* (2013.01); *B60H 1/00878* (2013.01); *B60H 1/00964* (2013.01); *B60N 2/56* (2013.01); *G01N 33/0047* (2013.01); *G06V 20/59* (2022.01)

(58) Field of Classification Search
CPC .......................... B60H 1/008; B60H 1/00878; B60H 1/00964; G06V 20/59; B60N 2/56; G01N 33/0047
See application file for complete search history.

(56) References Cited

U.S. PATENT DOCUMENTS

| | | | |
|---|---|---|---|
| 6,044,826 A | 4/2000 | Bayerle et al. | |
| 6,053,738 A | 4/2000 | Ivey, Jr. | |
| 6,072,398 A | 6/2000 | Hayes et al. | |
| 6,081,195 A | 6/2000 | Lynch | |

(Continued)

FOREIGN PATENT DOCUMENTS

| | | |
|---|---|---|
| CA | 2341894 A1 | 3/2000 |
| CA | 2363251 A1 | 8/2000 |

(Continued)

*Primary Examiner* — Yufeng Zhang
(74) *Attorney, Agent, or Firm* — Harness, Dickey & Pierce, P.L.C.

(57) ABSTRACT

A vehicle system includes: at least one of: a sensor configured to measure an amount of a chemical in air within a passenger cabin of a vehicle; and a camera configured to capture images within the passenger cabin of the vehicle; and a control module configured to: detect smoking within the passenger cabin based on the at least one of the amount of the chemical and at least one of the images; and in response to smoking being detected within the passenger cabin, adjust operation of at least one of a luxury feature of the vehicle and a comfort feature of the vehicle.

17 Claims, 3 Drawing Sheets

(56) References Cited

U.S. PATENT DOCUMENTS

| | | |
|---|---|---|
| 6,082,415 A | 7/2000 | Rowland et al. |
| 6,089,016 A | 7/2000 | Takaku |
| 6,097,288 A | 8/2000 | Koeppe, Jr. |
| 6,118,386 A | 9/2000 | Yousif |
| 6,138,655 A | 10/2000 | Kerns et al. |
| 6,144,310 A | 11/2000 | Morris |
| 6,145,305 A | 11/2000 | Itou et al. |
| 6,160,487 A | 12/2000 | DeLuca |
| 6,166,647 A | 12/2000 | Wong |
| 6,167,695 B1 | 1/2001 | Itou et al. |
| 6,181,250 B1 | 1/2001 | Brooks, Jr. |
| 6,182,497 B1 | 2/2001 | Krajci |
| 6,196,527 B1 | 3/2001 | Huang |
| 6,208,256 B1 | 3/2001 | Fleming et al. |
| 6,215,407 B1 | 4/2001 | Winther |
| 6,216,448 B1 | 4/2001 | Schnaibel et al. |
| 6,216,450 B1 | 4/2001 | Takahashi et al. |
| 6,220,229 B1 | 4/2001 | Kawamura et al. |
| 6,226,982 B1 | 5/2001 | Poggio et al. |
| 6,233,923 B1 | 5/2001 | Itou et al. |
| 6,237,397 B1 | 5/2001 | Shinar et al. |
| 6,240,908 B1 | 6/2001 | Hyodo et al. |
| 6,245,205 B1 | 6/2001 | Schnaibel et al. |
| 6,266,955 B1 | 7/2001 | Liang et al. |
| 6,272,938 B1 | 8/2001 | Baghel et al. |
| 6,281,797 B1 | 8/2001 | Forster et al. |
| 6,282,940 B1 | 9/2001 | Hung et al. |
| 6,287,519 B1 | 9/2001 | Nordman et al. |
| 6,288,643 B1 | 9/2001 | Lerg et al. |
| 6,290,829 B1 | 9/2001 | Kato et al. |
| 6,293,093 B1 | 9/2001 | Goralski et al. |
| 6,293,120 B1 | 9/2001 | Hashimoto |
| 6,294,075 B1 | 9/2001 | Poggio et al. |
| 6,301,881 B1 | 10/2001 | Kumar |
| 6,314,790 B1 | 11/2001 | Sagisaka et al. |
| 6,317,041 B1 | 11/2001 | Singer et al. |
| 6,320,388 B1 | 11/2001 | Sun et al. |
| 6,330,795 B1 | 12/2001 | Takaku et al. |
| 6,338,326 B1 | 1/2002 | Ebeling et al. |
| 6,338,977 B1 | 1/2002 | Kunugi et al. |
| 6,339,379 B1 | 1/2002 | Argus et al. |
| 6,340,447 B2 | 1/2002 | Johnson |
| 6,348,871 B1 | 2/2002 | Tanguay et al. |
| 6,353,386 B1 | 3/2002 | Castonguay et al. |
| 6,357,223 B1 | 3/2002 | Caren et al. |
| 6,357,224 B1 | 3/2002 | Kawamoto et al. |
| 6,357,726 B1 | 3/2002 | Watkins |
| 6,359,567 B1 | 3/2002 | Park |
| 6,363,713 B1 | 4/2002 | Wu et al. |
| 6,363,771 B1 | 4/2002 | Liang et al. |
| 6,374,662 B1 | 4/2002 | Oda et al. |
| 6,376,254 B1 | 4/2002 | Bather et al. |
| 6,378,298 B2 | 4/2002 | Harima et al. |
| 6,378,359 B1 | 4/2002 | Dobson et al. |
| 6,382,017 B1 | 5/2002 | Majkowski et al. |
| 6,386,246 B2 | 5/2002 | Pope et al. |
| 6,386,969 B1 | 5/2002 | O'Brien |
| 6,408,616 B1 | 6/2002 | Mazur et al. |
| 6,410,249 B1 | 6/2002 | Ngai et al. |
| 6,411,207 B2 | 6/2002 | Shaffer |
| 6,411,905 B1 | 6/2002 | Guoliang et al. |
| 6,416,479 B1 | 7/2002 | Seidman |
| 6,418,780 B1 | 7/2002 | Chon |
| 6,418,983 B1 | 7/2002 | Payne et al. |
| 6,420,973 B2 | 7/2002 | Acevedo |
| 6,422,226 B2 | 7/2002 | Niki et al. |
| 6,425,242 B2 | 7/2002 | Booth et al. |
| 6,425,384 B1 | 7/2002 | Howarth et al. |
| 6,429,019 B1 | 8/2002 | Goldstein et al. |
| 6,432,692 B1 | 8/2002 | Bradfield et al. |
| 6,433,696 B1 | 8/2002 | Deiterman et al. |
| 6,435,164 B1 | 8/2002 | Kaiser et al. |
| 6,436,712 B1 | 8/2002 | Yurgil et al. |
| 6,439,026 B2 | 8/2002 | Nakano et al. |
| 6,443,908 B2 | 9/2002 | Stone |
| 6,447,731 B1 | 9/2002 | Sun et al. |
| 6,448,888 B1 | 9/2002 | Horner et al. |
| 6,451,210 B1 | 9/2002 | Sivavec et al. |
| 6,452,510 B1 | 9/2002 | Zysko |
| 6,463,735 B2 | 10/2002 | Morinaga et al. |
| 6,463,967 B1 | 10/2002 | Boyle |
| 6,464,144 B1 | 10/2002 | Swartz et al. |
| 6,467,254 B1 | 10/2002 | Cullen et al. |
| 6,467,332 B1 | 10/2002 | Bertschi et al. |
| 6,471,193 B2 | 10/2002 | Cole Warren |
| 6,474,138 B1 | 11/2002 | Chang et al. |
| 6,484,559 B2 | 11/2002 | Dodabalapur et al. |
| 6,484,951 B1 | 11/2002 | Mueller |
| 6,485,688 B1 | 11/2002 | Sivavec et al. |
| 6,491,828 B1 | 12/2002 | Sivavec et al. |
| 6,492,907 B1 | 12/2002 | McCracken |
| 6,493,638 B1 | 12/2002 | McLean et al. |
| 6,494,077 B2 | 12/2002 | Aoyama et al. |
| 6,495,375 B2 | 12/2002 | Ledig |
| 6,497,092 B1 | 12/2002 | Theis |
| 6,497,227 B2 | 12/2002 | Wang et al. |
| 6,499,291 B2 | 12/2002 | Lang et al. |
| 6,499,516 B2 | 12/2002 | Pope et al. |
| 6,502,386 B1 | 1/2003 | Mazur et al. |
| 6,508,111 B2 | 1/2003 | Osaki et al. |
| 6,515,749 B2 | 2/2003 | Pipino |
| 6,518,878 B1 | 2/2003 | Skoff |
| 6,522,248 B1 | 2/2003 | Andres et al. |
| 6,525,662 B1 | 2/2003 | Ford |
| 6,528,191 B1 | 3/2003 | Senner |
| 6,529,808 B1 | 3/2003 | Diem |
| 6,532,734 B1 | 3/2003 | Nader et al. |
| 6,534,319 B1 | 3/2003 | Liu |
| 6,539,705 B2 | 4/2003 | Beer et al. |
| 6,539,707 B2 | 4/2003 | Ikemoto et al. |
| 6,541,052 B1 | 4/2003 | Rohleder |
| 6,544,971 B1 | 4/2003 | Berliner et al. |
| 6,545,608 B1 | 4/2003 | Kaufman |
| 6,550,310 B1 | 4/2003 | Liu et al. |
| 6,550,318 B2 | 4/2003 | Isobe et al. |
| 6,552,647 B1 | 4/2003 | Thiessen et al. |
| 6,562,208 B2 | 5/2003 | Slater et al. |
| 6,563,318 B2 | 5/2003 | Kawakami et al. |
| 6,564,154 B1 | 5/2003 | Zimmerman et al. |
| 6,564,543 B1 | 5/2003 | Orzel et al. |
| 6,571,550 B2 | 6/2003 | Rosel et al. |
| 6,575,013 B2 | 6/2003 | Bao et al. |
| 6,576,911 B1 | 6/2003 | Potyrailo et al. |
| 6,578,406 B2 | 6/2003 | Kunugi et al. |
| 6,578,715 B2 | 6/2003 | Scranton, Jr. et al. |
| 6,583,720 B1 | 6/2003 | Quigley |
| 6,588,251 B2 | 7/2003 | Zhang et al. |
| 6,589,476 B1 | 7/2003 | Fencl |
| 6,590,710 B2 | 7/2003 | Hara et al. |
| 6,594,562 B2 | 7/2003 | Kaiser et al. |
| 6,595,037 B2 | 7/2003 | McGinley |
| 6,596,236 B2 | 7/2003 | DiMeo, Jr. et al. |
| 6,598,468 B2 | 7/2003 | Zur Loye et al. |
| 6,598,470 B2 | 7/2003 | Ludwig et al. |
| 6,600,417 B2 | 7/2003 | Lerg et al. |
| 6,600,424 B1 | 7/2003 | Morris |
| 6,604,007 B2 | 8/2003 | Leven et al. |
| 6,604,405 B2 | 8/2003 | Whynall et al. |
| 6,606,566 B1 | 8/2003 | Sunshine |
| 6,607,700 B1 | 8/2003 | Apte et al. |
| 6,609,416 B2 | 8/2003 | Brock |
| 6,611,204 B2 | 8/2003 | Schmurr |
| 6,617,166 B2 | 9/2003 | White Gray |
| 6,619,107 B1 | 9/2003 | Tsukamoto et al. |
| 6,623,619 B2 | 9/2003 | Saffell et al. |
| 6,623,973 B2 | 9/2003 | Levitsky et al. |
| 6,631,333 B1 | 10/2003 | Lewis et al. |
| 6,631,611 B2 | 10/2003 | Shi et al. |
| 6,632,268 B2 | 10/2003 | Seeley |
| 6,637,191 B1 | 10/2003 | Ziemba et al. |
| 6,640,608 B2 | 11/2003 | Pepper et al. |
| 6,640,620 B2 | 11/2003 | Cook et al. |
| 6,645,772 B1 | 11/2003 | Kirby et al. |
| 6,646,444 B2 | 11/2003 | Dolgov et al. |

(56) References Cited

U.S. PATENT DOCUMENTS

| | | |
|---|---|---|
| 6,651,422 B1 | 11/2003 | LeGare |
| 6,658,841 B2 | 12/2003 | Beer et al. |
| 6,659,095 B2 | 12/2003 | Kotwicki et al. |
| 6,661,299 B2 | 12/2003 | Dodabalapur et al. |
| 6,666,068 B2 | 12/2003 | Boyd et al. |
| 6,666,201 B1 | 12/2003 | Mazur |
| 6,668,616 B1 | 12/2003 | Shoji et al. |
| 6,672,164 B1 | 1/2004 | Haanstra et al. |
| 6,679,238 B2 | 1/2004 | Nebiyeloul-Kifle et al. |
| 6,682,638 B1 | 1/2004 | Prohaska et al. |
| 6,684,628 B2 | 2/2004 | Gobel et al. |
| 6,684,852 B2 | 2/2004 | Wright et al. |
| 6,685,955 B2 | 2/2004 | Johnson |
| 6,687,601 B2 | 2/2004 | Bale et al. |
| 6,689,322 B2 | 2/2004 | Mills et al. |
| 6,691,023 B2 | 2/2004 | Fujino et al. |
| 6,691,554 B2 | 2/2004 | Eastman et al. |
| 6,693,535 B2 | 2/2004 | Van Bosch et al. |
| 6,694,726 B2 | 2/2004 | Sakai |
| 6,696,296 B2 | 2/2004 | Li et al. |
| 6,698,187 B2 | 3/2004 | Nishioka et al. |
| 6,701,245 B2 | 3/2004 | Birkner et al. |
| 6,701,706 B2 | 3/2004 | Bruck et al. |
| 6,701,707 B1 | 3/2004 | Upadhyay et al. |
| 6,711,470 B1 | 3/2004 | Hartenstein et al. |
| 6,711,932 B2 | 3/2004 | Iwazaki et al. |
| 6,712,101 B1 | 3/2004 | Nanaji |
| 6,712,287 B1 | 3/2004 | Le Pesant et al. |
| 6,712,770 B2 | 3/2004 | Lin et al. |
| 6,713,020 B2 | 3/2004 | Kato et al. |
| 6,716,406 B2 | 4/2004 | Reisfeld et al. |
| 6,732,031 B1 | 5/2004 | Lightner et al. |
| 6,736,120 B2 | 5/2004 | Surnilla |
| 6,736,121 B2 | 5/2004 | Gopichandra |
| 6,739,122 B2 | 5/2004 | Kitajima et al. |
| 6,739,176 B2 | 5/2004 | Neuhausen et al. |
| 6,739,177 B2 | 5/2004 | Sato et al. |
| 6,739,310 B2 | 5/2004 | Esteghlal et al. |
| 6,740,433 B2 | 5/2004 | Senner |
| 6,741,174 B2 | 5/2004 | Rhoades et al. |
| 6,741,181 B2 | 5/2004 | Skaggs |
| 6,744,373 B2 | 6/2004 | Koyano et al. |
| 6,744,503 B2 | 6/2004 | Vo-Dinh et al. |
| 6,745,747 B2 | 6/2004 | Surnilla |
| 6,753,786 B1 | 6/2004 | Apperson et al. |
| 6,754,366 B2 | 6/2004 | Sansone |
| 6,758,185 B2 | 7/2004 | Surnilla et al. |
| 6,761,023 B1 | 7/2004 | Schnaibel et al. |
| 6,763,708 B2 | 7/2004 | Ting et al. |
| 6,765,490 B2 | 7/2004 | Lopez et al. |
| 6,768,420 B2 | 7/2004 | McCarthy et al. |
| 6,770,873 B2 | 8/2004 | Pusterla et al. |
| 6,771,181 B1 | 8/2004 | Hughen, Jr. |
| 6,772,585 B2 | 8/2004 | Iihoshi et al. |
| 6,774,802 B2 | 8/2004 | Bachinski et al. |
| 6,775,602 B2 | 8/2004 | Gordon, Jr. et al. |
| 6,778,082 B2 | 8/2004 | Goodwin |
| 6,778,086 B2 | 8/2004 | Morrone et al. |
| 6,781,696 B1 | 8/2004 | Rosenberger et al. |
| 6,784,798 B2 | 8/2004 | Morris |
| 6,785,605 B2 | 8/2004 | Huller et al. |
| 6,788,197 B1 | 9/2004 | Thuillard et al. |
| 6,791,453 B1 | 9/2004 | Andres et al. |
| 6,792,339 B2 | 9/2004 | Basson et al. |
| 6,792,346 B2 | 9/2004 | Takebayashi et al. |
| 6,792,767 B1 | 9/2004 | Pargeter et al. |
| 6,793,881 B2 | 9/2004 | Himes |
| 6,801,132 B2 | 10/2004 | Clauss et al. |
| 6,803,236 B2 | 10/2004 | Bailey et al. |
| 6,804,951 B2 | 10/2004 | Nader et al. |
| 6,807,806 B2 | 10/2004 | Takaku et al. |
| 6,810,659 B1 | 11/2004 | Bidner et al. |
| 6,816,069 B2 | 11/2004 | Quigley |
| 6,817,225 B2 | 11/2004 | Boyd et al. |
| 6,819,257 B2 | 11/2004 | Swieboda et al. |
| 6,820,012 B2 | 11/2004 | Sunshine |
| 6,822,096 B2 | 11/2004 | Kato |
| 6,822,215 B2 | 11/2004 | Hensel |
| 6,822,555 B2 | 11/2004 | Mansfield, Jr. et al. |
| 6,824,513 B2 | 11/2004 | Jansen |
| 6,827,903 B2 | 12/2004 | Guerra |
| 6,828,156 B2 | 12/2004 | Ohsuga et al. |
| 6,830,027 B1 | 12/2004 | Segawa et al. |
| 6,830,043 B2 | 12/2004 | Morinaga et al. |
| 6,831,471 B2 | 12/2004 | Gertiser et al. |
| 6,834,497 B2 | 12/2004 | Miyoshi et al. |
| 6,834,530 B2 | 12/2004 | Kita et al. |
| 6,836,210 B2 | 12/2004 | Tanguay |
| 6,836,722 B2 | 12/2004 | Yook |
| 6,837,987 B1 | 1/2005 | King |
| 6,838,067 B2 | 1/2005 | Salisbury et al. |
| 6,843,240 B1 | 1/2005 | Hahn et al. |
| 6,843,835 B2 | 1/2005 | Fornai et al. |
| 6,848,418 B1 | 2/2005 | Summers et al. |
| 6,848,439 B2 | 2/2005 | Ohkuma |
| 6,850,172 B2 | 2/2005 | Becka |
| 6,860,100 B1 | 3/2005 | Bidner et al. |
| 6,862,535 B2 | 3/2005 | Binder |
| 6,873,254 B2 | 3/2005 | Andres et al. |
| 6,873,764 B2 | 3/2005 | Maisenholder et al. |
| 6,874,490 B2 | 4/2005 | Surnilla |
| 6,877,498 B1 | 4/2005 | Matsushima et al. |
| 6,879,894 B1 | 4/2005 | Lightner et al. |
| 6,879,936 B2 | 4/2005 | Dilger |
| 6,880,380 B2 | 4/2005 | Nagashima et al. |
| 6,881,382 B2 | 4/2005 | Goldstein et al. |
| 6,882,927 B2 | 4/2005 | Suzuki |
| 6,882,928 B2 | 4/2005 | Yurgil |
| 6,885,279 B2 | 4/2005 | Tseung et al. |
| 6,887,069 B1 | 5/2005 | Thornton et al. |
| 6,891,470 B2 | 5/2005 | Bohinc, Jr. |
| 6,893,632 B2 | 5/2005 | Johnson |
| 6,896,781 B1 | 5/2005 | Shen et al. |
| 6,898,927 B2 | 5/2005 | Morinaga et al. |
| 6,901,741 B2 | 6/2005 | Kobayashi et al. |
| 6,902,701 B1 | 6/2005 | Hughes et al. |
| 6,912,840 B2 | 7/2005 | Posselt et al. |
| 6,912,924 B2 | 7/2005 | Loomis et al. |
| 6,915,203 B2 | 7/2005 | Maegawa et al. |
| 6,920,282 B2 | 7/2005 | He et al. |
| 6,921,604 B2 | 7/2005 | Kato et al. |
| 6,922,149 B1 | 7/2005 | Ford |
| 6,922,639 B2 | 7/2005 | Kawase et al. |
| 6,925,796 B2 | 8/2005 | Nieuwstadt et al. |
| 6,926,601 B2 | 8/2005 | Aoki et al. |
| 6,928,348 B1 | 8/2005 | Lightner et al. |
| 6,930,586 B2 | 8/2005 | Tseung et al. |
| 6,933,151 B2 | 8/2005 | Bailey et al. |
| 6,933,491 B2 | 8/2005 | Maida, Jr. |
| 6,936,147 B2 | 8/2005 | Prohaska et al. |
| 6,938,832 B2 | 9/2005 | Sada |
| 6,940,410 B2 | 9/2005 | Deacy |
| 6,940,411 B2 | 9/2005 | Smith et al. |
| 6,941,193 B2 | 9/2005 | Frecska et al. |
| 6,947,132 B1 | 9/2005 | Boss et al. |
| 6,947,817 B2 | 9/2005 | Diem |
| 6,948,352 B2 | 9/2005 | Rabbett et al. |
| 6,952,945 B2 | 10/2005 | O'Brien |
| 6,957,562 B2 | 10/2005 | Anilovich et al. |
| 6,958,689 B2 | 10/2005 | Anderson et al. |
| 6,961,653 B2 | 11/2005 | Maki |
| 6,962,082 B2 | 11/2005 | Hashimoto et al. |
| 6,964,742 B2 | 11/2005 | Myers |
| 6,965,314 B2 | 11/2005 | Bohinc, Jr. |
| 6,965,344 B1 | 11/2005 | Halsey et al. |
| 6,968,677 B2 | 11/2005 | Tamura |
| 6,968,833 B2 | 11/2005 | Yu et al. |
| 6,975,944 B1 | 12/2005 | Zenhausern |
| 6,976,382 B2 | 12/2005 | Kadowaki et al. |
| 6,978,212 B1 | 12/2005 | Sunshine |
| 6,979,260 B2 | 12/2005 | Liu |
| 6,979,363 B2 | 12/2005 | Boyd et al. |
| 6,981,368 B2 | 1/2006 | van Nieuwstadt et al. |
| 6,985,082 B1 | 1/2006 | Dutta et al. |

(56) References Cited

U.S. PATENT DOCUMENTS

| | | |
|---|---|---|
| 6,986,294 B2 | 1/2006 | Fromme et al. |
| 6,989,757 B2 | 1/2006 | Geoffrey J. et al. |
| 6,990,799 B2 | 1/2006 | Bidner et al. |
| 6,995,664 B1 | 2/2006 | Darling |
| 6,998,991 B1 | 2/2006 | Goldstein et al. |
| 7,002,481 B1 | 2/2006 | Crane et al. |
| 7,003,943 B2 | 2/2006 | Ketterer et al. |
| 7,005,994 B2 | 2/2006 | King |
| 7,007,458 B2 | 3/2006 | Mazur et al. |
| 7,007,542 B2 | 3/2006 | Wang et al. |
| 7,008,913 B2 | 3/2006 | Hei et al. |
| 7,012,544 B2 | 3/2006 | Cunningham et al. |
| 7,013,214 B2 | 3/2006 | Ohsaki |
| 7,015,943 B2 | 3/2006 | Chiang |
| 7,019,626 B1 | 3/2006 | Funk |
| 7,019,655 B2 | 3/2006 | Lopez et al. |
| 7,021,300 B2 | 4/2006 | Maki et al. |
| 7,024,869 B2 | 4/2006 | Puri et al. |
| 7,026,945 B2 | 4/2006 | Hill |
| 7,028,534 B2 | 4/2006 | Watanabe et al. |
| 7,030,748 B2 | 4/2006 | Tanguay |
| 7,040,307 B2 | 5/2006 | Nagashima et al. |
| 7,048,199 B2 | 5/2006 | Melink |
| 7,051,573 B2 | 5/2006 | Bresciani et al. |
| 7,051,689 B2 | 5/2006 | Tamura et al. |
| 7,053,822 B2 | 5/2006 | Rickerson, Jr. |
| 7,056,474 B2 | 6/2006 | Dumas et al. |
| 7,057,517 B1 | 6/2006 | Convery |
| 7,059,112 B2 | 6/2006 | Bidner et al. |
| 7,064,664 B2 | 6/2006 | Lerg et al. |
| 7,064,670 B2 | 6/2006 | Galperin et al. |
| 7,067,319 B2 | 6/2006 | Wills et al. |
| 7,069,142 B2 | 6/2006 | Keller et al. |
| 7,073,465 B2 | 7/2006 | Woll et al. |
| 7,076,371 B2 | 7/2006 | Fu |
| 7,077,741 B2 | 7/2006 | Brenner et al. |
| 7,080,544 B2 | 7/2006 | Stepanik et al. |
| 7,082,752 B2 | 8/2006 | Plote et al. |
| 7,083,110 B2 | 8/2006 | Kim et al. |
| 7,084,963 B2 | 8/2006 | Leipertz |
| 7,096,715 B2 | 8/2006 | Kita et al. |
| 7,100,420 B2 | 9/2006 | Read et al. |
| 7,100,586 B2 | 9/2006 | Matsumoto |
| 7,102,504 B2 | 9/2006 | Kates |
| 7,102,505 B2 | 9/2006 | Kates |
| 7,105,037 B2 | 9/2006 | Olander et al. |
| 7,107,758 B2 | 9/2006 | Hirooka |
| 7,108,774 B1 | 9/2006 | Laitinen-Vellonen |
| 7,109,874 B2 | 9/2006 | Pilkington |
| 7,109,879 B2 | 9/2006 | Stults et al. |
| 7,111,451 B2 | 9/2006 | Dou et al. |
| 7,112,443 B2 | 9/2006 | Hajduk et al. |
| 7,114,329 B2 | 10/2006 | Rosel et al. |
| 7,116,750 B1 | 10/2006 | Iaquinta et al. |
| 7,117,664 B2 | 10/2006 | Takaku et al. |
| 7,124,018 B2 | 10/2006 | Hassdenteufel et al. |
| 7,127,935 B2 | 10/2006 | Bonne et al. |
| 7,131,261 B2 | 11/2006 | Wackerow et al. |
| 7,131,262 B2 | 11/2006 | Sealy et al. |
| 7,131,322 B2 | 11/2006 | Booms et al. |
| 7,131,344 B2 | 11/2006 | Tarumi |
| 7,134,273 B2 | 11/2006 | Mazur et al. |
| 7,139,072 B1 | 11/2006 | Boss et al. |
| 7,140,230 B2 | 11/2006 | Kita et al. |
| 7,142,105 B2 | 11/2006 | Chen |
| 7,142,107 B2 | 11/2006 | Kates |
| 7,146,851 B2 | 12/2006 | Wakahara et al. |
| 7,151,787 B2 | 12/2006 | Kulp et al. |
| 7,154,579 B2 | 12/2006 | Selander et al. |
| 7,156,968 B2 | 1/2007 | Tsapakh et al. |
| 7,158,040 B2 | 1/2007 | Morris |
| 7,159,384 B2 | 1/2007 | Otake et al. |
| 7,160,732 B2 | 1/2007 | Lippard et al. |
| 7,161,678 B2 | 1/2007 | Schultz |
| 7,162,860 B2 | 1/2007 | Shirakawa et al. |
| 7,162,862 B2 | 1/2007 | Nagai et al. |
| 7,167,815 B2 | 1/2007 | Labreche et al. |
| 7,170,418 B2 | 1/2007 | Rose-Pehrsson et al. |
| 7,178,381 B2 | 2/2007 | Tajima et al. |
| 7,179,355 B2 | 2/2007 | Harper |
| 7,179,422 B2 | 2/2007 | Kirby et al. |
| 7,182,845 B2 | 2/2007 | Kaiser |
| 7,183,933 B2 | 2/2007 | Dzurko et al. |
| 7,189,373 B2 | 3/2007 | Taniguchi et al. |
| 7,190,171 B2 | 3/2007 | Kawakami et al. |
| 7,190,265 B1 | 3/2007 | Bohinc, Jr. |
| 7,190,276 B1 | 3/2007 | Lopez et al. |
| 7,192,459 B2 | 3/2007 | Puri et al. |
| 7,194,890 B2 | 3/2007 | Tanaka et al. |
| 7,199,724 B2 | 4/2007 | Danvir et al. |
| 7,200,348 B2 | 4/2007 | Brenner |
| 7,201,787 B2 | 4/2007 | Choi et al. |
| 7,202,795 B2 | 4/2007 | Karamanian et al. |
| 7,204,237 B2 | 4/2007 | Booms et al. |
| 7,210,289 B2 | 5/2007 | Sugano et al. |
| 7,212,734 B2 | 5/2007 | Pepper et al. |
| 7,216,478 B2 | 5/2007 | Brown et al. |
| 7,216,527 B2 | 5/2007 | Imoto |
| 7,217,354 B2 | 5/2007 | Mahurin et al. |
| 7,219,009 B1 | 5/2007 | Sager et al. |
| 7,221,171 B2 | 5/2007 | Sohl, III et al. |
| 7,222,615 B2 | 5/2007 | Buck et al. |
| 7,227,136 B2 | 6/2007 | Walte et al. |
| 7,229,831 B2 | 6/2007 | Puri |
| 7,229,833 B1 | 6/2007 | Andersson |
| 7,230,528 B2 | 6/2007 | Kates |
| 7,236,095 B2 | 6/2007 | Smith et al. |
| 7,237,504 B2 | 7/2007 | Davis et al. |
| 7,240,479 B1 | 7/2007 | Fujimoto |
| 7,240,668 B1 | 7/2007 | DeMinco |
| 7,241,881 B2 | 7/2007 | Vosshall et al. |
| 7,242,310 B2 | 7/2007 | Hotton et al. |
| 7,243,527 B2 | 7/2007 | Kim |
| 7,244,345 B1 | 7/2007 | Filanovsky |
| 7,246,604 B2 | 7/2007 | Cullen |
| 7,248,156 B2 | 7/2007 | Wisniewski et al. |
| H2197 H | 8/2007 | Gord |
| 7,254,474 B2 | 8/2007 | Iihoshi et al. |
| 7,257,481 B2 | 8/2007 | Shimura et al. |
| 7,257,941 B1 | 8/2007 | Reuter |
| 7,259,670 B2 | 8/2007 | Cunningham et al. |
| 7,262,060 B2 | 8/2007 | Hirowatari et al. |
| 7,264,778 B2 | 9/2007 | McDaniel et al. |
| 7,265,662 B2 | 9/2007 | Belanger |
| 7,268,683 B2 | 9/2007 | Andres et al. |
| 7,269,996 B2 | 9/2007 | Schnaibel et al. |
| 7,270,600 B2 | 9/2007 | Kim et al. |
| 7,278,304 B2 | 10/2007 | Zanini-Fisher et al. |
| 7,278,414 B2 | 10/2007 | Diem |
| 7,279,080 B2 | 10/2007 | Chapples et al. |
| 7,280,214 B2 | 10/2007 | DiFoggio et al. |
| 7,281,369 B2 | 10/2007 | Emi et al. |
| 7,281,439 B2 | 10/2007 | Schmitt et al. |
| 7,289,786 B2 | 10/2007 | Krasner |
| 7,296,459 B2 | 11/2007 | Son et al. |
| 7,298,252 B1 | 11/2007 | Sutardja et al. |
| 7,299,625 B2 | 11/2007 | Uchida et al. |
| 7,302,959 B2 | 12/2007 | Gonia |
| 7,310,047 B2 | 12/2007 | Al-Wehebi |
| 7,314,165 B2 | 1/2008 | Bonalle et al. |
| 7,314,723 B2 | 1/2008 | Zwiebel |
| 7,317,927 B2 | 1/2008 | Staton et al. |
| 7,319,402 B1 | 1/2008 | Sudderth |
| 7,319,403 B2 | 1/2008 | Woodard et al. |
| 7,325,393 B2 | 2/2008 | Miura |
| 7,325,748 B2 | 2/2008 | Acker, Jr. |
| 7,333,129 B2 | 2/2008 | Miller et al. |
| 7,334,401 B2 | 2/2008 | Cheng |
| 7,336,168 B2 | 2/2008 | Kates |
| 7,342,504 B2 | 3/2008 | Crane et al. |
| 7,343,734 B2 | 3/2008 | Aliakbarzadeh et al. |
| H2215 H | 4/2008 | Allen et al. |
| 7,351,591 B2 | 4/2008 | Koo et al. |
| 7,357,015 B2 | 4/2008 | Taguchi et al. |

(56) References Cited

U.S. PATENT DOCUMENTS

| | | |
|---|---|---|
| 7,365,539 B2 | 4/2008 | Szyperski et al. |
| 7,372,370 B2 | 5/2008 | Stults et al. |
| 7,374,878 B2 | 5/2008 | Stryer et al. |
| 7,378,954 B2 | 5/2008 | Wendt |
| 7,384,524 B2 | 6/2008 | Kirby et al. |
| 7,387,011 B2 | 6/2008 | Fujiki et al. |
| 7,388,383 B2 | 6/2008 | Kawakami et al. |
| 7,389,158 B2 | 6/2008 | Desrochers et al. |
| 7,390,664 B2 | 6/2008 | Fung et al. |
| 7,390,670 B2 | 6/2008 | Akhavan-Tafti et al. |
| 7,391,316 B2 | 6/2008 | Albert et al. |
| 7,401,503 B2 | 7/2008 | Binnig |
| 7,403,128 B2 | 7/2008 | Scuka et al. |
| 7,403,850 B1 | 7/2008 | Boutin et al. |
| 7,404,397 B2 | 7/2008 | Dobeck |
| 7,404,882 B2 | 7/2008 | Prohaska et al. |
| 7,406,871 B2 | 8/2008 | Sugiura |
| 7,407,650 B2 | 8/2008 | Heltovics et al. |
| 7,408,473 B2 | 8/2008 | Adkins et al. |
| 7,410,616 B2 | 8/2008 | Santini, Jr. et al. |
| 7,411,494 B2 | 8/2008 | Kates |
| 7,411,671 B2 | 8/2008 | De Vandiere et al. |
| 7,413,731 B2 | 8/2008 | Heltovics et al. |
| 7,414,726 B1 | 8/2008 | Bambeck |
| 7,415,343 B2 | 8/2008 | Zushi et al. |
| 7,415,901 B2 | 8/2008 | Desrochers et al. |
| 7,417,540 B2 | 8/2008 | Johnston et al. |
| 7,420,473 B2 | 9/2008 | Eicken et al. |
| 7,420,662 B2 | 9/2008 | Yalin et al. |
| 7,421,836 B2 | 9/2008 | Pallett et al. |
| 7,421,911 B2 | 9/2008 | Desrochers et al. |
| 7,422,646 B2 | 9/2008 | Prohaska et al. |
| 7,423,543 B2 | 9/2008 | Cartwright et al. |
| 7,425,307 B2 | 9/2008 | Sohl, III et al. |
| 7,425,445 B2 | 9/2008 | Matsunami et al. |
| 7,432,113 B2 | 10/2008 | Koo et al. |
| 7,433,777 B2 | 10/2008 | Ikari et al. |
| 7,433,778 B2 | 10/2008 | Mehnert |
| 7,434,744 B2 | 10/2008 | Garozzo et al. |
| 7,442,343 B2 | 10/2008 | Salisbury et al. |
| 7,444,235 B2 | 10/2008 | Anilovich et al. |
| 7,449,990 B2 | 11/2008 | Andres et al. |
| 7,454,895 B2 | 11/2008 | Hoard et al. |
| 7,455,444 B2 | 11/2008 | Chien |
| 7,461,536 B2 | 12/2008 | Schnaibel et al. |
| 7,462,218 B2 | 12/2008 | Ducrocq |
| 7,464,580 B2 | 12/2008 | Zeng et al. |
| 7,477,983 B2 | 1/2009 | Shimura et al. |
| 7,479,893 B2 | 1/2009 | Weston et al. |
| 7,480,044 B2 | 1/2009 | Leipertz |
| 7,483,781 B2 | 1/2009 | Wakahara et al. |
| 7,485,169 B2 | 2/2009 | Olander et al. |
| 7,487,035 B2 | 2/2009 | Nozawa et al. |
| 7,487,662 B2 | 2/2009 | Schabron et al. |
| 7,492,255 B1 | 2/2009 | Morris |
| 7,499,792 B2 | 3/2009 | Rosel et al. |
| 7,502,115 B2 | 3/2009 | Patel et al. |
| 7,503,899 B2 | 3/2009 | Caillouette |
| 7,504,235 B2 | 3/2009 | Song |
| 7,508,314 B2 | 3/2009 | Andres et al. |
| 7,510,470 B2 | 3/2009 | Arts |
| 7,515,058 B2 | 4/2009 | Normand |
| 7,519,467 B2 | 4/2009 | Katoh |
| 7,521,018 B2 | 4/2009 | Niemann et al. |
| 7,522,039 B2 | 4/2009 | Sutardja et al. |
| 7,523,653 B2 | 4/2009 | Smith et al. |
| 7,525,445 B2 | 4/2009 | DeLuca et al. |
| 7,526,950 B2 | 5/2009 | Van Nieuwstadt et al. |
| 7,528,732 B2 | 5/2009 | Tajima et al. |
| 7,531,007 B2 | 5/2009 | Sharma |
| 7,531,137 B2 | 5/2009 | Uluyol |
| 7,531,349 B1 | 5/2009 | Shepard et al. |
| 7,536,244 B2 | 5/2009 | Kunihiro et al. |
| RE40,767 E | 6/2009 | Peterson et al. |
| 7,546,761 B2 | 6/2009 | He et al. |
| 7,552,005 B2 | 6/2009 | Kim et al. |
| 7,556,774 B2 | 7/2009 | Rakow et al. |
| 7,557,092 B2 | 7/2009 | Lucero et al. |
| 7,558,667 B2 | 7/2009 | Kida |
| 7,559,193 B2 | 7/2009 | Iihoshi et al. |
| 7,564,362 B2 | 7/2009 | Cole et al. |
| 7,565,273 B2 | 7/2009 | Hengerer |
| 7,567,174 B2 | 7/2009 | Woodard et al. |
| 7,568,376 B2 | 8/2009 | Strohmaier et al. |
| 7,568,377 B2 | 8/2009 | Bhethanabotla et al. |
| 7,571,640 B2 | 8/2009 | Andrews |
| 7,574,195 B2 | 8/2009 | Krasner et al. |
| 7,574,246 B2 | 8/2009 | Krebs et al. |
| 7,574,893 B2 | 8/2009 | Mitachi et al. |
| 7,574,905 B2 | 8/2009 | Toya |
| 7,575,709 B2 | 8/2009 | Mukundan et al. |
| 7,576,659 B2 | 8/2009 | Lax |
| 7,579,587 B2 | 8/2009 | Krogh et al. |
| 7,579,956 B2 | 8/2009 | Chapman, Jr. et al. |
| 7,580,137 B2 | 8/2009 | Wilson et al. |
| 7,580,772 B2 | 8/2009 | Stolyar et al. |
| 7,582,480 B2 | 9/2009 | Audoin et al. |
| 7,582,485 B2 | 9/2009 | Boga et al. |
| 7,586,409 B2 | 9/2009 | Armstrong et al. |
| 7,587,331 B2 | 9/2009 | Pelletier |
| 7,587,926 B2 | 9/2009 | Ackerman |
| 7,588,368 B2 | 9/2009 | Hagen et al. |
| 7,592,916 B2 | 9/2009 | Staples |
| 7,592,923 B2 | 9/2009 | Lax |
| 7,596,993 B2 | 10/2009 | Fukagai et al. |
| 7,601,250 B2 | 10/2009 | Prohaska et al. |
| 7,602,283 B2 | 10/2009 | John |
| 7,608,459 B2 | 10/2009 | Yabuki et al. |
| 7,611,671 B2 | 11/2009 | Anvar et al. |
| 7,613,554 B2 | 11/2009 | Rollinger et al. |
| 7,615,377 B2 | 11/2009 | Lippard et al. |
| 7,617,674 B2 | 11/2009 | Gerlach |
| 7,623,028 B2 | 11/2009 | Kates |
| 7,628,007 B2 | 12/2009 | Kittelson et al. |
| 7,628,063 B2 | 12/2009 | Yezerets et al. |
| 7,630,826 B2 | 12/2009 | Wang et al. |
| 7,631,568 B2 | 12/2009 | Kilps et al. |
| 7,632,178 B2 | 12/2009 | Meneely, Jr. |
| 7,633,386 B2 | 12/2009 | Bennett |
| 7,633,397 B2 | 12/2009 | Dugan |
| 7,642,924 B2 | 1/2010 | Andres et al. |
| 7,647,765 B2 | 1/2010 | Sealy et al. |
| 7,648,954 B2 | 1/2010 | Saudan et al. |
| 7,649,472 B1 | 1/2010 | Paterno |
| 7,651,597 B2 | 1/2010 | Saffell et al. |
| 7,657,384 B1 | 2/2010 | Moses |
| 7,659,825 B2 | 2/2010 | Kim et al. |
| 7,661,298 B2 | 2/2010 | Hartmann et al. |
| 7,665,670 B2 | 2/2010 | Ahmed |
| 7,670,843 B2 | 3/2010 | Schechter et al. |
| 7,675,423 B2 | 3/2010 | Boling et al. |
| 7,679,879 B2 | 3/2010 | Furuhashi et al. |
| 7,681,565 B2 | 3/2010 | Fujiki |
| 7,683,792 B2 | 3/2010 | Araiza-Boys |
| 7,683,794 B2 | 3/2010 | Contreras |
| 7,687,252 B2 | 3/2010 | Ghosh |
| 7,687,744 B2 | 3/2010 | Walter et al. |
| 7,687,770 B2 | 3/2010 | Indo et al. |
| 7,687,776 B2 | 3/2010 | Baliga et al. |
| RE41,190 E | 4/2010 | Darling |
| 7,691,592 B2 | 4/2010 | Matsunami et al. |
| 7,694,506 B2 | 4/2010 | Berger et al. |
| 7,694,547 B2 | 4/2010 | Dutta et al. |
| 7,696,891 B2 | 4/2010 | Whitney |
| 7,704,751 B2 | 4/2010 | Palazzotto et al. |
| 7,705,988 B2 | 4/2010 | Richman |
| 7,707,821 B1 | 5/2010 | Legare |
| 7,710,284 B2 | 5/2010 | Dzurko et al. |
| 7,717,095 B2 | 5/2010 | Liu |
| 7,721,591 B2 | 5/2010 | Maegawa |
| 7,735,312 B2 | 6/2010 | Votsmeier et al. |
| 7,743,738 B2 | 6/2010 | Rainear et al. |
| 7,746,240 B2 | 6/2010 | Vij |
| 7,746,241 B2 | 6/2010 | Feight et al. |

(56) References Cited

U.S. PATENT DOCUMENTS

| | | |
|---|---|---|
| 7,748,213 B2 | 7/2010 | I et al. |
| 7,751,966 B2 | 7/2010 | Iwazaki |
| 7,752,837 B2 | 7/2010 | Iihoshi et al. |
| 7,752,901 B1 | 7/2010 | Holmen |
| 7,754,491 B2 | 7/2010 | Park et al. |
| 7,755,481 B2 | 7/2010 | Gayden |
| 7,755,494 B2 | 7/2010 | Melker et al. |
| 7,759,924 B2 | 7/2010 | Shekhawat et al. |
| 7,763,154 B2 | 7/2010 | Schumann et al. |
| 7,768,391 B2 | 8/2010 | Koyama et al. |
| 7,768,413 B2 | 8/2010 | Kosuge et al. |
| 7,768,647 B2 | 8/2010 | Reeve et al. |
| 7,769,534 B1 | 8/2010 | Xu et al. |
| 7,770,326 B2 | 8/2010 | Al-Qassem |
| 7,770,476 B2 | 8/2010 | Davis et al. |
| 7,771,113 B2 | 8/2010 | Corbet et al. |
| 7,774,038 B2 | 8/2010 | Wang et al. |
| 7,778,766 B1 | 8/2010 | Cowgill et al. |
| 7,779,669 B2 | 8/2010 | Fukagai et al. |
| 7,780,092 B2 | 8/2010 | Ahmed |
| 7,781,218 B2 | 8/2010 | Furton et al. |
| 7,782,191 B2 | 8/2010 | Flores |
| 7,786,879 B2 | 8/2010 | Lax |
| 7,786,889 B2 | 8/2010 | Van Der Poel et al. |
| 7,793,538 B2 | 9/2010 | Kariya et al. |
| 7,801,666 B2 | 9/2010 | Mitsuda et al. |
| 7,802,563 B2 | 9/2010 | Behr et al. |
| 7,805,974 B2 | 10/2010 | Scheffler et al. |
| 7,806,008 B2 | 10/2010 | Binnig |
| 7,810,313 B2 | 10/2010 | Stewart et al. |
| 7,815,327 B2 | 10/2010 | Shamshoian |
| 7,817,499 B2 | 10/2010 | Solhjoo et al. |
| 7,820,108 B2 | 10/2010 | Lampotang et al. |
| 7,821,392 B2 | 10/2010 | Brown |
| 7,823,377 B2 | 11/2010 | Griard |
| 7,829,714 B2 | 11/2010 | Whateley et al. |
| 7,832,260 B2 | 11/2010 | Tanaka |
| 7,833,397 B2 | 11/2010 | Kimura |
| 7,835,005 B2 | 11/2010 | Appel et al. |
| 7,836,758 B2 | 11/2010 | Aono et al. |
| 7,837,663 B2 | 11/2010 | MacDonald et al. |
| 7,838,288 B2 | 11/2010 | Matsunami et al. |
| 7,838,297 B2 | 11/2010 | Widmer et al. |
| 7,838,799 B2 | 11/2010 | Freedman |
| 7,840,366 B1 | 11/2010 | Moses et al. |
| 7,841,173 B2 | 11/2010 | Clever |
| 7,842,284 B2 | 11/2010 | Johnson |
| 7,843,324 B2 | 11/2010 | Penney et al. |
| 7,846,742 B2 | 12/2010 | Sapir et al. |
| 7,848,732 B2 | 12/2010 | Thomas |
| 7,849,672 B2 | 12/2010 | Shibata et al. |
| 7,849,844 B2 | 12/2010 | Rosel |
| 7,851,225 B2 | 12/2010 | Colvin, Jr. et al. |
| 7,854,161 B2 | 12/2010 | Hjorsberg et al. |
| 7,858,378 B2 | 12/2010 | Yabuki et al. |
| 7,861,515 B2 | 1/2011 | Brahma |
| 7,864,322 B2 | 1/2011 | Carpenter et al. |
| 7,866,202 B2 | 1/2011 | Chen et al. |
| 7,874,285 B2 | 1/2011 | Barnikow et al. |
| 7,879,565 B2 | 2/2011 | Matsunami et al. |
| 7,880,468 B2 | 2/2011 | Szyperski et al. |
| 7,881,858 B2 | 2/2011 | Kress et al. |
| 7,886,523 B1 | 2/2011 | Legare |
| 7,886,577 B2 | 2/2011 | Zeng |
| 7,889,088 B1 | 2/2011 | Billman |
| RE42,192 E | 3/2011 | Schabron et al. |
| 7,897,400 B2 | 3/2011 | Timmins et al. |
| 7,900,439 B2 | 3/2011 | Genslak et al. |
| 7,900,500 B2 | 3/2011 | Krafthefer |
| 7,900,616 B2 | 3/2011 | Saunders |
| 7,904,053 B2 | 3/2011 | Krasner et al. |
| 7,905,154 B2 | 3/2011 | Jones, Jr. |
| 7,907,052 B2 | 3/2011 | Delaney, Jr. |
| 7,908,991 B2 | 3/2011 | Woods et al. |
| 7,913,540 B2 | 3/2011 | Brasfield |
| 7,913,550 B2 | 3/2011 | Schoenthaler et al. |
| 7,915,047 B2 | 3/2011 | Thorn et al. |
| 7,919,304 B2 | 4/2011 | Egan et al. |
| 7,920,842 B2 | 4/2011 | Martin et al. |
| 7,920,972 B2 | 4/2011 | Szyperski et al. |
| 7,921,706 B2 | 4/2011 | Sumitani |
| 7,926,483 B2 | 4/2011 | Lundeen |
| 7,926,734 B2 | 4/2011 | Dobler et al. |
| 7,930,876 B2 | 4/2011 | Thouvenel et al. |
| 7,930,923 B2 | 4/2011 | Patel et al. |
| 7,930,924 B2 | 4/2011 | Krogh et al. |
| 7,932,482 B2 | 4/2011 | Norwood et al. |
| 7,933,710 B2 | 4/2011 | Tanaka et al. |
| 7,937,216 B2 | 5/2011 | Humphrey |
| 7,944,352 B2 | 5/2011 | Drake et al. |
| 7,945,301 B2 | 5/2011 | Krebs et al. |
| H2256 H | 6/2011 | Rayms-Keller |
| 7,954,364 B2 | 6/2011 | Shoda |
| 7,957,919 B2 | 6/2011 | Marconi |
| 7,963,453 B2 | 6/2011 | Peterson et al. |
| 7,963,460 B2 | 6/2011 | Jorgensen |
| 7,968,516 B2 | 6/2011 | Stracher et al. |
| 7,969,296 B1 | 6/2011 | Stell |
| 7,972,277 B2 | 7/2011 | Oki et al. |
| 7,972,488 B2 | 7/2011 | Oya et al. |
| 7,973,669 B2 | 7/2011 | Pham et al. |
| 7,977,955 B2 | 7/2011 | Katsuyama et al. |
| 7,978,083 B2 | 7/2011 | Melker et al. |
| 7,987,039 B2 | 7/2011 | Takagawa |
| 7,987,695 B2 | 8/2011 | Kilps et al. |
| 7,988,771 B2 | 8/2011 | Anikhindi et al. |
| 7,993,587 B2 | 8/2011 | Mayer et al. |
| 7,997,064 B2 | 8/2011 | Arlt et al. |
| 7,998,419 B2 | 8/2011 | Furuhashi et al. |
| 8,003,399 B2 | 8/2011 | Song et al. |
| 8,005,603 B2 | 8/2011 | Fisher et al. |
| 8,006,542 B2 | 8/2011 | Jones, Jr. |
| 8,006,670 B2 | 8/2011 | Rollinger et al. |
| 8,016,205 B2 | 9/2011 | Drew |
| 8,019,525 B2 | 9/2011 | DeBastos et al. |
| 8,024,103 B2 | 9/2011 | Kassner |
| 8,026,103 B2 | 9/2011 | Van Herpen |
| 8,026,804 B2 | 9/2011 | Wu et al. |
| 8,026,825 B2 | 9/2011 | Santos |
| 8,029,153 B2 | 10/2011 | Jorgensen |
| 8,031,335 B2 | 10/2011 | Wang et al. |
| 8,034,290 B1 | 10/2011 | Skiba et al. |
| 8,036,814 B2 | 10/2011 | Weber et al. |
| 8,038,778 B2 | 10/2011 | Chan et al. |
| 8,038,946 B1 | 10/2011 | Harper et al. |
| 8,041,516 B2 | 10/2011 | Angell et al. |
| 8,042,385 B2 | 10/2011 | Brennan et al. |
| 8,042,528 B2 | 10/2011 | Gates et al. |
| 8,047,163 B2 | 11/2011 | Tian et al. |
| 8,049,619 B2 | 11/2011 | Armstrong et al. |
| 8,054,188 B2 | 11/2011 | Harkins et al. |
| 8,056,540 B2 | 11/2011 | DeBastos et al. |
| 8,059,150 B2 | 11/2011 | Gal |
| 8,065,871 B1 | 11/2011 | Fraser |
| 8,066,859 B2 | 11/2011 | Johnston et al. |
| 8,066,939 B2 | 11/2011 | Elrod |
| 8,073,405 B2 | 12/2011 | Tougou |
| 8,075,759 B2 | 12/2011 | Schnaibel et al. |
| 8,077,046 B1 | 12/2011 | Wong |
| 8,077,048 B2 | 12/2011 | Almiman |
| 8,078,388 B2 | 12/2011 | Powell |
| 8,079,351 B2 | 12/2011 | Uhrich et al. |
| 8,080,206 B2 | 12/2011 | Leddy et al. |
| 8,083,575 B2 | 12/2011 | Kim |
| 8,085,152 B2 | 12/2011 | Liu |
| 8,086,266 B2 | 12/2011 | Kotidis |
| 8,087,290 B2 | 1/2012 | Wickert et al. |
| 8,091,404 B2 | 1/2012 | Sawada et al. |
| 8,091,416 B2 | 1/2012 | Wang et al. |
| 8,091,538 B2 | 1/2012 | Hartmann et al. |
| 8,095,296 B2 | 1/2012 | Kirstaetter et al. |
| 8,099,946 B2 | 1/2012 | Hinz et al. |
| 8,099,947 B2 | 1/2012 | Makki et al. |
| 8,103,430 B2 | 1/2012 | Aliakbarzadeh |

(56) References Cited

U.S. PATENT DOCUMENTS

| | | |
|---|---|---|
| 8,104,334 B2 | 1/2012 | Wang et al. |
| 8,105,584 B2 | 1/2012 | Fallon |
| 8,107,920 B2 | 1/2012 | Ben Ayed |
| 8,109,452 B2 | 2/2012 | Akisada et al. |
| 8,112,984 B2 | 2/2012 | Dietl et al. |
| 8,114,904 B2 | 2/2012 | Yang et al. |
| 8,120,501 B2 | 2/2012 | Mancini |
| 8,122,753 B2 | 2/2012 | Tryfonos et al. |
| 8,123,923 B2 | 2/2012 | Prohaska et al. |
| 8,127,593 B2 | 3/2012 | Moularat |
| 8,130,105 B2 | 3/2012 | Al-Ali et al. |
| 8,132,450 B2 | 3/2012 | Shibata et al. |
| 8,133,434 B2 | 3/2012 | Bankers et al. |
| 8,134,458 B2 | 3/2012 | Lund |
| 8,134,470 B2 | 3/2012 | Agurs |
| 8,137,979 B2 | 3/2012 | Combes et al. |
| 8,143,068 B2 | 3/2012 | Colvin, Jr. et al. |
| 8,146,346 B2 | 4/2012 | Ishibashi |
| 8,146,352 B2 | 4/2012 | Parnin |
| 8,146,562 B2 | 4/2012 | Yezerets et al. |
| 8,148,995 B2 | 4/2012 | Hashimoto et al. |
| 8,152,992 B2 | 4/2012 | Smela et al. |
| 8,153,065 B2 | 4/2012 | Zang et al. |
| 8,153,439 B2 | 4/2012 | Zamborini et al. |
| 8,154,093 B2 | 4/2012 | Bradley et al. |
| 8,156,728 B2 | 4/2012 | Hinz et al. |
| 8,161,808 B2 | 4/2012 | Crawford et al. |
| 8,165,719 B2 | 4/2012 | Kinney et al. |
| 8,166,749 B2 | 5/2012 | Gady |
| 8,171,720 B2 | 5/2012 | Wang et al. |
| 8,171,721 B2 | 5/2012 | Boddy et al. |
| 8,171,781 B2 | 5/2012 | Shibata et al. |
| 8,173,430 B2 | 5/2012 | Cohen-Arazi et al. |
| 8,175,884 B1 | 5/2012 | Morris |
| 8,186,205 B2 | 5/2012 | Wehmeier et al. |
| 8,187,887 B2 | 5/2012 | Swager et al. |
| 8,190,223 B2 | 5/2012 | Al-Ali et al. |
| 8,190,352 B2 | 5/2012 | Brandt et al. |
| 8,190,397 B2 | 5/2012 | Kurokawa |
| 8,195,354 B2 | 6/2012 | Kariya et al. |
| 8,196,903 B2 | 6/2012 | Jorgensen |
| 8,200,411 B2 | 6/2012 | DeBastos et al. |
| 8,201,444 B2 | 6/2012 | Wang et al. |
| 8,203,445 B2 | 6/2012 | Recker et al. |
| 8,203,458 B2 | 6/2012 | Kaneblei et al. |
| 8,205,436 B2 | 6/2012 | Berke et al. |
| 8,205,437 B2 | 6/2012 | Arnold et al. |
| 8,209,110 B2 | 6/2012 | Weber et al. |
| 8,209,964 B2 | 7/2012 | Kesse |
| 8,211,035 B2 | 7/2012 | Melker et al. |
| 8,211,208 B2 | 7/2012 | Chan et al. |
| 8,214,176 B2 | 7/2012 | Iwazaki et al. |
| 8,215,291 B2 | 7/2012 | DeBastos et al. |
| 8,219,278 B2 | 7/2012 | Sawada et al. |
| 8,224,282 B2 | 7/2012 | Songkakul et al. |
| 8,225,647 B2 | 7/2012 | Mukai |
| 8,230,677 B2 | 7/2012 | Devarakonda et al. |
| 8,230,716 B2 | 7/2012 | Nelson et al. |
| 8,232,072 B2 | 7/2012 | Kalnik et al. |
| 8,232,884 B2 | 7/2012 | Pattok et al. |
| 8,234,030 B2 | 7/2012 | Sugimoto |
| 8,240,129 B2 | 8/2012 | Yezerets et al. |
| 8,240,130 B2 | 8/2012 | Sawada et al. |
| 8,240,193 B2 | 8/2012 | Frauhammer et al. |
| 8,242,899 B2 | 8/2012 | Albert et al. |
| 8,245,497 B2 | 8/2012 | Yoda et al. |
| 8,245,566 B2 | 8/2012 | Wehmeier et al. |
| 8,245,567 B2 | 8/2012 | Wang et al. |
| 8,246,549 B2 | 8/2012 | Janski et al. |
| 8,249,510 B2 | 8/2012 | Chabin et al. |
| 8,249,827 B2 | 8/2012 | Nelson et al. |
| 8,252,099 B2 | 8/2012 | Worrilow |
| 8,253,553 B2 | 8/2012 | Wedig et al. |
| 8,253,558 B2 | 8/2012 | Emerson et al. |
| 8,256,208 B2 | 9/2012 | Wills et al. |
| 8,256,264 B2 | 9/2012 | Bosi et al. |
| 8,258,969 B1 | 9/2012 | Billman |
| 8,260,576 B2 | 9/2012 | Iwazaki et al. |
| 8,261,540 B2 | 9/2012 | Konstandopoulos et al. |
| 8,264,326 B2 | 9/2012 | Hayashi et al. |
| 8,268,241 B1 | 9/2012 | Cooper |
| 8,269,625 B2 | 9/2012 | Hoy et al. |
| 8,272,250 B2 | 9/2012 | Wang et al. |
| 8,273,298 B2 | 9/2012 | Newell |
| 8,274,393 B2 | 9/2012 | Ales et al. |
| 8,281,576 B2 | 10/2012 | Parnin |
| 8,286,417 B2 | 10/2012 | Allmer et al. |
| 8,286,603 B2 | 10/2012 | Sid |
| 8,286,610 B2 | 10/2012 | Moriya |
| 8,287,811 B1 | 10/2012 | Harper et al. |
| 8,290,688 B2 | 10/2012 | Watson |
| 8,294,567 B1 | 10/2012 | Stell |
| 8,297,040 B2 | 10/2012 | Rosel |
| 8,302,378 B2 | 11/2012 | Miyoshi et al. |
| 8,303,174 B2 | 11/2012 | Kasahara |
| 8,303,697 B2 | 11/2012 | Chan et al. |
| 8,307,699 B2 | 11/2012 | Sawada et al. |
| 8,309,310 B2 | 11/2012 | Enderle et al. |
| 8,310,016 B2 | 11/2012 | Stetter |
| 8,311,721 B2 | 11/2012 | Whitney et al. |
| 8,320,751 B2 | 11/2012 | Porchia et al. |
| 8,327,628 B2 | 12/2012 | Ruona et al. |
| 8,327,696 B2 | 12/2012 | Baars et al. |
| 8,329,099 B1 | 12/2012 | Skiba et al. |
| 8,333,125 B2 | 12/2012 | Tsai et al. |
| 8,333,816 B2 | 12/2012 | Kummer et al. |
| 8,334,387 B2 | 12/2012 | Whateley et al. |
| 8,334,505 B2 | 12/2012 | Robinson et al. |
| 8,336,291 B2 | 12/2012 | Hanari et al. |
| 8,336,525 B2 | 12/2012 | Runde et al. |
| 8,341,937 B2 | 1/2013 | I et al. |
| 8,341,938 B2 | 1/2013 | Votsmeier et al. |
| 8,350,710 B2 | 1/2013 | Logan et al. |
| 8,354,935 B2 | 1/2013 | Rauworth |
| 8,357,304 B2 | 1/2013 | Reich et al. |
| 8,359,826 B2 | 1/2013 | Kitazawa |
| 8,366,630 B2 | 2/2013 | Haick et al. |
| 8,368,754 B2 | 2/2013 | Flores et al. |
| 8,371,547 B2 | 2/2013 | Wilkowske |
| 8,374,586 B2 | 2/2013 | Bentkovski et al. |
| 8,375,913 B2 | 2/2013 | Kwiecinski et al. |
| 8,377,706 B2 | 2/2013 | Hong et al. |
| 8,378,817 B2 | 2/2013 | Fox |
| 8,384,397 B2 | 2/2013 | Bromberg et al. |
| 8,392,029 B2 | 3/2013 | Nakamoto et al. |
| 8,393,141 B2 | 3/2013 | Sebestyen et al. |
| 8,400,317 B2 | 3/2013 | Johnson, Jr. et al. |
| 8,401,727 B2 | 3/2013 | Arlt et al. |
| 8,407,983 B2 | 4/2013 | Mukai |
| 8,407,986 B2 | 4/2013 | Hahn |
| 8,410,935 B2 | 4/2013 | Jackson |
| 8,413,421 B2 | 4/2013 | Fujimoto |
| 8,413,422 B2 | 4/2013 | Kasahara |
| 8,413,497 B2 | 4/2013 | Kayama et al. |
| 8,418,438 B2 | 4/2013 | Shimomura et al. |
| 8,418,942 B2 | 4/2013 | Suda et al. |
| 8,423,192 B2 | 4/2013 | Liu |
| 8,423,243 B2 | 4/2013 | Harima |
| 8,424,288 B2 | 4/2013 | De Tricaud et al. |
| 8,426,208 B2 | 4/2013 | Swager et al. |
| 8,426,215 B2 | 4/2013 | Mueller et al. |
| 8,426,932 B2 | 4/2013 | Stetter |
| 8,428,954 B2 | 4/2013 | Morris |
| 8,430,096 B2 | 4/2013 | Chambers |
| 8,432,451 B2 | 4/2013 | Cetin et al. |
| RE44,214 E | 5/2013 | Peterson et al. |
| 8,434,349 B2 | 5/2013 | Blomberg et al. |
| 8,435,448 B2 | 5/2013 | Park et al. |
| 8,437,965 B2 | 5/2013 | Sjong |
| 8,440,068 B2 | 5/2013 | Kimura |
| 8,441,357 B2 | 5/2013 | Ohya |
| 8,442,611 B2 | 5/2013 | Santini, Jr. et al. |
| 8,447,495 B2 | 5/2013 | Pearce et al. |
| 8,447,528 B2 | 5/2013 | Gentala et al. |

(56) References Cited

U.S. PATENT DOCUMENTS

| | | |
|---|---|---|
| 8,448,739 B2 | 5/2013 | Kolich |
| 8,451,132 B1 | 5/2013 | Van Vleet |
| 8,459,005 B2 | 6/2013 | Zhang |
| 8,461,354 B2 | 6/2013 | Babudri et al. |
| 8,464,663 B2 | 6/2013 | Kodat |
| 8,468,799 B2 | 6/2013 | Post et al. |
| 8,469,010 B2 | 6/2013 | Inoue |
| 8,469,244 B2 | 6/2013 | Helf et al. |
| 8,470,933 B2 | 6/2013 | Thorn et al. |
| 8,476,023 B2 | 7/2013 | Lazarus et al. |
| 8,481,270 B2 | 7/2013 | Gniewek et al. |
| 8,481,324 B2 | 7/2013 | Haick et al. |
| 8,481,470 B2 | 7/2013 | Jones, Jr. |
| 8,484,949 B2 | 7/2013 | Sebestyen et al. |
| 8,487,240 B2 | 7/2013 | Koehl |
| 8,489,361 B2 | 7/2013 | Umehara |
| 8,490,385 B2 | 7/2013 | Miyoshi et al. |
| 8,490,465 B2 | 7/2013 | Ante et al. |
| 8,490,476 B2 | 7/2013 | Hopka et al. |
| 8,495,860 B2 | 7/2013 | Gresens |
| 8,496,737 B2 | 7/2013 | Kim et al. |
| 8,499,545 B2 | 8/2013 | Busch et al. |
| 8,499,613 B2 | 8/2013 | Ziglioli et al. |
| 8,500,442 B2 | 8/2013 | Knittel et al. |
| 8,505,370 B2 | 8/2013 | Miller |
| 8,505,371 B2 | 8/2013 | Zimmerman et al. |
| 8,515,710 B2 | 8/2013 | Wang et al. |
| 8,518,663 B2 | 8/2013 | Trevejo et al. |
| 8,518,703 B1 | 8/2013 | Wright |
| 8,519,182 B2 | 8/2013 | Salisbury et al. |
| 8,521,354 B2 | 8/2013 | Sasaki |
| 8,521,405 B2 | 8/2013 | Maruyama |
| 8,525,665 B1 | 9/2013 | Trundle et al. |
| 8,525,666 B2 | 9/2013 | Melker et al. |
| 8,528,319 B2 | 9/2013 | Wilhelm et al. |
| 8,529,846 B1 | 9/2013 | Wright |
| 8,534,258 B2 | 9/2013 | Cristoforo |
| 8,539,757 B2 | 9/2013 | Hirota et al. |
| 8,539,914 B2 | 9/2013 | Kerns et al. |
| 8,542,107 B2 | 9/2013 | Dolan |
| 8,542,115 B2 | 9/2013 | Karim et al. |
| 8,543,288 B2 | 9/2013 | Bligard et al. |
| 8,544,258 B2 | 10/2013 | Brown et al. |
| 8,547,237 B2 | 10/2013 | Adebimpe |
| 8,550,368 B2 | 10/2013 | Butler et al. |
| 8,551,214 B2 | 10/2013 | Dudar et al. |
| 8,555,613 B2 | 10/2013 | Wang et al. |
| 8,555,618 B2 | 10/2013 | Bauer et al. |
| 8,555,700 B2 | 10/2013 | Dikken |
| 8,556,505 B2 | 10/2013 | Akins et al. |
| 8,558,696 B2 | 10/2013 | Baumann et al. |
| 8,561,387 B2 | 10/2013 | Fokkelman |
| 8,566,023 B2 | 10/2013 | Riggins et al. |
| 8,572,952 B2 | 11/2013 | Parnin |
| 8,577,645 B2 | 11/2013 | Turin et al. |
| 8,583,349 B2 | 11/2013 | Anilovich et al. |
| 8,584,189 B2 | 11/2013 | Emerson et al. |
| 8,586,383 B2 | 11/2013 | Walte et al. |
| 8,590,289 B2 | 11/2013 | Maki |
| 8,596,045 B2 | 12/2013 | Tuomivaara et al. |
| 8,597,956 B2 | 12/2013 | Willner et al. |
| 8,602,854 B1 | 12/2013 | Moore |
| 8,608,835 B2 | 12/2013 | Busch |
| 8,613,219 B2 | 12/2013 | Kitaura et al. |
| 8,617,498 B2 | 12/2013 | Geveci et al. |
| 8,618,939 B2 | 12/2013 | Nabata et al. |
| 8,618,942 B1 | 12/2013 | Billman |
| 8,621,849 B2 | 1/2014 | Vernassa et al. |
| 8,621,911 B2 | 1/2014 | McFaul |
| 8,631,690 B2 | 1/2014 | Kowalkowski et al. |
| 8,632,666 B2 | 1/2014 | Schlichte et al. |
| 8,635,900 B2 | 1/2014 | Ante et al. |
| 8,638,215 B2 | 1/2014 | Kates |
| 8,638,453 B2 | 1/2014 | Kessler |
| 8,641,611 B2 | 2/2014 | Urushihata et al. |
| 8,641,878 B2 | 2/2014 | Nemes |
| 8,646,253 B2 | 2/2014 | Gloeckle et al. |
| 8,646,324 B2 | 2/2014 | Plonka et al. |
| 8,646,341 B2 | 2/2014 | Schulten et al. |
| 8,648,731 B2 | 2/2014 | Su et al. |
| 8,649,840 B2 | 2/2014 | Sheppard, Jr. et al. |
| 8,649,961 B2 | 2/2014 | Hawkins et al. |
| 8,650,942 B2 | 2/2014 | Klenk et al. |
| 8,652,040 B2 | 2/2014 | LeBoeuf et al. |
| 8,653,439 B2 | 2/2014 | Nauka et al. |
| 8,659,416 B1 | 2/2014 | Higgins |
| 8,661,791 B2 | 3/2014 | Furness |
| 8,666,588 B2 | 3/2014 | Geilen et al. |
| 8,668,874 B2 | 3/2014 | Tao et al. |
| 8,668,884 B2 | 3/2014 | Kim et al. |
| 8,669,878 B1 | 3/2014 | Vantilburg |
| 8,671,737 B2 | 3/2014 | Brasfield |
| 8,674,813 B2 | 3/2014 | Alexander et al. |
| 8,674,842 B2 | 3/2014 | Zishaan |
| 8,683,786 B2 | 4/2014 | Ruona et al. |
| 8,683,856 B2 | 4/2014 | Kitaura |
| 8,687,188 B2 | 4/2014 | Long et al. |
| 8,689,536 B2 | 4/2014 | Kopacek et al. |
| 8,691,066 B2 | 4/2014 | Collins |
| 8,691,390 B2 | 4/2014 | Ramamurthy |
| 8,694,197 B2 | 4/2014 | Rajagopalan et al. |
| 8,699,029 B2 | 4/2014 | Steel et al. |
| 8,701,463 B2 | 4/2014 | Brasfield |
| 8,702,618 B2 | 4/2014 | MacDonald et al. |
| 8,703,067 B2 | 4/2014 | Woolley |
| 8,704,171 B2 | 4/2014 | Robinson et al. |
| 8,707,677 B2 | 4/2014 | Kowalkowski et al. |
| 8,707,807 B2 | 4/2014 | Yadav et al. |
| 8,709,721 B2 | 4/2014 | Abe et al. |
| 8,715,587 B1 | 5/2014 | Downs |
| 8,716,027 B2 | 5/2014 | Bronchetti |
| 8,720,251 B2 | 5/2014 | Henshaw et al. |
| 8,742,897 B2 | 6/2014 | Jackson |
| 8,742,932 B2 | 6/2014 | Casares |
| 8,745,971 B2 | 6/2014 | Yezerets et al. |
| 8,748,111 B2 | 6/2014 | Mershin et al. |
| 8,749,392 B2 | 6/2014 | Wedig et al. |
| 8,752,368 B2 | 6/2014 | Ante et al. |
| 8,755,942 B2 | 6/2014 | Bonilla et al. |
| 8,759,111 B2 | 6/2014 | Crunaire et al. |
| 8,759,791 B1 | 6/2014 | Hug et al. |
| 8,760,304 B2 | 6/2014 | Pincu |
| 8,760,508 B2 | 6/2014 | Brantley et al. |
| 8,765,481 B2 | 7/2014 | Waldvogel et al. |
| 8,769,928 B2 | 7/2014 | Yeager et al. |
| 8,769,937 B2 | 7/2014 | Yanakiev et al. |
| 8,770,008 B2 | 7/2014 | Carlson et al. |
| 8,770,771 B2 | 7/2014 | Preta et al. |
| 8,771,489 B2 | 7/2014 | Xiao et al. |
| 8,783,019 B2 | 7/2014 | Bedford et al. |
| 8,786,454 B2 | 7/2014 | Siddall |
| 8,791,828 B2 | 7/2014 | Harkins et al. |
| 8,793,849 B1 | 8/2014 | Bhethanabotla et al. |
| 8,794,057 B2 | 8/2014 | Ardanese et al. |
| 8,795,978 B2 | 8/2014 | Steyn et al. |
| 8,803,677 B1 | 8/2014 | Miller |
| 8,803,696 B1 | 8/2014 | Dunyan |
| 8,806,914 B2 | 8/2014 | Brasfield |
| 8,810,426 B1 | 8/2014 | Morris |
| 8,813,546 B2 | 8/2014 | Takahashi et al. |
| 8,818,713 B2 | 8/2014 | Kumar et al. |
| 8,820,051 B2 | 9/2014 | Barasa et al. |
| 8,820,054 B2 | 9/2014 | Bisaiji et al. |
| 8,823,400 B2 | 9/2014 | Hocken et al. |
| 8,826,723 B2 | 9/2014 | Henry |
| 8,826,730 B2 | 9/2014 | Koizumi et al. |
| 8,830,057 B2 | 9/2014 | Poursohi et al. |
| 8,838,396 B2 | 9/2014 | Gentala et al. |
| 8,843,263 B2 | 9/2014 | Willard |
| 8,844,337 B2 | 9/2014 | Kountotsis et al. |
| 8,844,343 B2 | 9/2014 | Kim |
| 8,846,406 B1 | 9/2014 | Martin et al. |
| 8,847,773 B2 | 9/2014 | Rauworth et al. |
| 8,852,513 B1 | 10/2014 | Speer et al. |

(56) References Cited

U.S. PATENT DOCUMENTS

| | | |
|---|---|---|
| 8,852,945 B2 | 10/2014 | Lee et al. |
| 8,852,946 B2 | 10/2014 | Lee et al. |
| 8,854,362 B1 | 10/2014 | Poursohi et al. |
| 8,857,463 B1 | 10/2014 | Carruth et al. |
| 8,857,662 B2 | 10/2014 | Hoppe et al. |
| 8,859,995 B2 | 10/2014 | Liu et al. |
| 8,863,497 B1 | 10/2014 | Legare |
| 8,863,499 B2 | 10/2014 | Kowalkowski et al. |
| 8,868,378 B2 | 10/2014 | Batzler et al. |
| 8,869,607 B2 | 10/2014 | Levijoki et al. |
| 8,871,148 B2 | 10/2014 | Wendland et al. |
| 8,881,508 B2 | 11/2014 | Geveci |
| 8,884,751 B2 | 11/2014 | Baldocchi et al. |
| 8,887,490 B2 | 11/2014 | Wentz et al. |
| 8,888,979 B2 | 11/2014 | Nemes |
| 8,890,701 B2 | 11/2014 | Mahajan et al. |
| 8,893,475 B2 | 11/2014 | Geveci et al. |
| 8,899,098 B2 | 12/2014 | Senft et al. |
| 8,907,803 B2 | 12/2014 | Martin |
| 8,910,466 B2 | 12/2014 | Kowalkowski et al. |
| 8,910,508 B2 | 12/2014 | Liwa |
| 8,912,003 B2 | 12/2014 | Monk |
| 8,912,909 B2 | 12/2014 | Al-Ali et al. |
| 8,914,221 B2 | 12/2014 | Peters et al. |
| 8,915,022 B2 | 12/2014 | Klink et al. |
| 8,915,645 B2 | 12/2014 | Genssle et al. |
| 8,916,037 B1 | 12/2014 | Mayer et al. |
| 8,917,078 B2 | 12/2014 | Kondo et al. |
| 8,917,186 B1 | 12/2014 | Grant |
| 8,920,627 B2 | 12/2014 | Fleischer et al. |
| 8,922,219 B2 | 12/2014 | Li et al. |
| 8,922,335 B2 | 12/2014 | Deweese et al. |
| 8,924,131 B2 | 12/2014 | Kowalkowski et al. |
| 8,928,338 B2 | 1/2015 | Nelson et al. |
| 8,930,121 B2 | 1/2015 | Rajagopalan et al. |
| 8,931,327 B2 | 1/2015 | Pearce et al. |
| 8,931,712 B2 | 1/2015 | Nagano et al. |
| 8,932,533 B2 | 1/2015 | Kruglick |
| 8,935,084 B2 | 1/2015 | Lin et al. |
| 8,947,230 B1 | 2/2015 | Gettings et al. |
| 8,947,249 B1 | 2/2015 | Dore et al. |
| 8,950,238 B2 | 2/2015 | Shaw et al. |
| 8,951,396 B2 | 2/2015 | Nemes |
| 8,951,503 B2 | 2/2015 | Singaram et al. |
| 8,955,307 B2 | 2/2015 | Yahata et al. |
| 8,955,515 B2 | 2/2015 | Rakow et al. |
| 8,955,765 B2 | 2/2015 | Porchia et al. |
| 8,956,571 B2 | 2/2015 | Goldstein et al. |
| 8,959,904 B2 | 2/2015 | Porras et al. |
| 8,959,982 B2 | 2/2015 | Pearce et al. |
| 8,962,334 B2 | 2/2015 | Lee et al. |
| 8,963,730 B1 | 2/2015 | Dickerman |
| 8,966,882 B2 | 3/2015 | Tylutki et al. |
| 8,968,646 B2 | 3/2015 | Matheis et al. |
| 8,969,069 B2 | 3/2015 | Ahn et al. |
| 8,969,083 B2 | 3/2015 | Lee et al. |
| 8,969,084 B2 | 3/2015 | Lee et al. |
| 8,969,096 B2 | 3/2015 | Hicks et al. |
| 8,970,383 B2 | 3/2015 | Liou et al. |
| 8,973,430 B2 | 3/2015 | Nagaoka et al. |
| 8,981,498 B2 | 3/2015 | Ziglioli |
| 8,984,867 B2 | 3/2015 | Anilovich et al. |
| 8,986,998 B2 | 3/2015 | Lee et al. |
| 8,992,770 B2 | 3/2015 | Gong et al. |
| 8,997,726 B2 | 4/2015 | Eser et al. |
| 9,007,222 B2 | 4/2015 | Mittleman et al. |
| 9,007,224 B1 | 4/2015 | Fadell et al. |
| 9,010,087 B1 | 4/2015 | Upadhyay et al. |
| 9,010,172 B2 | 4/2015 | Xia et al. |
| 9,012,169 B2 | 4/2015 | Schilling |
| 9,013,297 B1 | 4/2015 | Dey et al. |
| 9,014,859 B2 | 4/2015 | Isaksson et al. |
| 9,018,016 B2 | 4/2015 | Crunaire et al. |
| 9,019,109 B2 | 4/2015 | Warmack et al. |
| 9,019,111 B1 | 4/2015 | Sloo et al. |
| 9,020,764 B2 | 4/2015 | Walte et al. |
| 9,021,789 B2 | 5/2015 | Sawada et al. |
| 9,021,860 B2 | 5/2015 | Nelson |
| 9,026,386 B2 | 5/2015 | Jiang |
| 9,027,539 B2 | 5/2015 | Miyashita |
| 9,028,570 B2 | 5/2015 | Suematsu et al. |
| 9,028,615 B2 | 5/2015 | Eglmeier et al. |
| 9,028,751 B2 | 5/2015 | Page et al. |
| 9,030,319 B1 | 5/2015 | Haynes |
| 9,030,329 B2 | 5/2015 | Rutherford et al. |
| 9,030,330 B1 | 5/2015 | Nichols, Jr. |
| 9,033,553 B2 | 5/2015 | Li |
| 9,038,369 B2 | 5/2015 | Khaled et al. |
| 9,046,021 B2 | 6/2015 | DeGeorge |
| 9,047,754 B2 | 6/2015 | Kim |
| 9,050,561 B1 | 6/2015 | Shetney et al. |
| 9,051,866 B2 | 6/2015 | Yanakiev et al. |
| 9,051,867 B2 | 6/2015 | Fontana |
| 9,051,868 B2 | 6/2015 | Scherer et al. |
| 9,052,280 B2 | 6/2015 | Katsurahara et al. |
| 9,053,626 B2 | 6/2015 | Cristoforo |
| 9,057,338 B2 | 6/2015 | Levijoki et al. |
| 9,057,669 B2 | 6/2015 | van Straaten et al. |
| 9,062,623 B2 | 6/2015 | Verdier et al. |
| 9,062,637 B2 | 6/2015 | Sager et al. |
| 9,068,226 B2 | 6/2015 | Matsunami et al. |
| 9,068,491 B2 | 6/2015 | Cavataio et al. |
| 9,068,493 B2 | 6/2015 | Tanioka |
| 9,068,937 B2 | 6/2015 | Kilinc et al. |
| 9,070,272 B2 | 6/2015 | Gettings et al. |
| 9,074,045 B2 | 7/2015 | Fernandez et al. |
| 9,074,507 B2 | 7/2015 | Tylutki et al. |
| 9,074,539 B2 | 7/2015 | Yahata et al. |
| 9,080,782 B1 | 7/2015 | Sheikh |
| 9,082,274 B2 | 7/2015 | Goto et al. |
| 9,082,275 B2 | 7/2015 | Baker |
| 9,086,391 B2 | 7/2015 | Lee et al. |
| 9,091,226 B2 | 7/2015 | Zimmerschied et al. |
| 9,097,165 B2 | 8/2015 | Kim |
| 9,100,368 B2 | 8/2015 | Rezvani et al. |
| 9,102,417 B1 | 8/2015 | Young |
| 9,103,775 B2 | 8/2015 | Bradley et al. |
| 9,103,796 B2 | 8/2015 | Song |
| 9,104,538 B2 | 8/2015 | Garrett et al. |
| 9,109,480 B2 | 8/2015 | Kowalkowski et al. |
| 9,109,481 B2 | 8/2015 | Martin et al. |
| 9,109,493 B2 | 8/2015 | Lin et al. |
| 9,109,527 B2 | 8/2015 | Barnikow et al. |
| 9,110,007 B2 | 8/2015 | Birecki et al. |
| 9,110,041 B2 | 8/2015 | Flanders |
| 9,111,426 B2 | 8/2015 | Engelmann et al. |
| 9,113,052 B1 | 8/2015 | Scalisi et al. |
| 9,113,836 B2 | 8/2015 | Bernstein et al. |
| 9,115,629 B2 | 8/2015 | Hopka et al. |
| 9,115,630 B1 | 8/2015 | Geveci et al. |
| 9,121,323 B2 | 9/2015 | Feldmann et al. |
| 9,123,244 B2 | 9/2015 | Daman et al. |
| 9,124,955 B2 | 9/2015 | Geva et al. |
| 9,125,255 B2 | 9/2015 | Ramer et al. |
| 9,125,590 B2 | 9/2015 | Tang et al. |
| 9,125,607 B2 | 9/2015 | Wang et al. |
| 9,125,625 B2 | 9/2015 | Wang et al. |
| 9,127,301 B2 | 9/2015 | Krebs et al. |
| 9,128,139 B2 | 9/2015 | Carbonaro et al. |
| 9,129,496 B1 | 9/2015 | Jackson |
| 9,135,794 B1 | 9/2015 | Anderson et al. |
| 9,137,108 B2 | 9/2015 | Rezvani et al. |
| 9,138,524 B2 | 9/2015 | Bluchel et al. |
| 9,140,677 B2 | 9/2015 | Mershin et al. |
| 9,142,118 B2 | 9/2015 | Patenaude et al. |
| 9,142,119 B1 | 9/2015 | Grant |
| 9,144,396 B2 | 9/2015 | Choe et al. |
| 9,144,772 B2 | 9/2015 | Pfister et al. |
| 9,145,842 B2 | 9/2015 | Takahashi et al. |
| 9,145,851 B2 | 9/2015 | Bossmeyer et al. |
| 9,146,222 B2 | 9/2015 | Su et al. |
| 9,147,329 B2 | 9/2015 | Bugg, Jr. |
| 9,151,729 B2 | 10/2015 | Rabbett |
| 9,151,767 B2 | 10/2015 | Yang |

(56) References Cited

U.S. PATENT DOCUMENTS

| | | |
|---|---|---|
| 9,153,107 B2 | 10/2015 | Austin |
| 9,157,390 B2 | 10/2015 | Song et al. |
| 9,159,218 B2 | 10/2015 | Simoncic et al. |
| 9,160,987 B1 | 10/2015 | Kasmir et al. |
| 9,163,575 B2 | 10/2015 | Pursifull |
| 9,164,071 B2 | 10/2015 | McFaul |
| 9,167,100 B2 | 10/2015 | Bang |
| 9,169,795 B2 | 10/2015 | Jammoussi et al. |
| 9,170,144 B2 | 10/2015 | Qi |
| 9,170,228 B2 | 10/2015 | Takulapalli |
| 9,170,229 B2 | 10/2015 | Paggel et al. |
| 9,170,243 B2 | 10/2015 | Yabuki et al. |
| 9,170,258 B2 | 10/2015 | Withrow, III et al. |
| 9,171,453 B2 | 10/2015 | Warmack et al. |
| 9,172,606 B2 | 10/2015 | Rezvani et al. |
| 9,172,742 B2 | 10/2015 | Rezvani et al. |
| RE45,804 E | 11/2015 | Mancini |
| 9,175,415 B2 | 11/2015 | Hong et al. |
| 9,175,625 B2 | 11/2015 | Kumar et al. |
| 9,179,220 B2 | 11/2015 | Morris |
| 9,181,843 B2 | 11/2015 | Kim et al. |
| 9,181,878 B2 | 11/2015 | Moeckly et al. |
| 9,182,366 B2 | 11/2015 | Izawa et al. |
| 9,183,731 B1 | 11/2015 | Bokhary |
| 9,183,733 B2 | 11/2015 | Kates |
| 9,183,736 B2 | 11/2015 | Sloo et al. |
| 9,183,737 B1 | 11/2015 | Billman |
| 9,186,090 B2 | 11/2015 | Chu et al. |
| 9,188,073 B2 | 11/2015 | Chen et al. |
| 9,188,075 B2 | 11/2015 | Varney |
| 9,188,568 B2 | 11/2015 | Ebeler et al. |
| 9,191,277 B2 | 11/2015 | Rezvani et al. |
| 9,191,909 B2 | 11/2015 | Rezvani et al. |
| 9,194,268 B2 | 11/2015 | Kowalkowski et al. |
| 9,194,273 B2 | 11/2015 | Janssen et al. |
| 9,194,358 B1 | 11/2015 | Avramidis |
| 9,194,807 B2 | 11/2015 | Song |
| 9,196,146 B1 | 11/2015 | Vicente |
| 9,202,363 B1 | 12/2015 | Grant |
| 9,203,695 B2 | 12/2015 | Rezvani et al. |
| 9,206,727 B2 | 12/2015 | Liu et al. |
| 9,208,676 B2 | 12/2015 | Fadell et al. |
| 9,211,356 B2 | 12/2015 | Gruenbacher et al. |
| 9,212,610 B2 | 12/2015 | Chen et al. |
| 9,217,737 B2 | 12/2015 | Boyd et al. |
| 9,224,278 B2 | 12/2015 | Bernal et al. |
| 9,226,481 B1 | 1/2016 | Paripati |
| 9,228,523 B2 | 1/2016 | Varney |
| 9,228,923 B2 | 1/2016 | Zimmerman et al. |
| 9,230,371 B2 | 1/2016 | Jecks et al. |
| 9,233,082 B2 | 1/2016 | Kato et al. |
| 9,234,871 B2 | 1/2016 | Fleischer et al. |
| 9,235,976 B2 | 1/2016 | Sloo et al. |
| 9,244,474 B2 | 1/2016 | Smith et al. |
| 9,247,215 B1 | 1/2016 | Athan |
| 9,248,707 B2 | 2/2016 | Zhou et al. |
| 9,249,453 B2 | 2/2016 | Kato et al. |
| 9,249,737 B2 | 2/2016 | Fitzgerald et al. |
| 9,250,222 B2 | 2/2016 | Furton et al. |
| 9,250,667 B2 | 2/2016 | Liwa |
| 9,251,687 B2 | 2/2016 | Thompson et al. |
| 9,251,696 B2 | 2/2016 | Sloo et al. |
| 9,255,435 B2 | 2/2016 | Weidenbacher |
| 9,255,536 B2 | 2/2016 | Eser et al. |
| 9,255,873 B2 | 2/2016 | Sakamoto et al. |
| 9,259,498 B2 | 2/2016 | Shen |
| 9,260,738 B2 | 2/2016 | Moularat et al. |
| 9,261,006 B2 | 2/2016 | Mitchell et al. |
| 9,261,033 B2 | 2/2016 | Sealy et al. |
| 9,261,481 B2 | 2/2016 | Mintah et al. |
| 9,261,885 B2 | 2/2016 | Tryfonos et al. |
| 9,262,901 B1 | 2/2016 | Mona |
| 9,262,902 B2 | 2/2016 | Costa |
| 9,262,906 B2 | 2/2016 | Poder et al. |
| 9,262,909 B1 | 2/2016 | Grant |
| 9,265,235 B2 | 2/2016 | Inoue et al. |
| 9,266,072 B2 | 2/2016 | Ingledew et al. |
| 9,267,866 B2 | 2/2016 | Almirall et al. |
| 9,273,587 B2 | 3/2016 | Khaled et al. |
| 9,279,382 B2 | 3/2016 | Genko |
| 9,279,791 B2 | 3/2016 | Fukui et al. |
| 9,280,884 B1 | 3/2016 | Schultz et al. |
| 9,291,610 B2 | 3/2016 | Zelepouga et al. |
| 9,296,390 B2 | 3/2016 | Martin et al. |
| 9,297,286 B2 | 3/2016 | Kruer et al. |
| 9,297,843 B2 | 3/2016 | Gibson et al. |
| 9,310,347 B2 | 4/2016 | Xu et al. |
| 9,310,781 B2 | 4/2016 | Lee et al. |
| 9,311,807 B2 | 4/2016 | Schultz et al. |
| 9,311,811 B1 | 4/2016 | Szewczyk et al. |
| 9,313,761 B2 | 4/2016 | Rezvani et al. |
| 9,315,848 B2 | 4/2016 | Haick et al. |
| 9,315,852 B2 | 4/2016 | Swartz |
| 9,316,565 B2 | 4/2016 | Kappaganthu et al. |
| 9,316,574 B2 | 4/2016 | Sakamoto et al. |
| 9,316,626 B2 | 4/2016 | Reinhardt et al. |
| 9,318,015 B2 | 4/2016 | Kates |
| 9,327,148 B2 | 5/2016 | Holoch et al. |
| 9,328,645 B2 | 5/2016 | Tylutki et al. |
| 9,329,191 B2 | 5/2016 | Chang et al. |
| 9,330,550 B2 | 5/2016 | Zribi et al. |
| 9,332,057 B2 | 5/2016 | Rezvani et al. |
| 9,332,322 B2 | 5/2016 | Niemeyer et al. |
| 9,335,310 B2 | 5/2016 | Lee et al. |
| 9,347,356 B2 | 5/2016 | Qi |
| 9,347,678 B2 | 5/2016 | Stakutis et al. |
| 9,347,916 B2 | 5/2016 | Moularat et al. |
| 9,351,675 B2 | 5/2016 | Al-Ali et al. |
| 9,352,065 B2 | 5/2016 | Habbel |
| 9,353,966 B2 | 5/2016 | Finkam |
| 9,356,215 B2 | 5/2016 | Iriyama |
| 9,357,490 B2 | 5/2016 | Kates |
| 9,360,181 B2 | 6/2016 | Li |
| 9,360,394 B2 | 6/2016 | Walter et al. |
| 9,366,192 B2 | 6/2016 | Byrd et al. |
| 9,371,972 B2 | 6/2016 | Li |
| 9,376,435 B2 | 6/2016 | George et al. |
| 9,376,952 B2 | 6/2016 | Kowalkowski et al. |
| 9,376,976 B2 | 6/2016 | Baumann et al. |
| 9,376,991 B2 | 6/2016 | Dudar et al. |
| 9,377,447 B2 | 6/2016 | Mershin et al. |
| 9,382,861 B2 | 7/2016 | Jankovic et al. |
| 9,388,728 B2 | 7/2016 | Chandrasekaran et al. |
| 9,390,565 B2 | 7/2016 | Thompson et al. |
| 9,395,324 B2 | 7/2016 | Zribi et al. |
| 9,396,623 B2 | 7/2016 | Lasker |
| 9,399,912 B2 | 7/2016 | McAlary et al. |
| 9,399,958 B2 | 7/2016 | Sano et al. |
| 9,399,961 B2 | 7/2016 | Lehmen et al. |
| 9,401,950 B2 | 7/2016 | Rezvani et al. |
| 9,404,832 B2 | 8/2016 | Kimura et al. |
| 9,407,684 B2 | 8/2016 | Rezvani et al. |
| 9,407,685 B2 | 8/2016 | Rezvani et al. |
| 9,408,556 B2 | 8/2016 | Wang et al. |
| 9,410,896 B2 | 8/2016 | Sajdak et al. |
| 9,412,258 B2 | 8/2016 | Matsuoka et al. |
| 9,412,260 B2 | 8/2016 | Kates |
| 9,413,810 B2 | 8/2016 | Rezvani et al. |
| 9,415,345 B2 | 8/2016 | Holbert et al. |
| 9,416,708 B2 | 8/2016 | Schroeder et al. |
| 9,416,735 B2 | 8/2016 | Varney |
| 9,416,755 B2 | 8/2016 | Dudar |
| 9,417,226 B2 | 8/2016 | Amisar |
| 9,418,828 B2 | 8/2016 | Mennito et al. |
| 9,421,294 B2 | 8/2016 | Yamada et al. |
| 9,422,847 B2 | 8/2016 | Osburn et al. |
| 9,429,062 B2 | 8/2016 | Osburn et al. |
| 9,429,090 B2 | 8/2016 | Kennie et al. |
| 9,429,537 B2 | 8/2016 | Kang et al. |
| 9,429,551 B2 | 8/2016 | Podgorney |
| 9,430,927 B2 | 8/2016 | Yu et al. |
| 9,430,933 B2 | 8/2016 | Fadell et al. |
| 9,437,092 B2 | 9/2016 | Warmack et al. |
| 9,437,097 B2 | 9/2016 | Poursohi et al. |

(56) References Cited

U.S. PATENT DOCUMENTS

| | | |
|---|---|---|
| 9,441,564 B2 | 9/2016 | Surnilla et al. |
| 9,442,073 B2 | 9/2016 | Joly et al. |
| 9,444,244 B2 | 9/2016 | Hooper et al. |
| 9,448,218 B2 | 9/2016 | Lee et al. |
| 9,449,491 B2 | 9/2016 | Sager et al. |
| 9,449,492 B2 | 9/2016 | Dixon et al. |
| 9,453,450 B2 | 9/2016 | Sun et al. |
| 9,453,451 B2 | 9/2016 | Matsumoto et al. |
| 9,453,472 B2 | 9/2016 | Levijoki et al. |
| 9,458,776 B2 | 10/2016 | Haehara et al. |
| 9,459,235 B2 | 10/2016 | Soundarrajan et al. |
| 9,460,595 B2 | 10/2016 | Chen |
| 9,460,596 B1 | 10/2016 | Moses |
| 9,460,611 B2 | 10/2016 | Emerson et al. |
| 9,466,194 B1 | 10/2016 | Kraz et al. |
| 9,470,168 B2 | 10/2016 | Yoon |
| 9,472,070 B2 | 10/2016 | Chen |
| 9,472,092 B1 | 10/2016 | Grant |
| 9,473,559 B2 | 10/2016 | Rezvani et al. |
| 9,474,023 B1 | 10/2016 | Kates |
| 9,474,824 B2 | 10/2016 | Conroy et al. |
| 9,476,341 B2 | 10/2016 | Whitt et al. |
| 9,476,387 B2 | 10/2016 | Kim et al. |
| 9,476,862 B2 | 10/2016 | Motayed et al. |
| 9,482,124 B2 | 11/2016 | Dong et al. |
| 9,482,136 B2 | 11/2016 | Ancimer et al. |
| 9,482,137 B2 | 11/2016 | Liu et al. |
| 9,482,172 B2 | 11/2016 | Pursifull et al. |
| 9,489,807 B2 | 11/2016 | Morris |
| 9,489,829 B2 | 11/2016 | Sloo et al. |
| 9,491,224 B2 | 11/2016 | Rezvani et al. |
| 9,492,788 B2 | 11/2016 | Gaudin |
| 9,495,853 B2 | 11/2016 | Jackson |
| 9,499,572 B2 | 11/2016 | Wensbo Posaric et al. |
| 9,499,584 B2 | 11/2016 | Paz Rojas et al. |
| 9,500,580 B1 | 11/2016 | Mitra et al. |
| 9,501,452 B2 | 11/2016 | Kowalkowski et al. |
| 9,503,539 B1 | 11/2016 | Trundle et al. |
| 9,506,414 B2 | 11/2016 | Melby et al. |
| 9,506,649 B2 | 11/2016 | Rennie et al. |
| 9,506,863 B2 | 11/2016 | Hicks et al. |
| 9,506,901 B2 | 11/2016 | Lewis |
| 9,509,754 B2 | 11/2016 | Rezvani et al. |
| 9,513,007 B2 | 12/2016 | Kuchta |
| 9,513,191 B2 | 12/2016 | Schankula et al. |
| 9,513,210 B2 | 12/2016 | Kharrat et al. |
| 9,513,898 B2 | 12/2016 | Solnit et al. |
| 9,514,631 B2 | 12/2016 | Matsuoka et al. |
| 9,518,710 B2 | 12/2016 | Li |
| 9,518,960 B2 | 12/2016 | Nema et al. |
| 9,520,042 B2 | 12/2016 | Eck |
| 9,520,046 B2 | 12/2016 | Call et al. |
| 9,520,054 B2 | 12/2016 | Rossi et al. |
| 9,522,209 B2 | 12/2016 | Meier et al. |
| 9,522,210 B2 | 12/2016 | Worrilow |
| 9,527,498 B2 | 12/2016 | Martin et al. |
| 9,528,422 B2 | 12/2016 | Li et al. |
| 9,528,424 B2 | 12/2016 | Aoki et al. |
| 9,528,462 B2 | 12/2016 | Ardanese et al. |
| 9,528,473 B2 | 12/2016 | Dudar et al. |
| 9,528,476 B2 | 12/2016 | Surnilla et al. |
| 9,528,979 B2 | 12/2016 | Haick et al. |
| 9,530,305 B2 | 12/2016 | Burnette et al. |
| 9,534,524 B1 | 1/2017 | Hopka et al. |
| 9,534,553 B2 | 1/2017 | Chamarthi et al. |
| 9,534,984 B2 | 1/2017 | Glugla et al. |
| 9,537,670 B2 | 1/2017 | Cho et al. |
| 9,540,589 B2 | 1/2017 | Angel et al. |
| 9,541,040 B2 | 1/2017 | Karunaratne et al. |
| 9,547,968 B2 | 1/2017 | Adams et al. |
| 9,551,260 B2 | 1/2017 | Kakimoto |
| 9,551,701 B2 | 1/2017 | Marchand et al. |
| 9,552,705 B2 | 1/2017 | Morris |
| 9,552,718 B2 | 1/2017 | Fadell et al. |
| 9,552,720 B2 | 1/2017 | Moffa |
| 9,553,971 B2 | 1/2017 | Calabrese et al. |
| 9,556,469 B2 | 1/2017 | Marcoux et al. |
| 9,556,812 B2 | 1/2017 | Ozkan |
| 9,560,712 B2 | 1/2017 | Chen |
| 9,562,470 B2 | 2/2017 | Younkins et al. |
| 9,562,841 B2 | 2/2017 | Tylutki et al. |
| 9,562,882 B2 | 2/2017 | Crunaire et al. |
| 9,565,657 B2 | 2/2017 | Suresh et al. |
| 9,568,456 B2 | 2/2017 | Yi et al. |
| 9,568,902 B2 | 2/2017 | Dunn et al. |
| 9,569,945 B2 | 2/2017 | Zumsteg et al. |
| 9,574,480 B2 | 2/2017 | Matsumoto et al. |
| 9,574,763 B2 | 2/2017 | Chen |
| 9,574,971 B2 | 2/2017 | McKay et al. |
| 9,575,038 B2 | 2/2017 | Furton et al. |
| 9,575,042 B2 | 2/2017 | Okrut et al. |
| 9,576,457 B1 | 2/2017 | Mona |
| 9,576,458 B2 | 2/2017 | Calvert |
| 9,576,466 B2 | 2/2017 | Sager et al. |
| 9,581,098 B2 | 2/2017 | Chen et al. |
| 9,581,099 B1 | 2/2017 | Szailer et al. |
| 9,581,561 B2 | 2/2017 | Tao et al. |
| 9,581,574 B2 | 2/2017 | Murphy |
| 9,581,575 B2 | 2/2017 | Batayneh et al. |
| 9,588,084 B2 | 3/2017 | Delapierre et al. |
| 9,589,440 B2 | 3/2017 | Pan et al. |
| 9,589,441 B2 | 3/2017 | Shapiro et al. |
| 9,593,617 B2 | 3/2017 | Veldten et al. |
| 9,594,006 B2 | 3/2017 | Harner |
| 9,598,848 B2 | 3/2017 | Seibt et al. |
| 9,599,004 B2 | 3/2017 | Takaoka |
| 9,599,005 B2 | 3/2017 | Khaled et al. |
| 9,600,998 B2 | 3/2017 | Mumey |
| 9,601,001 B2 | 3/2017 | Matsuoka et al. |
| 9,605,578 B1 | 3/2017 | Qi |
| 9,606,040 B2 | 3/2017 | Sakamoto et al. |
| 9,606,092 B2 | 3/2017 | Brahma |
| 9,607,494 B2 | 3/2017 | Pattok et al. |
| 9,609,399 B2 | 3/2017 | Krishnamurthy et al. |
| 9,611,308 B2 | 4/2017 | Matsunami et al. |
| 9,611,813 B2 | 4/2017 | Dudar |
| 9,612,174 B2 | 4/2017 | Peters et al. |
| 9,612,602 B2 | 4/2017 | Smith et al. |
| 9,613,516 B2 | 4/2017 | Glasgow et al. |
| 9,615,066 B1 | 4/2017 | Tran et al. |
| 9,617,899 B2 | 4/2017 | Goodwin |
| 9,617,940 B2 | 4/2017 | Klingbeil et al. |
| 9,624,525 B2 | 4/2017 | Fallon |
| 9,624,804 B2 | 4/2017 | Matsumoto et al. |
| 9,624,808 B2 | 4/2017 | Miyamoto et al. |
| 9,625,112 B2 | 4/2017 | Li |
| 9,625,374 B2 | 4/2017 | Chang et al. |
| 9,625,432 B2 | 4/2017 | Villarreal Guerra et al. |
| 9,626,858 B2 | 4/2017 | Sloo et al. |
| 9,631,585 B2 | 4/2017 | Lombardo et al. |
| 9,633,547 B2 | 4/2017 | Farrand et al. |
| 9,633,551 B2 | 4/2017 | Aljadeff et al. |
| 9,638,122 B2 | 5/2017 | Smith et al. |
| 9,642,340 B2 | 5/2017 | Brown, Jr. et al. |
| 9,644,974 B2 | 5/2017 | Plocher et al. |
| 9,645,068 B2 | 5/2017 | Zhang |
| 9,645,126 B2 | 5/2017 | Dufour et al. |
| 9,645,127 B2 | 5/2017 | Amin et al. |
| 9,646,476 B1 | 5/2017 | Hansen |
| 9,648,082 B2 | 5/2017 | Rezvani et al. |
| 9,650,981 B1 | 5/2017 | Large et al. |
| 9,652,976 B2 | 5/2017 | Bruck et al. |
| 9,657,326 B2 | 5/2017 | Ruether et al. |
| 9,657,627 B2 | 5/2017 | Kogo et al. |
| 9,657,630 B2 | 5/2017 | Perrin et al. |
| 9,662,626 B2 | 5/2017 | Yates et al. |
| 9,664,089 B2 | 5/2017 | Kim et al. |
| 9,664,095 B2 | 5/2017 | Van Nieuwstadt et al. |
| 9,664,569 B2 | 5/2017 | Mittleman et al. |
| 9,664,570 B2 | 5/2017 | Ademe et al. |
| 9,666,006 B2 | 5/2017 | Kramer et al. |
| 9,667,907 B2 | 5/2017 | Diaz |
| 9,670,817 B2 | 6/2017 | Yoo et al. |
| 9,670,861 B2 | 6/2017 | Jankovic et al. |

(56) References Cited

U.S. PATENT DOCUMENTS

| | | |
|---|---|---|
| 9,671,380 B2 | 6/2017 | Weber et al. |
| 9,677,327 B1 | 6/2017 | Nagel et al. |
| 9,677,450 B2 | 6/2017 | Lauer et al. |
| 9,677,452 B2 | 6/2017 | Kogo et al. |
| 9,677,488 B2 | 6/2017 | Nilsson |
| 9,677,491 B2 | 6/2017 | Jammoussi et al. |
| 9,678,059 B2 | 6/2017 | Haick et al. |
| 9,683,507 B2 | 6/2017 | Yezerets et al. |
| 9,683,535 B2 | 6/2017 | Glugla et al. |
| 9,685,054 B2 | 6/2017 | Simmons |
| 9,689,335 B2 | 6/2017 | Ge |
| 9,689,542 B2 | 6/2017 | Anderson et al. |
| 9,689,826 B2 | 6/2017 | Haick et al. |
| 9,689,853 B2 | 6/2017 | Mittleman et al. |
| 9,691,254 B2 | 6/2017 | Jeong |
| 9,691,256 B2 | 6/2017 | Wu et al. |
| 9,691,257 B2 | 6/2017 | Matsuoka et al. |
| 9,691,261 B2 | 6/2017 | Tuck et al. |
| 9,693,512 B2 | 7/2017 | Chen et al. |
| 9,696,291 B2 | 7/2017 | Gailius et al. |
| 9,696,311 B2 | 7/2017 | Haick et al. |
| 9,697,713 B2 | 7/2017 | Fadell et al. |
| 9,701,243 B1 | 7/2017 | Phatak et al. |
| 9,702,293 B2 | 7/2017 | Fujie et al. |
| 9,702,315 B1 | 7/2017 | Palmer |
| 9,702,566 B2 | 7/2017 | Robison et al. |
| 9,704,095 B2 | 7/2017 | Jacquot et al. |
| 9,704,380 B2 | 7/2017 | Matsuoka et al. |
| 9,708,952 B2 | 7/2017 | Akiyoshi |
| 9,708,953 B1 | 7/2017 | Szailer et al. |
| 9,708,960 B2 | 7/2017 | Hall et al. |
| 9,709,540 B2 | 7/2017 | Lee et al. |
| 9,709,543 B2 | 7/2017 | Sun et al. |
| 9,709,544 B2 | 7/2017 | Kozlow et al. |
| 9,710,001 B2 | 7/2017 | Smith et al. |
| 9,714,614 B2 | 7/2017 | Luehrsen et al. |
| 9,714,941 B2 | 7/2017 | Zhang et al. |
| 9,715,818 B2 | 7/2017 | Poder et al. |
| 9,717,357 B2 | 8/2017 | Johnson et al. |
| 9,717,815 B2 | 8/2017 | Peterson et al. |
| 9,719,449 B2 | 8/2017 | Miyamoto et al. |
| 9,721,456 B2 | 8/2017 | Thurlow et al. |
| 9,721,457 B2 | 8/2017 | Thompson et al. |
| 9,726,633 B2 | 8/2017 | Mett et al. |
| 9,728,082 B2 | 8/2017 | Fox |
| 9,729,945 B2 | 8/2017 | Schultz et al. |
| 9,732,690 B2 | 8/2017 | Rollinger et al. |
| 9,733,155 B2 | 8/2017 | Monros |
| 9,733,225 B2 | 8/2017 | Armstrong |
| 9,737,627 B2 | 8/2017 | Turner et al. |
| 9,739,248 B2 | 8/2017 | Dudar et al. |
| 9,739,709 B2 | 8/2017 | Lear et al. |
| 9,739,761 B2 | 8/2017 | Smith et al. |
| 9,740,822 B2 | 8/2017 | Jackson |
| 9,746,154 B2 | 8/2017 | Dong et al. |
| 9,746,439 B2 | 8/2017 | Porro et al. |
| 9,747,637 B1 | 8/2017 | Kalaboukis et al. |
| 9,747,763 B1 | 8/2017 | Scordato et al. |
| 9,752,488 B2 | 9/2017 | Zambrano et al. |
| 9,752,740 B1 | 9/2017 | Li |
| 9,752,785 B2 | 9/2017 | Corleoni |
| 9,754,466 B2 | 9/2017 | Simmons |
| 9,756,169 B2 | 9/2017 | Mehta et al. |
| 9,758,016 B1 | 9/2017 | Baron et al. |
| 9,759,688 B2 | 9/2017 | Naishadham et al. |
| 9,760,853 B2 | 9/2017 | Rose |
| 9,761,096 B2 | 9/2017 | McMahan et al. |
| 9,761,124 B2 | 9/2017 | Matsuoka et al. |
| 9,763,426 B2 | 9/2017 | Pearce et al. |
| 9,764,623 B2 | 9/2017 | Fruehsorger et al. |
| 9,764,893 B1 | 9/2017 | Westmoreland, III |
| 9,765,668 B2 | 9/2017 | Maus et al. |
| 9,765,715 B2 | 9/2017 | Hohner et al. |
| 9,766,215 B2 | 9/2017 | Hassan et al. |
| 9,767,674 B2 | 9/2017 | Matsuoka et al. |
| 9,767,679 B2 | 9/2017 | Piccolo, III et al. |
| 9,769,420 B1 | 9/2017 | Moses |
| 9,776,725 B2 | 10/2017 | Fox et al. |
| 9,777,659 B2 | 10/2017 | Aoyagi |
| 9,777,697 B2 | 10/2017 | Glugla et al. |
| 9,778,173 B2 | 10/2017 | Chang et al. |
| 9,779,615 B2 | 10/2017 | Davell et al. |
| 9,782,744 B2 | 10/2017 | Warner et al. |
| 9,784,166 B2 | 10/2017 | Osburn et al. |
| 9,784,701 B2 | 10/2017 | Wensbo Posaric et al. |
| 9,784,721 B2 | 10/2017 | Yacoub |
| 9,786,158 B2 | 10/2017 | Beaver et al. |
| 9,790,878 B2 | 10/2017 | Kumar et al. |
| 9,791,425 B2 | 10/2017 | Stollings |
| 9,792,794 B2 | 10/2017 | Morris |
| 9,792,795 B2 | 10/2017 | Warmack et al. |
| 9,796,371 B2 | 10/2017 | Soifer |
| 9,797,344 B2 | 10/2017 | Jeffrey |
| 9,798,309 B2 | 10/2017 | Tirpak |
| 9,798,979 B2 | 10/2017 | Fadell et al. |
| 9,799,175 B2 | 10/2017 | Stagg |
| 9,803,909 B2 | 10/2017 | Son et al. |
| 9,808,021 B2 | 11/2017 | Johnson et al. |
| 9,808,812 B2 | 11/2017 | Gruenbacher et al. |
| 9,810,674 B2 | 11/2017 | Mikami et al. |
| 9,811,994 B1 | 11/2017 | Salzer |
| 9,812,001 B1 | 11/2017 | Grant |
| 9,816,415 B2 | 11/2017 | Hokuto |
| 9,817,492 B2 | 11/2017 | Park |
| 9,819,910 B2 | 11/2017 | Huang et al. |
| 9,819,911 B2 | 11/2017 | K V et al. |
| 9,821,082 B1 | 11/2017 | Swartz et al. |
| 9,823,236 B2 | 11/2017 | Hao et al. |
| 9,824,399 B2 | 11/2017 | Bernard et al. |
| 9,824,565 B1 | 11/2017 | Patel |
| 9,827,342 B2 | 11/2017 | Morgan et al. |
| 9,827,343 B2 | 11/2017 | Lima et al. |
| 9,829,473 B2 | 11/2017 | Arias Espinoza et al. |
| 9,830,790 B2 | 11/2017 | Jones |
| 9,830,804 B2 | 11/2017 | Kreiner et al. |
| 9,835,064 B2 | 12/2017 | Cassani et al. |
| 9,835,104 B2 | 12/2017 | Okazaki et al. |
| 9,835,602 B2 | 12/2017 | Brasfield |
| 9,836,953 B2 | 12/2017 | Fadell et al. |
| 9,841,400 B2 | 12/2017 | Vingerhoets et al. |
| 9,842,479 B1 | 12/2017 | Black |
| 9,844,339 B2 | 12/2017 | Wang et al. |
| 9,845,503 B2 | 12/2017 | Swartz |
| 9,846,110 B2 | 12/2017 | Tylutki et al. |
| 9,850,840 B2 | 12/2017 | Miyamoto et al. |
| 9,854,641 B2 | 12/2017 | Chen |
| 9,855,820 B2 | 1/2018 | Baron, Jr. et al. |
| 9,857,299 B2 | 1/2018 | Lear et al. |
| 9,858,784 B2 | 1/2018 | Peeters et al. |
| 9,858,794 B2 | 1/2018 | McCleary et al. |
| 9,860,839 B2 | 1/2018 | Kates |
| 9,861,126 B2 | 1/2018 | Utley et al. |
| 9,862,985 B2 | 1/2018 | Lim et al. |
| 9,863,354 B2 | 1/2018 | Okazaki et al. |
| 9,863,375 B2 | 1/2018 | Takakura et al. |
| 9,863,641 B2 | 1/2018 | Boyd |
| 9,863,656 B2 | 1/2018 | Amerson |
| 9,863,923 B2 | 1/2018 | Abbott et al. |
| 9,865,157 B2 | 1/2018 | Hayek |
| 9,870,696 B2 | 1/2018 | Aich et al. |
| 9,874,167 B2 | 1/2018 | MacEwen et al. |
| 9,874,171 B2 | 1/2018 | Bleile et al. |
| 9,874,334 B2 | 1/2018 | Chen |
| 9,875,631 B2 | 1/2018 | Mittleman et al. |
| 9,877,507 B2 | 1/2018 | Xiang |
| 9,877,519 B2 | 1/2018 | Xiang |
| 9,879,580 B2 | 1/2018 | Gupta et al. |
| 9,879,587 B2 | 1/2018 | Kim et al. |
| 9,879,628 B2 | 1/2018 | Nishijima et al. |
| 9,879,630 B2 | 1/2018 | Guo et al. |
| 9,880,083 B2 | 1/2018 | Gaertner et al. |
| 9,880,138 B1 | 1/2018 | Hall et al. |
| 9,881,130 B2 | 1/2018 | Jackson |
| 9,881,470 B2 | 1/2018 | Baynes et al. |

(56) References Cited

U.S. PATENT DOCUMENTS

| | | |
|---|---|---|
| 9,883,001 B2 | 1/2018 | Verna et al. |
| 9,884,269 B2 | 2/2018 | Hunter et al. |
| 9,890,678 B2 | 2/2018 | Qi |
| 9,890,685 B2 | 2/2018 | Jang |
| 9,890,969 B2 | 2/2018 | Martin |
| 9,891,139 B2 | 2/2018 | Nakasone et al. |
| 9,892,456 B1 | 2/2018 | Kalaboukis et al. |
| 9,892,615 B2 | 2/2018 | Glasgow et al. |
| 9,896,989 B2 | 2/2018 | Kakimoto |
| 9,897,028 B2 | 2/2018 | Miyamoto et al. |
| 9,897,592 B2 | 2/2018 | Ray et al. |
| 9,898,916 B2 | 2/2018 | Valleru |
| 9,903,292 B2 | 2/2018 | Miyamoto et al. |
| 9,903,634 B2 | 2/2018 | Son et al. |
| 9,903,846 B2 | 2/2018 | Bright |
| 9,905,122 B2 | 2/2018 | Sloo et al. |
| 9,909,473 B2 | 3/2018 | Martin et al. |
| 9,909,480 B2 | 3/2018 | Mitchell et al. |
| 9,909,482 B2 | 3/2018 | Ardanese et al. |
| 9,909,540 B2 | 3/2018 | Heinrich et al. |
| 9,909,541 B1 | 3/2018 | Bevan et al. |
| 9,913,124 B2 | 3/2018 | Liu |
| 9,914,341 B2 | 3/2018 | Ono et al. |
| 9,914,760 B2 | 3/2018 | Pfister et al. |
| 9,920,944 B2 | 3/2018 | Chromy et al. |
| 9,922,513 B1 | 3/2018 | Hall et al. |
| 9,922,517 B2 | 3/2018 | Adams et al. |
| 9,922,530 B2 | 3/2018 | Wu et al. |
| 9,927,413 B2 | 3/2018 | Gong et al. |
| 9,928,672 B2 | 3/2018 | Jablokov et al. |
| 9,929,494 B2 | 3/2018 | Schmidt et al. |
| 9,932,938 B2 | 4/2018 | Surnilla et al. |
| 9,939,307 B2 | 4/2018 | Hall et al. |
| 9,939,348 B2 | 4/2018 | Nakasone et al. |
| 9,939,412 B2 | 4/2018 | Ichimura et al. |
| 9,940,805 B1 | 4/2018 | Mona |
| 9,940,820 B2 | 4/2018 | Watkins et al. |
| 9,943,563 B2 | 4/2018 | Wilson |
| 9,943,806 B2 | 4/2018 | Minezawa et al. |
| 9,945,312 B2 | 4/2018 | Tanaka |
| 9,945,573 B2 | 4/2018 | Balkhair |
| 9,953,513 B2 | 4/2018 | Chua |
| 9,955,242 B1 | 4/2018 | Manzella et al. |
| 9,955,423 B2 | 4/2018 | Kates |
| 9,955,728 B2 | 5/2018 | Liu |
| 9,955,898 B2 | 5/2018 | Ra et al. |
| 9,957,872 B2 | 5/2018 | Aoyama et al. |
| 9,957,924 B2 | 5/2018 | Dudar |
| 9,958,168 B2 | 5/2018 | Robison et al. |
| 9,959,717 B2 | 5/2018 | Thornton et al. |
| 9,959,735 B2 | 5/2018 | Patil et al. |
| 9,964,530 B2 | 5/2018 | Baldaccini |
| 9,964,973 B2 | 5/2018 | Smith et al. |
| 9,970,372 B2 | 5/2018 | Kumar et al. |
| 9,970,916 B2 | 5/2018 | Singer et al. |
| 9,976,503 B2 | 5/2018 | Surnilla et al. |
| 9,976,521 B1 | 5/2018 | Jentz et al. |
| 9,976,717 B2 | 5/2018 | Li |
| 9,978,251 B2 | 5/2018 | Gonia et al. |
| 9,982,471 B2 | 5/2018 | Ozkan |
| 9,983,011 B2 | 5/2018 | Mountain |
| 9,983,124 B2 | 5/2018 | Wang et al. |
| 9,983,182 B2 | 5/2018 | Chen et al. |
| 9,983,183 B2 | 5/2018 | Motayed et al. |
| 9,984,555 B2 | 5/2018 | Bieser |
| 9,988,963 B2 | 6/2018 | Maertens et al. |
| 9,989,003 B2 | 6/2018 | Karunaratne |
| 9,989,018 B2 | 6/2018 | Dudar |
| 9,989,474 B2 | 6/2018 | Song et al. |
| 9,989,507 B2 | 6/2018 | Benn |
| 9,990,841 B2 | 6/2018 | Moffa |
| 9,994,569 B2 | 6/2018 | George et al. |
| 9,995,653 B2 | 6/2018 | Stojicevic et al. |
| 9,995,674 B2 | 6/2018 | Prasad |
| 9,997,046 B2 | 6/2018 | Bermudez Rodriguez et al. |
| 9,997,057 B2 | 6/2018 | Pimentel |
| 9,997,058 B2 | 6/2018 | Sloo et al. |
| 9,998,899 B1 | 6/2018 | Tannenbaum |
| 10,001,045 B2 | 6/2018 | Kumar et al. |
| 10,006,896 B2 | 6/2018 | Fernstrom et al. |
| 10,011,481 B2 | 7/2018 | Haick |
| 10,012,169 B2 | 7/2018 | Rueger et al. |
| 10,013,872 B1 | 7/2018 | Seigler et al. |
| 10,015,743 B2 | 7/2018 | Kates |
| 10,018,091 B2 | 7/2018 | Hendrickson et al. |
| 10,018,158 B2 | 7/2018 | Dudar |
| 10,026,304 B2 | 7/2018 | Taylor et al. |
| 10,031,125 B2 | 7/2018 | Koo et al. |
| 10,031,126 B2 | 7/2018 | Blake et al. |
| 10,032,363 B2 | 7/2018 | Bruck et al. |
| 10,034,979 B2 | 7/2018 | Bechtel et al. |
| 10,035,837 B2 | 7/2018 | Zhang et al. |
| 10,036,297 B2 | 7/2018 | Khaled et al. |
| 10,041,427 B2 | 8/2018 | Hanawa et al. |
| 10,041,908 B2 | 8/2018 | Kim et al. |
| 10,041,916 B2 | 8/2018 | Michalske |
| 10,041,917 B2 | 8/2018 | Bardoni |
| 10,041,935 B2 | 8/2018 | Rinberg et al. |
| 10,043,593 B2 | 8/2018 | Jackson |
| 10,046,262 B2 | 8/2018 | Buckner |
| 10,047,971 B2 | 8/2018 | Nyamjav et al. |
| 10,048,243 B2 | 8/2018 | Yamamoto |
| 10,052,045 B2 | 8/2018 | Hao et al. |
| 10,053,650 B2 | 8/2018 | Angel et al. |
| 10,054,070 B2 | 8/2018 | Dudar et al. |
| 10,054,096 B2 | 8/2018 | Berkson |
| 10,054,499 B2 | 8/2018 | Karunaratne et al. |
| 10,055,803 B2 | 8/2018 | Orduna et al. |
| 10,058,627 B2 | 8/2018 | Kelsen |
| 10,060,111 B2 | 8/2018 | Hall et al. |
| 10,060,259 B2 | 8/2018 | McAlary et al. |
| 10,060,346 B2 | 8/2018 | Pfister et al. |
| 10,060,829 B2 | 8/2018 | Hanawa et al. |
| 10,060,894 B2 | 8/2018 | Michalske |
| 10,062,261 B2 | 8/2018 | Shaffer |
| 10,063,814 B2 | 8/2018 | Wood et al. |
| 10,066,114 B2 | 9/2018 | Jackson et al. |
| 10,066,533 B2 | 9/2018 | Kogo et al. |
| 10,066,567 B2 | 9/2018 | Kato |
| 10,067,108 B2 | 9/2018 | King-Smith et al. |
| 10,072,542 B2 | 9/2018 | Fujii et al. |
| 10,078,054 B2 | 9/2018 | Heywood et al. |
| 10,087,395 B2 | 10/2018 | Pelzer et al. |
| 10,089,848 B2 | 10/2018 | Albinger et al. |
| 10,092,671 B2 | 10/2018 | Duong et al. |
| 10,094,264 B2 | 10/2018 | Khaled et al. |
| 10,094,310 B2 | 10/2018 | Ulrey et al. |
| 10,094,312 B2 | 10/2018 | Brennan et al. |
| 10,094,725 B2 | 10/2018 | Reinmuth et al. |
| 10,094,803 B2 | 10/2018 | Reinhardt et al. |
| 10,100,695 B2 | 10/2018 | Anilovich et al. |
| 10,100,698 B2 | 10/2018 | Minezawa et al. |
| 10,100,770 B2 | 10/2018 | Dudar |
| 10,100,782 B2 | 10/2018 | Lucka et al. |
| 10,101,291 B2 | 10/2018 | Ho |
| 10,101,298 B1 | 10/2018 | Zhang et al. |
| 10,101,314 B2 | 10/2018 | Endou |
| 10,101,319 B2 | 10/2018 | Trowell et al. |
| 10,102,728 B1 | 10/2018 | Bajaj et al. |
| 10,103,811 B2 | 10/2018 | Stout et al. |
| 10,107,233 B2 | 10/2018 | Dudar et al. |
| 10,107,665 B2 | 10/2018 | Hall et al. |
| 10,107,827 B1 | 10/2018 | Agarwal et al. |
| 10,109,176 B2 | 10/2018 | Wright et al. |
| 10,110,857 B2 | 10/2018 | Qu et al. |
| 10,113,953 B2 | 10/2018 | Babin et al. |
| 10,115,287 B2 | 10/2018 | Rostami |
| 10,118,119 B2 | 11/2018 | Sappok et al. |
| 10,118,608 B1 | 11/2018 | Dudar |
| 10,119,448 B2 | 11/2018 | Kidokoro et al. |
| 10,119,489 B2 | 11/2018 | Hasegawa et al. |
| 10,119,847 B2 | 11/2018 | Heffernan |
| 10,120,105 B2 | 11/2018 | Haupt et al. |
| 10,121,075 B2 | 11/2018 | Du et al. |

(56) References Cited

U.S. PATENT DOCUMENTS

| | | |
|---|---|---|
| 10,122,784 B2 | 11/2018 | Rezvani et al. |
| 10,123,509 B2 | 11/2018 | Pearce et al. |
| 10,125,656 B2 | 11/2018 | Monna et al. |
| 10,125,657 B2 | 11/2018 | Monna et al. |
| 10,131,955 B2 | 11/2018 | Darling et al. |
| 10,132,250 B2 | 11/2018 | Zhong et al. |
| 10,132,727 B2 | 11/2018 | Remondini |
| 10,134,247 B2 | 11/2018 | McMahan et al. |
| 10,137,770 B2 | 11/2018 | Yamashita et al. |
| 10,138,827 B2 | 11/2018 | Dudar |
| 10,138,830 B1 | 11/2018 | Glugla |
| 10,138,846 B1 | 11/2018 | Dudar |
| 10,140,849 B2 | 11/2018 | Sloo et al. |
| 10,142,421 B2 | 11/2018 | Mighdoll et al. |
| 10,143,608 B2 | 12/2018 | Kostic |
| 10,145,285 B2 | 12/2018 | Maillard |
| 10,150,365 B2 | 12/2018 | Dudar et al. |
| 10,151,262 B2 | 12/2018 | Miyamoto et al. |
| 10,151,265 B2 | 12/2018 | Dudar |
| 10,152,866 B2 | 12/2018 | Kraz et al. |
| 10,156,176 B2 | 12/2018 | Osburn et al. |
| 10,156,200 B2 | 12/2018 | Miyamoto |
| 10,156,213 B2 | 12/2018 | Pursifull et al. |
| 10,161,284 B2 | 12/2018 | Cunningham et al. |
| 10,161,326 B2 | 12/2018 | Glugla et al. |
| 10,161,341 B2 | 12/2018 | Taibi et al. |
| 10,161,845 B2 | 12/2018 | Bovi |
| 10,161,896 B2 | 12/2018 | Gryska et al. |
| 10,161,920 B2 | 12/2018 | Hassan et al. |
| 10,167,823 B2 | 1/2019 | Dudar |
| 10,168,315 B2 | 1/2019 | Haick et al. |
| 10,168,331 B2 | 1/2019 | Ruddock et al. |
| 10,169,962 B1 | 1/2019 | Walker et al. |
| 10,176,705 B1 | 1/2019 | Grant |
| 10,176,706 B2 | 1/2019 | Beaver et al. |
| 10,176,805 B2 | 1/2019 | Carlin et al. |
| 10,179,184 B2 | 1/2019 | Belz et al. |
| 10,180,101 B1 | 1/2019 | Park et al. |
| 10,180,112 B2 | 1/2019 | Hayashita et al. |
| 10,180,673 B2 | 1/2019 | Sinha et al. |
| 10,184,382 B2 | 1/2019 | Hagiwara et al. |
| 10,184,913 B2 | 1/2019 | Aoki et al. |
| 10,186,331 B2 | 1/2019 | Jackson |
| 10,188,767 B2 | 1/2019 | Okada et al. |
| 10,190,413 B2 | 1/2019 | Smith |
| 10,191,004 B2 | 1/2019 | Koley et al. |
| 10,191,008 B2 | 1/2019 | Chapples et al. |
| 10,192,426 B2 | 1/2019 | Nold |
| 10,196,958 B2 | 2/2019 | Nakasone et al. |
| 10,197,000 B1 | 2/2019 | Dudar |
| 10,197,243 B2 | 2/2019 | Dong et al. |
| 10,197,532 B1 | 2/2019 | Manginell et al. |
| 10,202,915 B2 | 2/2019 | Mueller et al. |
| 10,209,213 B2 | 2/2019 | Kang et al. |
| 10,210,745 B2 | 2/2019 | Tung et al. |
| 10,213,038 B2 | 2/2019 | Wei et al. |
| 10,217,090 B2 | 2/2019 | Warren et al. |
| 10,217,344 B2 | 2/2019 | Gage et al. |
| 10,221,746 B2 | 3/2019 | Kidokoro et al. |
| 10,223,844 B1 | 3/2019 | Schwie et al. |
| 10,223,889 B2 | 3/2019 | Park et al. |
| 10,226,472 B2 | 3/2019 | Goodenow et al. |
| 10,227,628 B2 | 3/2019 | Moularat et al. |
| 10,227,629 B2 | 3/2019 | Koo et al. |
| 10,228,704 B2 | 3/2019 | Cohen et al. |
| 10,229,583 B2 | 3/2019 | Matsuoka et al. |
| 10,229,584 B2 | 3/2019 | Davell et al. |
| 10,232,296 B2 | 3/2019 | Takaoka et al. |
| 10,232,771 B2 | 3/2019 | Zehr |
| 10,233,856 B2 | 3/2019 | Dudar |
| 10,234,388 B2 | 3/2019 | Ebata et al. |
| 10,234,418 B2 | 3/2019 | Nakata et al. |
| 10,234,420 B2 | 3/2019 | Kayama et al. |
| 10,234,437 B2 | 3/2019 | Bright |
| 10,237,237 B2 | 3/2019 | Dawes et al. |
| 10,237,358 B2 | 3/2019 | Haupt et al. |
| 10,238,149 B2 | 3/2019 | Hon |
| 10,240,484 B2 | 3/2019 | Zhang et al. |
| 10,240,502 B2 | 3/2019 | De Smet et al. |
| 10,241,078 B2 | 3/2019 | Mohanty et al. |
| 10,241,105 B2 | 3/2019 | Kwak et al. |
| 10,242,550 B2 | 3/2019 | Glasgow et al. |
| 10,247,114 B2 | 4/2019 | Nakamura et al. |
| 10,247,714 B2 | 4/2019 | Stokes |
| 10,253,716 B2 | 4/2019 | Mentele |
| 10,253,728 B2 | 4/2019 | Dudar et al. |
| 10,254,199 B2 | 4/2019 | Pilon |
| 10,254,260 B2 | 4/2019 | Amin et al. |
| 10,254,261 B2 | 4/2019 | Le Neel et al. |
| 10,255,800 B2 | 4/2019 | Fox |
| 10,258,295 B2 | 4/2019 | Fountaine |
| 10,259,927 B2 | 4/2019 | Bercx et al. |
| 10,261,071 B2 | 4/2019 | Hall et al. |
| 10,262,507 B2 | 4/2019 | Sloo et al. |
| 10,262,508 B2 | 4/2019 | Fadell et al. |
| 10,262,525 B2 | 4/2019 | Carlin et al. |
| 10,267,778 B2 | 4/2019 | Gong et al. |
| 10,271,738 B2 | 4/2019 | Peeters |
| 10,274,390 B2 | 4/2019 | Sieber et al. |
| 10,274,467 B2 | 4/2019 | Kim et al. |
| 10,274,469 B2 | 4/2019 | Brasfield |
| 10,274,470 B2 | 4/2019 | Hunter |
| 10,276,018 B2 | 4/2019 | Brillaud |
| 10,276,022 B2 | 4/2019 | Goodson |
| 10,280,682 B1 | 5/2019 | Nagel et al. |
| 10,280,821 B2 | 5/2019 | Crawford et al. |
| 10,280,863 B2 | 5/2019 | Dudar |
| 10,281,167 B2 | 5/2019 | Martin |
| 10,281,364 B1 | 5/2019 | Kallhoff et al. |
| 10,282,960 B2 | 5/2019 | Verna et al. |
| 10,282,975 B2 | 5/2019 | King et al. |
| 10,288,277 B2 | 5/2019 | Chen |
| 10,288,592 B2 | 5/2019 | Takaoka et al. |
| 10,294,252 B2 | 5/2019 | Braddock-Wilking et al. |
| 10,295,457 B1 | 5/2019 | Ocheltree |
| 10,295,515 B2 | 5/2019 | Shao et al. |
| 10,301,991 B1 | 5/2019 | Dudar |
| 10,302,321 B2 | 5/2019 | Sakai et al. |
| 10,304,319 B2 | 5/2019 | Sager et al. |
| 10,306,922 B2 | 6/2019 | Utley et al. |
| 10,309,942 B2 | 6/2019 | Yoo |
| 10,309,944 B2 | 6/2019 | Hopka et al. |
| 10,309,953 B2 | 6/2019 | Sappok et al. |
| 10,314,251 B2 | 6/2019 | Gagne et al. |
| 10,316,767 B2 | 6/2019 | Park |
| 10,316,770 B2 | 6/2019 | Veldten et al. |
| 10,316,779 B2 | 6/2019 | Miyamoto et al. |
| 10,319,207 B1 | 6/2019 | Janscha et al. |
| 10,323,562 B2 | 6/2019 | Van Nieuwstadt et al. |
| 10,329,982 B2 | 6/2019 | Smith et al. |
| 10,329,986 B2 | 6/2019 | Wang et al. |
| 10,330,051 B2 | 6/2019 | Dudar et al. |
| 10,330,617 B2 | 6/2019 | Hur et al. |
| 10,332,383 B1 | 6/2019 | Giles |
| 10,337,377 B2 | 7/2019 | Latrofa et al. |
| 10,337,384 B2 | 7/2019 | Martin et al. |
| 10,337,422 B2 | 7/2019 | Hosoya et al. |
| 10,338,026 B2 | 7/2019 | Reinhardt et al. |
| 10,338,046 B2 | 7/2019 | Ando et al. |
| 10,339,791 B2 | 7/2019 | Baum et al. |
| 10,344,313 B2 | 7/2019 | Moularat et al. |
| 10,345,016 B2 | 7/2019 | Garing et al. |
| 10,348,575 B2 | 7/2019 | Sundermeyer et al. |
| 10,351,796 B2 | 7/2019 | Sturgis et al. |
| 10,352,223 B2 | 7/2019 | York et al. |
| 10,352,225 B2 | 7/2019 | Takita et al. |
| 10,354,351 B2 | 7/2019 | Orduna et al. |
| 10,357,587 B2 | 7/2019 | Li |
| 10,358,994 B1 | 7/2019 | Dudar |
| 10,363,514 B2 | 7/2019 | Kelly et al. |
| 10,364,717 B2 | 7/2019 | Kubinski |
| 10,364,926 B2 | 7/2019 | Taft et al. |
| 10,365,183 B2 | 7/2019 | Miyamoto et al. |
| 10,365,260 B2 | 7/2019 | Amaravadi |

(56) References Cited

U.S. PATENT DOCUMENTS

| | | |
|---|---|---|
| 10,365,810 B2 | 7/2019 | Sundermeyer et al. |
| 10,366,588 B2 | 7/2019 | Slavin et al. |
| 10,366,590 B2 | 7/2019 | Bajaj et al. |
| 10,369,509 B2 | 8/2019 | Vo |
| 10,371,600 B2 | 8/2019 | Varney |
| 10,371,677 B2 | 8/2019 | Nakada et al. |
| 10,373,472 B2 | 8/2019 | Johnston |
| 10,378,404 B2 | 8/2019 | De Smet et al. |
| 10,378,415 B2 | 8/2019 | Cole et al. |
| 10,378,472 B2 | 8/2019 | Dudar et al. |
| 10,379,072 B2 | 8/2019 | Blease et al. |
| 10,379,092 B2 | 8/2019 | Gafsou |
| 10,379,093 B2 | 8/2019 | Murphy et al. |
| 10,379,096 B2 | 8/2019 | Wang et al. |
| 10,380,875 B1 | 8/2019 | Roberts et al. |
| 10,383,174 B2 | 8/2019 | Louveau et al. |
| 10,385,752 B2 | 8/2019 | Matsumoto et al. |
| 10,385,753 B2 | 8/2019 | Nobukawa et al. |
| 10,386,325 B2 | 8/2019 | Xiao et al. |
| 10,386,348 B2 | 8/2019 | Kim et al. |
| 10,386,349 B2 | 8/2019 | Zaripov et al. |
| 10,391,193 B2 | 8/2019 | Peterson et al. |
| 10,393,713 B2 | 8/2019 | Lemire et al. |
| 10,393,763 B2 | 8/2019 | Kita et al. |
| 10,400,654 B2 | 9/2019 | Wiebenga et al. |
| 10,401,336 B2 | 9/2019 | Spartz et al. |
| 10,401,340 B2 | 9/2019 | Soundarrajan et al. |
| 10,405,072 B1 | 9/2019 | Manzella et al. |
| 10,408,111 B2 | 9/2019 | Hall et al. |
| 10,408,114 B2 | 9/2019 | Rollinger et al. |
| 10,408,143 B2 | 9/2019 | Dudar |
| 10,408,154 B2 | 9/2019 | Dudar |
| 10,408,158 B2 | 9/2019 | Klingbeil |
| 10,408,471 B1 | 9/2019 | Lanouette |
| 10,408,809 B1 | 9/2019 | Emanuel et al. |
| 10,412,985 B2 | 9/2019 | Byron et al. |
| 10,416,138 B2 | 9/2019 | Byron et al. |
| 10,416,142 B2 | 9/2019 | Mazzillo et al. |
| 10,417,899 B2 | 9/2019 | Kim |
| 10,422,292 B2 | 9/2019 | Glugla |
| 10,422,771 B2 | 9/2019 | Kuroki et al. |
| 10,424,412 B2 | 9/2019 | Huang |
| 10,428,717 B2 | 10/2019 | Monna et al. |
| 10,429,330 B2 | 10/2019 | Le Neel et al. |
| 10,429,335 B2 | 10/2019 | Porro et al. |
| 10,429,367 B2 | 10/2019 | Crescini et al. |
| 10,431,055 B2 | 10/2019 | Palmer et al. |
| 10,431,060 B2 | 10/2019 | Saidi |
| 10,436,138 B2 | 10/2019 | Dudar |
| 10,438,457 B2 | 10/2019 | Kramer et al. |
| 10,438,472 B2 | 10/2019 | Haynes et al. |
| 10,441,178 B2 | 10/2019 | Campo et al. |
| 10,443,471 B2 | 10/2019 | Funk et al. |
| 10,443,517 B2 | 10/2019 | Glugla |
| 10,444,123 B2 | 10/2019 | Koo et al. |
| 10,450,733 B2 | 10/2019 | Luettgen et al. |
| 10,450,932 B2 | 10/2019 | Tsutsumi |
| 10,450,933 B2 | 10/2019 | Quigley et al. |
| 10,450,983 B2 | 10/2019 | Glugla et al. |
| 10,450,985 B2 | 10/2019 | Nagar et al. |
| 10,451,010 B2 | 10/2019 | Dudar |
| 10,453,321 B2 | 10/2019 | Adams et al. |
| 10,455,395 B2 | 10/2019 | Gharabegian |
| 10,455,817 B2 | 10/2019 | Hall et al. |
| 10,457,200 B2 | 10/2019 | Gage et al. |
| 10,458,306 B2 | 10/2019 | Takaoka et al. |
| 10,458,372 B2 | 10/2019 | Michalske et al. |
| 10,458,627 B2 | 10/2019 | Perez-Bolivar et al. |
| 10,459,227 B2 | 10/2019 | Norrell |
| 10,462,876 B2 | 10/2019 | Nicholas et al. |
| 10,465,961 B2 | 11/2019 | Kujak |
| 10,467,879 B2 | 11/2019 | Stefanski et al. |
| 10,467,885 B2 | 11/2019 | Trundle et al. |
| 10,467,887 B2 | 11/2019 | Herman et al. |
| 10,471,804 B1 * | 11/2019 | Wengreen .......... B60H 1/00828 |
| 10,473,635 B2 | 11/2019 | Wang |
| 10,475,318 B2 | 11/2019 | Peeters et al. |
| 10,475,319 B2 | 11/2019 | Janscha et al. |
| 10,476,294 B2 | 11/2019 | Wang et al. |
| 10,479,213 B2 | 11/2019 | Lee et al. |
| 10,480,368 B2 | 11/2019 | Santillo et al. |
| 10,480,375 B2 | 11/2019 | Khaled |
| 10,480,384 B2 | 11/2019 | Khaled et al. |
| 10,482,698 B2 | 11/2019 | Caterino et al. |
| 10,482,759 B2 | 11/2019 | Sayavong et al. |
| 10,487,782 B2 | 11/2019 | Bevan et al. |
| 10,488,064 B1 | 11/2019 | Crowder et al. |
| 10,488,315 B2 | 11/2019 | Weber et al. |
| 10,488,837 B2 | 11/2019 | Cirino |
| 10,492,967 B2 | 12/2019 | Kostic |
| 10,494,972 B2 | 12/2019 | Collins et al. |
| 10,494,976 B2 | 12/2019 | Qi et al. |
| 10,502,723 B2 | 12/2019 | Cai et al. |
| 10,508,582 B2 | 12/2019 | Hall et al. |
| 10,508,822 B1 | 12/2019 | Sheikh et al. |
| 10,508,984 B2 | 12/2019 | Alessi et al. |
| 10,509,377 B2 | 12/2019 | Willette et al. |
| 10,511,404 B2 | 12/2019 | Trundle et al. |
| 10,513,961 B2 | 12/2019 | Yoo et al. |
| 10,513,997 B2 | 12/2019 | Dudar |
| 10,514,368 B2 | 12/2019 | Sugar |
| 10,517,329 B2 | 12/2019 | Batista |
| 10,517,530 B2 | 12/2019 | Cohen |
| 10,519,841 B2 | 12/2019 | Bokelund et al. |
| 10,520,203 B2 | 12/2019 | O'Hayer |
| 10,520,465 B2 | 12/2019 | Perry et al. |
| 10,522,026 B2 | 12/2019 | Sundermeyer et al. |
| 10,526,942 B2 | 1/2020 | Higashiyama |
| 10,527,305 B2 | 1/2020 | Lin et al. |
| 10,529,195 B2 | 1/2020 | Sloo et al. |
| 10,529,196 B2 | 1/2020 | Sloo et al. |
| 10,529,223 B2 | 1/2020 | Kalagani et al. |
| 10,533,930 B2 | 1/2020 | Chrin |
| 10,533,964 B2 | 1/2020 | Snelders et al. |
| 10,537,135 B2 | 1/2020 | Smith et al. |
| 10,537,653 B2 | 1/2020 | Kelsen |
| 10,539,060 B2 | 1/2020 | Moos et al. |
| 10,539,087 B2 | 1/2020 | Brahma et al. |
| 10,539,088 B2 | 1/2020 | Rausing et al. |
| 10,540,864 B2 | 1/2020 | Sloo et al. |
| 10,540,871 B2 | 1/2020 | Wedig et al. |
| 10,544,743 B2 | 1/2020 | Lundstrom |
| 10,545,072 B2 | 1/2020 | Monna et al. |
| 10,545,120 B2 | 1/2020 | Meck et al. |
| 10,546,469 B2 | 1/2020 | Peterson et al. |
| 10,550,749 B2 | 2/2020 | Guo |
| 2001/0017056 A1 | 8/2001 | Nakagawa et al. |
| 2001/0042371 A1 | 11/2001 | Topfer-Hartung et al. |
| 2001/0045895 A1 | 11/2001 | Ellis et al. |
| 2002/0010090 A1 | 1/2002 | Ono |
| 2002/0011069 A1 | 1/2002 | Maus et al. |
| 2002/0023430 A1 | 2/2002 | Takaku et al. |
| 2002/0041860 A1 | 4/2002 | Requejo |
| 2002/0074000 A1 | 6/2002 | Benda |
| 2002/0114744 A1 | 8/2002 | Chiao et al. |
| 2002/0120386 A1 | 8/2002 | Shi et al. |
| 2002/0129599 A1 | 9/2002 | Nakagawa et al. |
| 2002/0146361 A1 | 10/2002 | Gardner et al. |
| 2002/0155622 A1 | 10/2002 | Slater et al. |
| 2002/0157483 A1 | 10/2002 | Lo et al. |
| 2002/0177168 A1 | 11/2002 | Ikematsu |
| 2002/0182739 A1 | 12/2002 | Sadik et al. |
| 2002/0183001 A1 | 12/2002 | Holter et al. |
| 2002/0193554 A1 | 12/2002 | Hirata et al. |
| 2003/0000207 A1 | 1/2003 | Nakagawa et al. |
| 2003/0012696 A1 | 1/2003 | Millancourt |
| 2003/0017618 A1 | 1/2003 | Ikematsu |
| 2003/0020618 A1 | 1/2003 | Hemmer et al. |
| 2003/0090374 A1 | 5/2003 | Quigley |
| 2003/0106367 A1 | 6/2003 | Osaki et al. |
| 2003/0106368 A1 | 6/2003 | Osaki et al. |
| 2003/0116711 A1 | 6/2003 | Hara et al. |
| 2003/0127105 A1 | 7/2003 | Fontana |
| 2003/0129757 A1 | 7/2003 | Rohleder |

(56) References Cited

U.S. PATENT DOCUMENTS

| | | |
|---|---|---|
| 2003/0129936 A1 | 7/2003 | Shaikh |
| 2003/0153088 A1 | 8/2003 | DiMeo et al. |
| 2003/0157006 A1 | 8/2003 | Hei et al. |
| 2003/0164024 A1 | 9/2003 | Mitsubayashi et al. |
| 2003/0165879 A1 | 9/2003 | Woods et al. |
| 2003/0170904 A1 | 9/2003 | Hibbert et al. |
| 2003/0171090 A1 | 9/2003 | Shaikh |
| 2003/0186641 A1 | 10/2003 | Shaikh |
| 2003/0192305 A1 | 10/2003 | Iihoshi et al. |
| 2003/0198572 A1 | 10/2003 | Carnahan |
| 2003/0206834 A1 | 11/2003 | Chiao et al. |
| 2003/0214394 A1 | 11/2003 | Behrendsen |
| 2003/0223068 A1 | 12/2003 | DiFoggio et al. |
| 2004/0002160 A1 | 1/2004 | Shih et al. |
| 2004/0006435 A1 | 1/2004 | Blumenthal et al. |
| 2004/0009605 A1 | 1/2004 | Brown et al. |
| 2004/0016287 A1 | 1/2004 | Fu |
| 2004/0028967 A1 | 2/2004 | Katsuki et al. |
| 2004/0032335 A1 | 2/2004 | Parrish |
| 2004/0033067 A1 | 2/2004 | He et al. |
| 2004/0050137 A1 | 3/2004 | Hoppenworth |
| 2004/0050188 A1 | 3/2004 | Richards et al. |
| 2004/0052683 A1 | 3/2004 | Fudali et al. |
| 2004/0054921 A1 | 3/2004 | Land |
| 2004/0077424 A1 | 4/2004 | Murphy et al. |
| 2004/0081582 A1 | 4/2004 | Brooke |
| 2004/0099233 A1 | 5/2004 | Fujimoto et al. |
| 2004/0110299 A1 | 6/2004 | Sivavec |
| 2004/0115319 A1 | 6/2004 | Morris et al. |
| 2004/0115818 A1 | 6/2004 | Puri et al. |
| 2004/0124989 A1 | 7/2004 | Bachinski et al. |
| 2004/0126888 A1 | 7/2004 | Puri |
| 2004/0133453 A1 | 7/2004 | Jomini et al. |
| 2004/0141919 A1 | 7/2004 | Robertson |
| 2004/0145466 A1 | 7/2004 | Anthony et al. |
| 2004/0146435 A1 | 7/2004 | Goldstein et al. |
| 2004/0149007 A1 | 8/2004 | Staphanos |
| 2004/0156742 A1 | 8/2004 | Milan et al. |
| 2004/0160329 A1 | 8/2004 | Flanc |
| 2004/0179970 A1 | 9/2004 | Matsubara et al. |
| 2004/0189982 A1 | 9/2004 | Galarneau et al. |
| 2004/0196465 A1 | 10/2004 | Arnold et al. |
| 2004/0197919 A1 | 10/2004 | Herman et al. |
| 2004/0203379 A1 | 10/2004 | Witkowski et al. |
| 2004/0235430 A1 | 11/2004 | Ma et al. |
| 2004/0238378 A1 | 12/2004 | Kumazawa et al. |
| 2004/0260454 A1 | 12/2004 | Basir |
| 2005/0024493 A1 | 2/2005 | Nam |
| 2005/0029102 A1 | 2/2005 | Breuer et al. |
| 2005/0042214 A1 | 2/2005 | Gershwin et al. |
| 2005/0045734 A1 | 3/2005 | Peng et al. |
| 2005/0054942 A1 | 3/2005 | Melker et al. |
| 2005/0056002 A1 | 3/2005 | Nakagawa et al. |
| 2005/0069304 A1 | 3/2005 | He et al. |
| 2005/0069307 A1 | 3/2005 | He et al. |
| 2005/0075552 A1 | 4/2005 | Schmidt et al. |
| 2005/0081601 A1 | 4/2005 | Lawson |
| 2005/0092914 A1 | 5/2005 | Miller et al. |
| 2005/0100478 A1 | 5/2005 | Harvey |
| 2005/0102998 A1 | 5/2005 | van Nieuwstadt et al. |
| 2005/0106741 A1 | 5/2005 | Dijke |
| 2005/0129654 A1 | 6/2005 | Myers |
| 2005/0142966 A1 | 6/2005 | Quincy et al. |
| 2005/0147963 A1 | 7/2005 | Su et al. |
| 2005/0155366 A1 | 7/2005 | Kim et al. |
| 2005/0160789 A1 | 7/2005 | Freyer et al. |
| 2005/0179541 A1 | 8/2005 | Wolfe |
| 2005/0188680 A1 | 9/2005 | Ueda et al. |
| 2005/0194460 A1 | 9/2005 | Selander |
| 2005/0195366 A1 | 9/2005 | Selander et al. |
| 2005/0199041 A1 | 9/2005 | Weber et al. |
| 2005/0199245 A1 | 9/2005 | Brennan |
| 2005/0214950 A1 | 9/2005 | Roeder et al. |
| 2005/0233063 A1 | 10/2005 | Weiler et al. |
| 2005/0233459 A1 | 10/2005 | Melker et al. |
| 2005/0240092 A1 | 10/2005 | Shah et al. |
| 2005/0241297 A1 | 11/2005 | Wang et al. |
| 2005/0242948 A1 | 11/2005 | Tarr |
| 2005/0242968 A1 | 11/2005 | Reid |
| 2005/0247105 A1 | 11/2005 | Dikken et al. |
| 2005/0252197 A1 | 11/2005 | Nieuwstadt et al. |
| 2005/0253709 A1 | 11/2005 | Baker |
| 2005/0257540 A1 | 11/2005 | Choi et al. |
| 2005/0262943 A1 | 12/2005 | Claydon et al. |
| 2005/0263394 A1 | 12/2005 | Lewis et al. |
| 2005/0274390 A1 | 12/2005 | Banerjee et al. |
| 2005/0284158 A1 | 12/2005 | Lee et al. |
| 2006/0000259 A1 | 1/2006 | Rothschild et al. |
| 2006/0000971 A1 | 1/2006 | Jones et al. |
| 2006/0001741 A1 | 1/2006 | Hsu et al. |
| 2006/0005710 A1 | 1/2006 | Uegaki et al. |
| 2006/0015599 A1 | 1/2006 | Li et al. |
| 2006/0024839 A1 | 2/2006 | Petropavlovskikh et al. |
| 2006/0044133 A1 | 3/2006 | Lou |
| 2006/0045849 A1 | 3/2006 | Taghizadeh |
| 2006/0049048 A1 | 3/2006 | Kondo et al. |
| 2006/0059895 A1 | 3/2006 | Pott |
| 2006/0085831 A1 | 4/2006 | Jones et al. |
| 2006/0101808 A1 | 5/2006 | Nakagawa et al. |
| 2006/0108739 A1 | 5/2006 | Lutz |
| 2006/0109136 A1 | 5/2006 | Sumlin et al. |
| 2006/0116811 A1 | 6/2006 | Willard |
| 2006/0117362 A1 | 6/2006 | Jones et al. |
| 2006/0130663 A1 | 6/2006 | Joshi et al. |
| 2006/0146126 A1 | 7/2006 | Guo |
| 2006/0154784 A1 | 7/2006 | Surnilla et al. |
| 2006/0155439 A1 | 7/2006 | Slawinski et al. |
| 2006/0171845 A1 | 8/2006 | Martin et al. |
| 2006/0183243 A1 | 8/2006 | Rohleder |
| 2006/0191319 A1 | 8/2006 | Kurup |
| 2006/0196167 A1 | 9/2006 | Odajima et al. |
| 2006/0199271 A1 | 9/2006 | Lian et al. |
| 2006/0199513 A1 | 9/2006 | Choi et al. |
| 2006/0210442 A1 | 9/2006 | Shibata |
| 2006/0211119 A1 | 9/2006 | Herman et al. |
| 2006/0218895 A1 | 10/2006 | Wickert |
| 2006/0226972 A1 | 10/2006 | Smith |
| 2006/0229009 A1 | 10/2006 | Illing et al. |
| 2006/0237333 A1 | 10/2006 | Planje |
| 2006/0246592 A1 | 11/2006 | Hashmonay |
| 2006/0250236 A1 | 11/2006 | Ackley et al. |
| 2006/0254004 A1 | 11/2006 | Fraenkel |
| 2006/0255931 A1 | 11/2006 | Hartsfield et al. |
| 2006/0258215 A1 | 11/2006 | Lai et al. |
| 2006/0260295 A1 | 11/2006 | Gielen |
| 2006/0263892 A1 | 11/2006 | Withbroe et al. |
| 2006/0272704 A1 | 12/2006 | Fima |
| 2007/0003980 A1 | 1/2007 | Woods et al. |
| 2007/0008099 A1 | 1/2007 | Kimmel et al. |
| 2007/0008104 A1 | 1/2007 | McBain |
| 2007/0017212 A1 | 1/2007 | Yamauchi et al. |
| 2007/0023540 A1 | 2/2007 | Selander |
| 2007/0024455 A1 | 2/2007 | Morris |
| 2007/0028596 A1 | 2/2007 | Takaku et al. |
| 2007/0041865 A1 | 2/2007 | Ayoub et al. |
| 2007/0044457 A1 | 3/2007 | Upadhyay et al. |
| 2007/0049259 A1 | 3/2007 | Onishi et al. |
| 2007/0050095 A1 | 3/2007 | Nelson et al. |
| 2007/0052533 A1 | 3/2007 | Glazer |
| 2007/0053787 A1 | 3/2007 | Roberts et al. |
| 2007/0066215 A1 | 3/2007 | Song et al. |
| 2007/0069882 A1 | 3/2007 | Mahajan |
| 2007/0075844 A1 | 4/2007 | Taylor |
| 2007/0080021 A1 | 4/2007 | Collins |
| 2007/0084196 A1 | 4/2007 | Surnilla et al. |
| 2007/0085692 A1 | 4/2007 | Grant et al. |
| 2007/0088472 A1 | 4/2007 | Ganzhorn et al. |
| 2007/0095050 A1 | 5/2007 | Asano |
| 2007/0101867 A1 | 5/2007 | Hunter et al. |
| 2007/0103329 A1 | 5/2007 | Lin |
| 2007/0105494 A1 | 5/2007 | Lin |
| 2007/0111655 A1 | 5/2007 | Song et al. |
| 2007/0116607 A1 | 5/2007 | Wang et al. |
| 2007/0120978 A1 | 5/2007 | Jones et al. |

(56) References Cited

U.S. PATENT DOCUMENTS

| | | |
|---|---|---|
| 2007/0131566 A1 | 6/2007 | Filanovsky et al. |
| 2007/0134133 A1 | 6/2007 | Wenzhi et al. |
| 2007/0134196 A1 | 6/2007 | Park et al. |
| 2007/0137181 A1 | 6/2007 | Upadhyay et al. |
| 2007/0144143 A1 | 6/2007 | Kaneeda et al. |
| 2007/0146150 A1 | 6/2007 | Calabrese et al. |
| 2007/0153985 A1 | 7/2007 | Tsao et al. |
| 2007/0157323 A1 | 7/2007 | Carlson et al. |
| 2007/0163893 A1 | 7/2007 | Filanovsky |
| 2007/0166186 A1 | 7/2007 | Stec |
| 2007/0166585 A1 | 7/2007 | Mench et al. |
| 2007/0167853 A1 | 7/2007 | Melker et al. |
| 2007/0181426 A1 | 8/2007 | Fleischer et al. |
| 2007/0204388 A1 | 9/2007 | Zyskowski et al. |
| 2007/0222627 A1 | 9/2007 | Chen et al. |
| 2007/0229237 A1 | 10/2007 | Kates |
| 2007/0229834 A1 | 10/2007 | Patel et al. |
| 2007/0233360 A1 | 10/2007 | Hill et al. |
| 2007/0234708 A1 | 10/2007 | Jones et al. |
| 2007/0234730 A1 | 10/2007 | Markham et al. |
| 2007/0258849 A1 | 11/2007 | Kent |
| 2007/0261558 A1 | 11/2007 | Ashworth |
| 2007/0264680 A1 | 11/2007 | Allef et al. |
| 2007/0264927 A1 | 11/2007 | Choi et al. |
| 2007/0268367 A1 | 11/2007 | Agmon |
| 2007/0269854 A1 | 11/2007 | Nigretto et al. |
| 2007/0272211 A1 | 11/2007 | Kassner |
| 2007/0272852 A1 | 11/2007 | Miller et al. |
| 2007/0283682 A1 | 12/2007 | Cullen et al. |
| 2007/0298758 A1 | 12/2007 | Verma et al. |
| 2007/0298994 A1 | 12/2007 | Finke et al. |
| 2008/0007397 A1 | 1/2008 | Glazer |
| 2008/0014648 A1 | 1/2008 | Poncelet et al. |
| 2008/0018484 A1 | 1/2008 | Sager |
| 2008/0022756 A1 | 1/2008 | Wilson et al. |
| 2008/0028826 A1 | 2/2008 | Schmitt et al. |
| 2008/0030352 A1 | 2/2008 | Shaw |
| 2008/0034962 A1 | 2/2008 | Kiern |
| 2008/0036618 A1 | 2/2008 | Von Gunten |
| 2008/0049414 A1 | 2/2008 | McKay |
| 2008/0055098 A1 | 3/2008 | Toland |
| 2008/0062674 A1 | 3/2008 | McKay |
| 2008/0085860 A1 | 4/2008 | Bokvist et al. |
| 2008/0092631 A1 | 4/2008 | Griswold |
| 2008/0099333 A1 | 5/2008 | Nair |
| 2008/0110241 A1 | 5/2008 | Rothschild et al. |
| 2008/0129497 A1 | 6/2008 | Woodard et al. |
| 2008/0138051 A1 | 6/2008 | Velazquez et al. |
| 2008/0141754 A1 | 6/2008 | Kates |
| 2008/0143517 A1 | 6/2008 | Goffin |
| 2008/0149665 A1 | 6/2008 | Hafer et al. |
| 2008/0169934 A1 | 7/2008 | Lang et al. |
| 2008/0173817 A1 | 7/2008 | Goldstein et al. |
| 2008/0180260 A1 | 7/2008 | Shirlee |
| 2008/0180261 A1 | 7/2008 | Shirlee |
| 2008/0182506 A1 | 7/2008 | Jackson et al. |
| 2008/0191863 A1 | 8/2008 | Boling et al. |
| 2008/0224848 A1 | 9/2008 | Meyer |
| 2008/0224856 A1 | 9/2008 | Verma et al. |
| 2008/0231468 A1 | 9/2008 | Myllymaki |
| 2008/0242219 A1 | 10/2008 | Wright |
| 2008/0258903 A1 | 10/2008 | Le et al. |
| 2008/0258904 A1 | 10/2008 | Moss |
| 2008/0271439 A1 | 11/2008 | Londos |
| 2008/0280551 A1 | 11/2008 | Ashworth |
| 2008/0289962 A1 | 11/2008 | Prohaska et al. |
| 2008/0292495 A1 | 11/2008 | Frechen et al. |
| 2008/0302360 A1 | 12/2008 | Chambers |
| 2008/0303678 A1 | 12/2008 | McCredy |
| 2008/0312786 A1 | 12/2008 | Day |
| 2009/0001191 A1 | 1/2009 | Gutovic |
| 2009/0005917 A1 | 1/2009 | Hole |
| 2009/0019919 A1 | 1/2009 | Derumez |
| 2009/0029403 A1 | 1/2009 | Fleischer et al. |
| 2009/0038555 A1 | 2/2009 | Reese |
| 2009/0045937 A1 | 2/2009 | Zimmerman |
| 2009/0053989 A1 | 2/2009 | Lunde et al. |
| 2009/0058431 A1 | 3/2009 | Dass et al. |
| 2009/0074922 A1 | 3/2009 | Garwood |
| 2009/0089107 A1 | 4/2009 | Angell et al. |
| 2009/0101501 A1 | 4/2009 | Tao et al. |
| 2009/0102679 A1 | 4/2009 | Schoettle |
| 2009/0104072 A1 | 4/2009 | Ando et al. |
| 2009/0117012 A1 | 5/2009 | Bankers et al. |
| 2009/0120449 A1 | 5/2009 | Tindall |
| 2009/0121860 A1 | 5/2009 | Kimmel et al. |
| 2009/0124003 A1 | 5/2009 | Matsunami et al. |
| 2009/0126382 A1 | 5/2009 | Rubino et al. |
| 2009/0134993 A1 | 5/2009 | Ashworth |
| 2009/0139212 A1 | 6/2009 | Miwa |
| 2009/0139459 A1 | 6/2009 | Habacivch et al. |
| 2009/0151425 A1 | 6/2009 | Miwa |
| 2009/0163140 A1 | 6/2009 | Packham et al. |
| 2009/0165440 A1 | 7/2009 | Sawada et al. |
| 2009/0174561 A1 | 7/2009 | Liu et al. |
| 2009/0187111 A1 | 7/2009 | Reilly, Jr. et al. |
| 2009/0192340 A1 | 7/2009 | Culp et al. |
| 2009/0199543 A1 | 8/2009 | Sawada et al. |
| 2009/0212959 A1 | 8/2009 | Suber, III |
| 2009/0228151 A1 | 9/2009 | Wang et al. |
| 2009/0230300 A1 | 9/2009 | Trevejo et al. |
| 2009/0236153 A1 | 9/2009 | Kyung et al. |
| 2009/0239252 A1 | 9/2009 | Trevejo et al. |
| 2009/0246139 A1 | 10/2009 | Woods et al. |
| 2009/0251325 A1 | 10/2009 | Smith et al. |
| 2009/0260987 A1 | 10/2009 | Valdes et al. |
| 2009/0277602 A1 | 11/2009 | Yang |
| 2009/0277603 A1 | 11/2009 | Yang |
| 2009/0292469 A1 | 11/2009 | Son et al. |
| 2009/0309016 A1 | 12/2009 | Almirall et al. |
| 2009/0313971 A1 | 12/2009 | Mueller-Stach et al. |
| 2009/0320559 A1 | 12/2009 | Lemieuvre et al. |
| 2009/0321279 A1 | 12/2009 | Holmen et al. |
| 2009/0323055 A1 | 12/2009 | Cole et al. |
| 2010/0001417 A1 | 1/2010 | D'Amico |
| 2010/0002235 A1 | 1/2010 | Willing et al. |
| 2010/0008820 A1 | 1/2010 | Savikko |
| 2010/0024533 A1 | 2/2010 | Kimura et al. |
| 2010/0068821 A1 | 3/2010 | St. Germain |
| 2010/0069726 A1 | 3/2010 | Levinson |
| 2010/0073162 A1 | 3/2010 | Johnson et al. |
| 2010/0073172 A1 | 3/2010 | Lax |
| 2010/0082274 A1 | 4/2010 | Son et al. |
| 2010/0101214 A1 | 4/2010 | Herman et al. |
| 2010/0105311 A1 | 4/2010 | Meneely, Jr. |
| 2010/0111755 A1 | 5/2010 | Bankers et al. |
| 2010/0117828 A1 | 5/2010 | Goldman et al. |
| 2010/0119408 A1 | 5/2010 | Hafer et al. |
| 2010/0139366 A1 | 6/2010 | Krausch |
| 2010/0148946 A1 | 6/2010 | Strombeck et al. |
| 2010/0155691 A1 | 6/2010 | Lee et al. |
| 2010/0162790 A1 | 7/2010 | Ziegler et al. |
| 2010/0163429 A1 | 7/2010 | Chiu et al. |
| 2010/0178211 A1 | 7/2010 | Ushijima |
| 2010/0180667 A1 | 7/2010 | Bender et al. |
| 2010/0187332 A1 | 7/2010 | Ushijima |
| 2010/0188082 A1 | 7/2010 | Morich et al. |
| 2010/0191474 A1 | 7/2010 | Haick |
| 2010/0194574 A1 | 8/2010 | Monk et al. |
| 2010/0199373 A1 | 8/2010 | Bringe et al. |
| 2010/0199638 A1 | 8/2010 | Yoshikawa |
| 2010/0201530 A1 | 8/2010 | Wende |
| 2010/0201531 A1 | 8/2010 | Pakravan et al. |
| 2010/0206039 A1 | 8/2010 | Kates |
| 2010/0211259 A1 | 8/2010 | McClellan |
| 2010/0211290 A1 | 8/2010 | Kidokoro et al. |
| 2010/0218595 A1 | 9/2010 | Dikken et al. |
| 2010/0218683 A1 | 9/2010 | Chung et al. |
| 2010/0219258 A1 | 9/2010 | Starcic |
| 2010/0219259 A1 | 9/2010 | Starcic |
| 2010/0222561 A1 | 9/2010 | Matsunami et al. |
| 2010/0231394 A1 | 9/2010 | Finchum et al. |
| 2010/0235114 A1 | 9/2010 | Levy et al. |
| 2010/0238018 A1 | 9/2010 | Kelly |

(56) References Cited

U.S. PATENT DOCUMENTS

| | | |
|---|---|---|
| 2010/0248268 A1 | 9/2010 | Woods et al. |
| 2010/0248661 A1 | 9/2010 | Bullock |
| 2010/0256954 A1 | 10/2010 | Castella et al. |
| 2010/0269805 A1 | 10/2010 | Fukuda et al. |
| 2010/0280836 A1 | 11/2010 | Lu et al. |
| 2010/0282245 A1 | 11/2010 | Star et al. |
| 2010/0290948 A1 | 11/2010 | Song |
| 2010/0302048 A1 | 12/2010 | Mahajan |
| 2010/0307231 A1 | 12/2010 | Allard et al. |
| 2010/0313630 A1 | 12/2010 | Grozinger |
| 2010/0315247 A1 | 12/2010 | Tseng |
| 2010/0330515 A1 | 12/2010 | Ueki et al. |
| 2011/0001625 A1 | 1/2011 | Reilly, Jr. et al. |
| 2011/0005207 A1 | 1/2011 | Akihisa et al. |
| 2011/0008212 A1 | 1/2011 | Ichimura |
| 2011/0013189 A1 | 1/2011 | Johansen et al. |
| 2011/0015496 A1 | 1/2011 | Sherman et al. |
| 2011/0015824 A1 | 1/2011 | Ante et al. |
| 2011/0016541 A1 | 1/2011 | Weinstein et al. |
| 2011/0030449 A1 | 2/2011 | Hosono et al. |
| 2011/0046916 A1 | 2/2011 | Yu et al. |
| 2011/0061368 A1 | 3/2011 | Miyata et al. |
| 2011/0063116 A1 | 3/2011 | Lepley et al. |
| 2011/0070158 A1 | 3/2011 | Nutt et al. |
| 2011/0084844 A1 | 4/2011 | Carnation |
| 2011/0088451 A1 | 4/2011 | Holmes |
| 2011/0090050 A1 | 4/2011 | MacFarland |
| 2011/0094457 A1 | 4/2011 | Dee et al. |
| 2011/0094459 A1 | 4/2011 | Dee et al. |
| 2011/0100210 A1 | 5/2011 | Streib et al. |
| 2011/0109464 A1 | 5/2011 | Lepley et al. |
| 2011/0112660 A1 | 5/2011 | Bergmann et al. |
| 2011/0113854 A1 | 5/2011 | Kammerer et al. |
| 2011/0114511 A1 | 5/2011 | Sjong |
| 2011/0142719 A1 | 6/2011 | Goldstein et al. |
| 2011/0144515 A1 | 6/2011 | Bayer et al. |
| 2011/0166769 A1 | 7/2011 | Buechler et al. |
| 2011/0170377 A1 | 7/2011 | Legaspi |
| 2011/0182918 A1 | 7/2011 | Kalnik et al. |
| 2011/0185787 A1 | 8/2011 | Briens et al. |
| 2011/0187542 A1 | 8/2011 | Dittmer et al. |
| 2011/0187543 A1 | 8/2011 | Russo et al. |
| 2011/0200488 A1 | 8/2011 | Cennini et al. |
| 2011/0202260 A1 | 8/2011 | Cunningham et al. |
| 2011/0203349 A1 | 8/2011 | Reese |
| 2011/0212376 A1 | 9/2011 | Carney |
| 2011/0226774 A1 | 9/2011 | Kurz et al. |
| 2011/0226864 A1 | 9/2011 | Kim et al. |
| 2011/0232269 A1 | 9/2011 | Inoue |
| 2011/0233288 A1 | 9/2011 | Doll |
| 2011/0243788 A1 | 10/2011 | Garten |
| 2011/0253359 A1 | 10/2011 | Stockton |
| 2011/0253797 A1 | 10/2011 | Weening et al. |
| 2011/0258992 A1 | 10/2011 | Gonze et al. |
| 2011/0259336 A1 | 10/2011 | Lundeen |
| 2011/0260875 A1 | 10/2011 | Aarts et al. |
| 2011/0271914 A1 | 11/2011 | Richardson et al. |
| 2011/0283770 A1 | 11/2011 | Hok |
| 2011/0284653 A1 | 11/2011 | Butler et al. |
| 2011/0295087 A1 | 12/2011 | Shinoda et al. |
| 2011/0296816 A1 | 12/2011 | Parmentier et al. |
| 2011/0310391 A1 | 12/2011 | Janssen et al. |
| 2011/0312102 A1 | 12/2011 | Jo |
| 2011/0317007 A1 | 12/2011 | Kim |
| 2012/0003746 A1 | 1/2012 | Amisar |
| 2012/0014839 A1 | 1/2012 | Pen |
| 2012/0016252 A1 | 1/2012 | Melker et al. |
| 2012/0031167 A1 | 2/2012 | Chen et al. |
| 2012/0046881 A1 | 2/2012 | Cannon |
| 2012/0047996 A1 | 3/2012 | Reese |
| 2012/0086576 A1 | 4/2012 | Lin |
| 2012/0090385 A1 | 4/2012 | Michel et al. |
| 2012/0091355 A1 | 4/2012 | Rao et al. |
| 2012/0103805 A1 | 5/2012 | Holmen et al. |
| 2012/0112920 A1 | 5/2012 | Ramdeo |
| 2012/0118044 A1 | 5/2012 | Choi et al. |
| 2012/0121511 A1 | 5/2012 | Schmidt et al. |
| 2012/0122079 A1 | 5/2012 | Schmidt et al. |
| 2012/0131905 A1 | 5/2012 | Kwon |
| 2012/0134876 A1 | 5/2012 | Elrod |
| 2012/0150755 A1 | 6/2012 | Kumar et al. |
| 2012/0171776 A1 | 7/2012 | Jayaraman et al. |
| 2012/0179388 A1 | 7/2012 | Kuczynski et al. |
| 2012/0180455 A1 | 7/2012 | Severin et al. |
| 2012/0191288 A1 | 7/2012 | Qi et al. |
| 2012/0210700 A1 | 8/2012 | Sisken et al. |
| 2012/0211515 A1 | 8/2012 | An et al. |
| 2012/0211523 A1 | 8/2012 | An et al. |
| 2012/0219459 A1 | 8/2012 | Nakatani |
| 2012/0222402 A1 | 9/2012 | Keller et al. |
| 2012/0224994 A1 | 9/2012 | Steiner |
| 2012/0230864 A1 | 9/2012 | An et al. |
| 2012/0268268 A1 | 10/2012 | Bargero |
| 2012/0268280 A1 | 10/2012 | Hatch et al. |
| 2012/0288950 A1 | 11/2012 | Zang et al. |
| 2012/0309048 A1 | 12/2012 | Ratcliffe et al. |
| 2012/0325184 A1 | 12/2012 | Janssen et al. |
| 2013/0005414 A1 | 1/2013 | Bindra et al. |
| 2013/0009785 A1 | 1/2013 | Finn et al. |
| 2013/0017120 A1 | 1/2013 | Goldstein et al. |
| 2013/0019653 A1 | 1/2013 | Nakata |
| 2013/0021160 A1 | 1/2013 | Sid |
| 2013/0036811 A1 | 2/2013 | Boult |
| 2013/0047841 A1 | 2/2013 | Zidat |
| 2013/0050466 A1 | 2/2013 | Cetin et al. |
| 2013/0055619 A1 | 3/2013 | Stewart |
| 2013/0056555 A1 | 3/2013 | Yuhki et al. |
| 2013/0059799 A1 | 3/2013 | Liu et al. |
| 2013/0062200 A1 | 3/2013 | Sasaki |
| 2013/0063259 A1 | 3/2013 | Kramer et al. |
| 2013/0066349 A1 | 3/2013 | Fink et al. |
| 2013/0077797 A1 | 3/2013 | Hoy et al. |
| 2013/0081541 A1 | 4/2013 | Hasenoehrl et al. |
| 2013/0090866 A1 | 4/2013 | Ante et al. |
| 2013/0093593 A1 | 4/2013 | Woods |
| 2013/0097999 A1 | 4/2013 | Bouvier et al. |
| 2013/0120788 A1 | 5/2013 | Wang |
| 2013/0123991 A1 | 5/2013 | Richmond |
| 2013/0134342 A1 | 5/2013 | Shiffer |
| 2013/0171733 A1 | 7/2013 | Haick et al. |
| 2013/0175168 A1 | 7/2013 | Nemes |
| 2013/0188544 A1 | 7/2013 | Tiwari et al. |
| 2013/0194089 A1 | 8/2013 | Estrada |
| 2013/0198670 A1 | 8/2013 | Pelletier et al. |
| 2013/0201024 A1 | 8/2013 | Greenwood et al. |
| 2013/0201316 A1 | 8/2013 | Binder et al. |
| 2013/0208114 A1 | 8/2013 | Balsam |
| 2013/0231846 A1 | 9/2013 | Magner et al. |
| 2013/0241727 A1 | 9/2013 | Coulombe |
| 2013/0244336 A1 | 9/2013 | Mayer et al. |
| 2013/0245919 A1 | 9/2013 | Kumar et al. |
| 2013/0263645 A1 | 10/2013 | Jones |
| 2013/0268177 A1 | 10/2013 | Wu et al. |
| 2013/0277389 A1 | 10/2013 | Helf et al. |
| 2013/0286213 A1 | 10/2013 | Cetin et al. |
| 2013/0292484 A1 | 11/2013 | Jackson et al. |
| 2013/0297192 A1 | 11/2013 | Imeroski |
| 2013/0300574 A1 | 11/2013 | Gillette, II |
| 2013/0301674 A1 | 11/2013 | Gillette, II |
| 2013/0304352 A1 | 11/2013 | Macfarlane et al. |
| 2013/0309713 A1 | 11/2013 | Ribble et al. |
| 2013/0316926 A1 | 11/2013 | Caffrey |
| 2013/0318948 A1 | 12/2013 | Van Marion |
| 2013/0324617 A1 | 12/2013 | Dannenberg et al. |
| 2013/0327141 A1 | 12/2013 | Floyd, Jr. et al. |
| 2013/0340408 A1 | 12/2013 | Narayanaswamy et al. |
| 2014/0017989 A1 | 1/2014 | Ganesan et al. |
| 2014/0022968 A1 | 1/2014 | Apte et al. |
| 2014/0024960 A1 | 1/2014 | Smith et al. |
| 2014/0034284 A1 | 2/2014 | Butler et al. |
| 2014/0044425 A1 | 2/2014 | Beesley |
| 2014/0049642 A1 | 2/2014 | Jiang et al. |
| 2014/0055619 A1 | 2/2014 | Holland et al. |
| 2014/0060452 A1 | 3/2014 | Linssen et al. |

(56) References Cited

U.S. PATENT DOCUMENTS

| | | |
|---|---|---|
| 2014/0066003 A1 | 3/2014 | Emerson et al. |
| 2014/0066329 A1 | 3/2014 | Hirschowitz et al. |
| 2014/0069420 A1 | 3/2014 | Richter et al. |
| 2014/0074383 A1 | 3/2014 | Frey |
| 2014/0087369 A1 | 3/2014 | Schmidt et al. |
| 2014/0097953 A1 | 4/2014 | Jelveh et al. |
| 2014/0098445 A1 | 4/2014 | Hooper |
| 2014/0102443 A1 | 4/2014 | Chambers |
| 2014/0104067 A1 | 4/2014 | Chien |
| 2014/0127326 A1 | 5/2014 | Sood et al. |
| 2014/0163841 A1 | 6/2014 | Sane |
| 2014/0170194 A1 | 6/2014 | Cetti et al. |
| 2014/0188287 A1 | 7/2014 | Sabata |
| 2014/0202139 A1 | 7/2014 | Qi et al. |
| 2014/0202655 A1 | 7/2014 | Yang |
| 2014/0209192 A1 | 7/2014 | Lawrence |
| 2014/0217292 A1 | 8/2014 | Monros |
| 2014/0225731 A1 | 8/2014 | Gouveia |
| 2014/0238100 A1 | 8/2014 | Londergan et al. |
| 2014/0242562 A1 | 8/2014 | McSterling et al. |
| 2014/0253327 A1 | 9/2014 | Tinaphong et al. |
| 2014/0255258 A1 | 9/2014 | Londos |
| 2014/0266682 A1 | 9/2014 | Gettings et al. |
| 2014/0266747 A1 | 9/2014 | Prendergast |
| 2014/0277927 A1 | 9/2014 | Guo et al. |
| 2014/0278258 A1 | 9/2014 | Shafer |
| 2014/0284222 A1 | 9/2014 | Wanek, Jr. et al. |
| 2014/0284390 A1 | 9/2014 | Teng et al. |
| 2014/0294675 A1 | 10/2014 | Melker et al. |
| 2014/0294796 A1 | 10/2014 | Wilson et al. |
| 2014/0313040 A1 | 10/2014 | Wright, Sr. |
| 2014/0320296 A1 | 10/2014 | Thurber et al. |
| 2014/0322082 A1 | 10/2014 | Hasenoehrl et al. |
| 2014/0333442 A1 | 11/2014 | Carney |
| 2014/0338426 A1 | 11/2014 | Noda et al. |
| 2014/0343822 A1 | 11/2014 | Varney |
| 2014/0349566 A1 | 11/2014 | Lamb et al. |
| 2014/0360213 A1 | 12/2014 | Son et al. |
| 2014/0364330 A1 | 12/2014 | Mershin et al. |
| 2014/0366515 A1 | 12/2014 | Kowalkowski et al. |
| 2014/0367408 A1 | 12/2014 | D'Amico |
| 2014/0368354 A1 | 12/2014 | Skourlis |
| 2014/0375464 A1 | 12/2014 | Caragata |
| 2015/0014167 A1 | 1/2015 | Dziallas et al. |
| 2015/0022340 A1 | 1/2015 | Gettings et al. |
| 2015/0031582 A1 | 1/2015 | Cai et al. |
| 2015/0032019 A1 | 1/2015 | Acker et al. |
| 2015/0034484 A1 | 2/2015 | Nakasone et al. |
| 2015/0041682 A1 | 2/2015 | Cano et al. |
| 2015/0042469 A1 | 2/2015 | Baldocchi et al. |
| 2015/0047339 A1 | 2/2015 | Rollinger et al. |
| 2015/0056912 A1 | 2/2015 | Scipio et al. |
| 2015/0065030 A1 | 3/2015 | Kates |
| 2015/0065437 A1 | 3/2015 | Liu et al. |
| 2015/0077248 A1 | 3/2015 | Eck |
| 2015/0078964 A1 | 3/2015 | Meirav et al. |
| 2015/0080265 A1 | 3/2015 | Elzinga et al. |
| 2015/0090020 A1 | 4/2015 | Takita et al. |
| 2015/0090194 A1 | 4/2015 | Pearce et al. |
| 2015/0098860 A1 | 4/2015 | Aldereguia et al. |
| 2015/0098867 A1 | 4/2015 | Aldereguia et al. |
| 2015/0108241 A1 | 4/2015 | Chase et al. |
| 2015/0136616 A1 | 5/2015 | Friedrich |
| 2015/0140919 A1 | 5/2015 | Zwijack |
| 2015/0147818 A1 | 5/2015 | Kim et al. |
| 2015/0161452 A1 | 6/2015 | McCarthy, III et al. |
| 2015/0170490 A1 | 6/2015 | Shaw |
| 2015/0177202 A1 | 6/2015 | Ozbek et al. |
| 2015/0185192 A1 | 7/2015 | Holmes |
| 2015/0187194 A1 | 7/2015 | Hypolite et al. |
| 2015/0192048 A1 | 7/2015 | Tanioka |
| 2015/0199894 A1 | 7/2015 | Braun et al. |
| 2015/0206151 A1 | 7/2015 | Carney et al. |
| 2015/0211885 A1 | 7/2015 | Rutherford et al. |
| 2015/0212057 A1 | 7/2015 | Darveau |
| 2015/0235539 A1 | 8/2015 | Orvis et al. |
| 2015/0235540 A1 | 8/2015 | Verna et al. |
| 2015/0240772 A1 | 8/2015 | Yamamoto et al. |
| 2015/0250911 A1 | 9/2015 | Bieri et al. |
| 2015/0268210 A1 | 9/2015 | Cristoforo |
| 2015/0271201 A1 | 9/2015 | Ruvio et al. |
| 2015/0273395 A1 | 10/2015 | Catalogna et al. |
| 2015/0275804 A1 | 10/2015 | Takano et al. |
| 2015/0276693 A1 | 10/2015 | Sid |
| 2015/0289782 A1 | 10/2015 | Peverall et al. |
| 2015/0295562 A1 | 10/2015 | Agarwal et al. |
| 2015/0297778 A1 | 10/2015 | Conroy et al. |
| 2015/0302728 A1 | 10/2015 | Gettings et al. |
| 2015/0315967 A1 | 11/2015 | Tuero |
| 2015/0323941 A1 | 11/2015 | Pariseau et al. |
| 2015/0346175 A1 | 12/2015 | Monros |
| 2015/0348220 A1 | 12/2015 | Sharma et al. |
| 2015/0355151 A1 | 12/2015 | Cleary |
| 2015/0364340 A1 | 12/2015 | Ueda |
| 2015/0369774 A1 | 12/2015 | Rabbett |
| 2015/0372832 A1 | 12/2015 | Kortz et al. |
| 2015/0377102 A1 | 12/2015 | Yezerets et al. |
| 2016/0000956 A1 | 1/2016 | Jenkins et al. |
| 2016/0003180 A1 | 1/2016 | McNulty et al. |
| 2016/0003805 A1 | 1/2016 | Ray et al. |
| 2016/0012714 A1 | 1/2016 | Patenaude et al. |
| 2016/0022854 A1 | 1/2016 | Shah |
| 2016/0029693 A1 | 2/2016 | Klein et al. |
| 2016/0032812 A1 | 2/2016 | Lee |
| 2016/0049059 A1 | 2/2016 | Engelmann et al. |
| 2016/0054046 A1 | 2/2016 | Sim |
| 2016/0060355 A1 | 3/2016 | Bhatnagar et al. |
| 2016/0061087 A1 | 3/2016 | Nagaoka |
| 2016/0061476 A1 | 3/2016 | Schultz et al. |
| 2016/0061477 A1 | 3/2016 | Schultz et al. |
| 2016/0061794 A1 | 3/2016 | Schultz et al. |
| 2016/0061795 A1 | 3/2016 | Schultz et al. |
| 2016/0065414 A1 | 3/2016 | Sundermeyer et al. |
| 2016/0066067 A1 | 3/2016 | Schultz et al. |
| 2016/0069580 A1 | 3/2016 | Crisa' |
| 2016/0077071 A1 | 3/2016 | Chancey |
| 2016/0084136 A1 | 3/2016 | Liu et al. |
| 2016/0093187 A1 | 3/2016 | Zhang et al. |
| 2016/0097534 A1 | 4/2016 | De Vries |
| 2016/0097748 A1 | 4/2016 | Hansen et al. |
| 2016/0116913 A1 | 4/2016 | Niles |
| 2016/0123587 A1 | 5/2016 | Ventura |
| 2016/0125714 A1 | 5/2016 | Kates et al. |
| 2016/0133108 A1 | 5/2016 | Bucsa et al. |
| 2016/0144064 A1 | 5/2016 | Santini et al. |
| 2016/0146121 A1 | 5/2016 | Carlson et al. |
| 2016/0146751 A1 | 5/2016 | Nemes |
| 2016/0169851 A1 | 6/2016 | Lee et al. |
| 2016/0178228 A1 | 6/2016 | Shahabdeen |
| 2016/0186636 A1 | 6/2016 | Odendall |
| 2016/0202201 A1 | 7/2016 | Cobianu et al. |
| 2016/0213800 A1 | 7/2016 | Tedesco |
| 2016/0216174 A1 | 7/2016 | Cloudt et al. |
| 2016/0216244 A1 | 7/2016 | Sobel et al. |
| 2016/0223487 A1 | 8/2016 | Okamoto et al. |
| 2016/0225481 A1 | 8/2016 | Yoon et al. |
| 2016/0237732 A1 | 8/2016 | Kerley |
| 2016/0247369 A1 | 8/2016 | Simmons |
| 2016/0253887 A1 | 9/2016 | Webb |
| 2016/0256485 A1 | 9/2016 | Wager et al. |
| 2016/0258919 A1 | 9/2016 | Allyn |
| 2016/0269533 A1 | 9/2016 | Taylor et al. |
| 2016/0272112 A1 | 9/2016 | DeGrazia et al. |
| 2016/0273437 A1 | 9/2016 | Devarakonda |
| 2016/0279574 A1 | 9/2016 | Devarakonda |
| 2016/0281623 A1 | 9/2016 | Knuebel et al. |
| 2016/0284176 A1 | 9/2016 | Harrington et al. |
| 2016/0319727 A1 | 11/2016 | Nikolaus et al. |
| 2016/0320308 A1 | 11/2016 | Liss |
| 2016/0321879 A1 | 11/2016 | Oh et al. |
| 2016/0321899 A1 | 11/2016 | Mingo |
| 2016/0327298 A1 | 11/2016 | Sinha et al. |
| 2016/0349216 A1 | 12/2016 | Ichimura et al. |
| 2016/0350715 A1 | 12/2016 | Minvielle |

(56) References Cited

U.S. PATENT DOCUMENTS

| | | |
|---|---|---|
| 2016/0368304 A1 | 12/2016 | Mahbubani et al. |
| 2016/0370255 A1 | 12/2016 | Zahdeh et al. |
| 2016/0370331 A1 | 12/2016 | Nakada et al. |
| 2016/0371969 A1 | 12/2016 | Rossi et al. |
| 2016/0376309 A1 | 12/2016 | Liu et al. |
| 2016/0377583 A1 | 12/2016 | Takahashi |
| 2017/0003179 A1 | 1/2017 | Jin |
| 2017/0003238 A1 | 1/2017 | Salvador et al. |
| 2017/0003246 A1 | 1/2017 | Shuk et al. |
| 2017/0011673 A1 | 1/2017 | Condor |
| 2017/0016906 A1 | 1/2017 | Hirotsu et al. |
| 2017/0018158 A1 | 1/2017 | Sayavong et al. |
| 2017/0045472 A1 | 2/2017 | Zanon et al. |
| 2017/0049597 A1 | 2/2017 | Manne |
| 2017/0051653 A1 | 2/2017 | Martin et al. |
| 2017/0052545 A1 | 2/2017 | Cortez |
| 2017/0056821 A1 | 3/2017 | Beaulieu et al. |
| 2017/0067659 A1 | 3/2017 | Silver et al. |
| 2017/0069190 A1 | 3/2017 | Hansen et al. |
| 2017/0073614 A1 | 3/2017 | Alchenberger et al. |
| 2017/0076403 A1 | 3/2017 | Edwards et al. |
| 2017/0078400 A1 | 3/2017 | Binder et al. |
| 2017/0080373 A1 | 3/2017 | Engelhard |
| 2017/0082305 A1 | 3/2017 | Law |
| 2017/0082574 A1 | 3/2017 | Byun et al. |
| 2017/0089247 A1 | 3/2017 | Liu et al. |
| 2017/0096955 A1 | 4/2017 | Jung |
| 2017/0098121 A1 | 4/2017 | Ur |
| 2017/0101941 A1 | 4/2017 | Gladel et al. |
| 2017/0102337 A1 | 4/2017 | Benson et al. |
| 2017/0113512 A1* | 4/2017 | Park .................. G06V 40/18 |
| 2017/0119919 A1 | 5/2017 | Hsiao |
| 2017/0122616 A1 | 5/2017 | Calabro |
| 2017/0130439 A1 | 5/2017 | Kleinsasser et al. |
| 2017/0130986 A1 | 5/2017 | Wang et al. |
| 2017/0140619 A1 | 5/2017 | Russo et al. |
| 2017/0157221 A1 | 6/2017 | Fallon |
| 2017/0175661 A1 | 6/2017 | Kumar et al. |
| 2017/0177815 A1 | 6/2017 | Sundararajan et al. |
| 2017/0184560 A1 | 6/2017 | Crescini et al. |
| 2017/0192399 A1 | 7/2017 | Ramakrishnappa et al. |
| 2017/0193788 A1 | 7/2017 | Kim et al. |
| 2017/0193789 A1 | 7/2017 | Economy et al. |
| 2017/0193798 A1 | 7/2017 | Call et al. |
| 2017/0209338 A1 | 7/2017 | Potucek et al. |
| 2017/0210286 A1 | 7/2017 | Kasin |
| 2017/0216892 A1 | 8/2017 | Campanella et al. |
| 2017/0226282 A1 | 8/2017 | Deb |
| 2017/0227491 A1 | 8/2017 | Johnson et al. |
| 2017/0232130 A1 | 8/2017 | Conroy et al. |
| 2017/0233679 A1 | 8/2017 | Cetti et al. |
| 2017/0234197 A1 | 8/2017 | Dean |
| 2017/0241321 A1 | 8/2017 | Yoo et al. |
| 2017/0241964 A1 | 8/2017 | Vereecken et al. |
| 2017/0242004 A1 | 8/2017 | Hanson et al. |
| 2017/0246334 A1 | 8/2017 | Krishnan et al. |
| 2017/0248541 A1 | 8/2017 | Liu |
| 2017/0261485 A1 | 9/2017 | Panella et al. |
| 2017/0266334 A1 | 9/2017 | Tranzeat et al. |
| 2017/0274737 A1 | 9/2017 | Delaruelle |
| 2017/0284689 A1 | 10/2017 | Steele et al. |
| 2017/0284690 A1 | 10/2017 | Lipanov |
| 2017/0284694 A1 | 10/2017 | Park et al. |
| 2017/0290294 A1 | 10/2017 | Linssen et al. |
| 2017/0311845 A1 | 11/2017 | Cho et al. |
| 2017/0315083 A1 | 11/2017 | Bather et al. |
| 2017/0315103 A1 | 11/2017 | Biswas et al. |
| 2017/0315107 A1 | 11/2017 | Chou et al. |
| 2017/0322167 A1 | 11/2017 | Swager et al. |
| 2017/0322181 A1 | 11/2017 | White et al. |
| 2017/0324936 A1 | 11/2017 | Tran et al. |
| 2017/0328259 A1 | 11/2017 | Uchiyama et al. |
| 2017/0328294 A1 | 11/2017 | Poloni et al. |
| 2017/0328816 A1 | 11/2017 | Remondini |
| 2017/0328877 A1 | 11/2017 | Bajaj |
| 2017/0335781 A1 | 11/2017 | Augusty |
| 2017/0342927 A1 | 11/2017 | Miyamoto et al. |
| 2017/0343501 A1 | 11/2017 | Serban et al. |
| 2017/0343517 A1 | 11/2017 | Le Calve et al. |
| 2017/0343521 A1 | 11/2017 | Chang et al. |
| 2017/0352236 A1 | 12/2017 | Moses |
| 2017/0352243 A1 | 12/2017 | Quanci et al. |
| 2017/0354231 A1 | 12/2017 | Okumura et al. |
| 2017/0363046 A1 | 12/2017 | Dudar et al. |
| 2017/0365151 A1 | 12/2017 | Burleson |
| 2017/0369168 A1 | 12/2017 | Hwang et al. |
| 2017/0370268 A1 | 12/2017 | Meier et al. |
| 2017/0370888 A1 | 12/2017 | Lee et al. |
| 2018/0003644 A1 | 1/2018 | Christiansen |
| 2018/0010994 A1 | 1/2018 | Macomber |
| 2018/0021467 A1 | 1/2018 | Mainland et al. |
| 2018/0027907 A1 | 2/2018 | Singer |
| 2018/0038825 A1 | 2/2018 | Ratto et al. |
| 2018/0040232 A1 | 2/2018 | Wedig et al. |
| 2018/0044258 A1 | 2/2018 | Hahma et al. |
| 2018/0050230 A1 | 2/2018 | Toland |
| 2018/0050330 A1 | 2/2018 | Ishitani |
| 2018/0050575 A1 | 2/2018 | Campbell et al. |
| 2018/0052655 A1 | 2/2018 | Hannibal, III et al. |
| 2018/0053140 A1 | 2/2018 | Baca et al. |
| 2018/0055134 A1 | 3/2018 | Zhang |
| 2018/0055288 A1 | 3/2018 | Rose et al. |
| 2018/0055488 A1 | 3/2018 | Hall et al. |
| 2018/0067091 A1 | 3/2018 | Burkhalter et al. |
| 2018/0073759 A1 | 3/2018 | Zhang et al. |
| 2018/0075724 A1 | 3/2018 | Steiner et al. |
| 2018/0078899 A1 | 3/2018 | Remondini |
| 2018/0078954 A1 | 3/2018 | Gruenbacher et al. |
| 2018/0080846 A1 | 3/2018 | Zhang et al. |
| 2018/0080912 A1 | 3/2018 | Abbott et al. |
| 2018/0087432 A1 | 3/2018 | Odendall |
| 2018/0087460 A1 | 3/2018 | Pathan et al. |
| 2018/0094564 A1 | 4/2018 | Okamoto et al. |
| 2018/0095061 A1 | 4/2018 | Kane et al. |
| 2018/0106755 A1 | 4/2018 | Kayama et al. |
| 2018/0108234 A1 | 4/2018 | Cichon |
| 2018/0110006 A1 | 4/2018 | Kates |
| 2018/0110457 A1 | 4/2018 | Smith et al. |
| 2018/0114430 A1 | 4/2018 | Westmacott et al. |
| 2018/0119973 A1 | 5/2018 | Rothman et al. |
| 2018/0120277 A1 | 5/2018 | Chang et al. |
| 2018/0120278 A1 | 5/2018 | Hoorfar et al. |
| 2018/0125374 A1 | 5/2018 | Hall et al. |
| 2018/0128145 A1 | 5/2018 | Uhrich et al. |
| 2018/0128771 A1 | 5/2018 | Okamoto et al. |
| 2018/0134112 A1 | 5/2018 | Seiferlein et al. |
| 2018/0135541 A1 | 5/2018 | Hsieh et al. |
| 2018/0135542 A1 | 5/2018 | Baek et al. |
| 2018/0136119 A1 | 5/2018 | Pi |
| 2018/0136187 A1 | 5/2018 | Doutt et al. |
| 2018/0141498 A1 | 5/2018 | Savage |
| 2018/0142590 A1 | 5/2018 | Gupta et al. |
| 2018/0142639 A1 | 5/2018 | Miyamoto et al. |
| 2018/0151061 A1 | 5/2018 | Lauren |
| 2018/0156096 A1 | 6/2018 | Mitchell et al. |
| 2018/0158309 A1 | 6/2018 | Steins |
| 2018/0164264 A1 | 6/2018 | Savage |
| 2018/0164273 A1 | 6/2018 | Sieben et al. |
| 2018/0171146 A1 | 6/2018 | Allen et al. |
| 2018/0172652 A1 | 6/2018 | Voutilainen |
| 2018/0178613 A1 | 6/2018 | Zhang et al. |
| 2018/0179979 A1 | 6/2018 | Miyamoto et al. |
| 2018/0180493 A1 | 6/2018 | Ishiguro et al. |
| 2018/0182218 A1 | 6/2018 | Toland |
| 2018/0186198 A1 | 7/2018 | Zhou et al. |
| 2018/0188152 A1 | 7/2018 | Vercruysse |
| 2018/0188235 A1 | 7/2018 | Ray et al. |
| 2018/0189714 A1 | 7/2018 | Azpitarte et al. |
| 2018/0195988 A1 | 7/2018 | Salvador et al. |
| 2018/0195990 A1 | 7/2018 | Yassine et al. |
| 2018/0199921 A1 | 7/2018 | Hall et al. |
| 2018/0202890 A1 | 7/2018 | Mutch et al. |
| 2018/0202986 A1 | 7/2018 | Knoefler et al. |
| 2018/0204441 A1 | 7/2018 | Zribi et al. |

(56) References Cited

U.S. PATENT DOCUMENTS

| | | |
|---|---|---|
| 2018/0208637 A1 | 7/2018 | Pfister et al. |
| 2018/0209978 A1 | 7/2018 | Postrel |
| 2018/0211512 A1 | 7/2018 | Zribi et al. |
| 2018/0217131 A1 | 8/2018 | Yu |
| 2018/0223712 A1 | 8/2018 | Ren et al. |
| 2018/0224403 A1 | 8/2018 | Ji et al. |
| 2018/0225956 A1 | 8/2018 | Chen |
| 2018/0230879 A1 | 8/2018 | Saitoh et al. |
| 2018/0231515 A1 | 8/2018 | Voumard |
| 2018/0236119 A1 | 8/2018 | Shah |
| 2018/0245393 A1 | 8/2018 | Ozkan |
| 2018/0249735 A1 | 9/2018 | Espinosa |
| 2018/0249758 A1 | 9/2018 | Derkalousdian et al. |
| 2018/0250430 A1 | 9/2018 | Machovina et al. |
| 2018/0252669 A1 | 9/2018 | Oh et al. |
| 2018/0252701 A1 | 9/2018 | Rhodes et al. |
| 2018/0258821 A1 | 9/2018 | Masubuchi et al. |
| 2018/0260686 A1 | 9/2018 | Tommy et al. |
| 2018/0264156 A1 | 9/2018 | O'Leary et al. |
| 2018/0264299 A1 | 9/2018 | Combe |
| 2018/0266163 A1 | 9/2018 | Combe |
| 2018/0266169 A1 | 9/2018 | Wray et al. |
| 2018/0266977 A1 | 9/2018 | Hashizume |
| 2018/0267017 A1 | 9/2018 | Love |
| 2018/0271406 A1 | 9/2018 | Furusaki et al. |
| 2018/0273890 A1 | 9/2018 | Shkolnikov et al. |
| 2018/0274839 A1 | 9/2018 | Kim et al. |
| 2018/0276983 A1 | 9/2018 | Tani et al. |
| 2018/0282155 A1 | 10/2018 | Haick |
| 2018/0282588 A1 | 10/2018 | Arigo et al. |
| 2018/0283248 A1 | 10/2018 | Upadhyay et al. |
| 2018/0283308 A1 | 10/2018 | Hayashita et al. |
| 2018/0284048 A1 | 10/2018 | Wakana et al. |
| 2018/0285923 A1 | 10/2018 | Fateh |
| 2018/0290104 A1 | 10/2018 | Jong |
| 2018/0292286 A1 | 10/2018 | Dittberner et al. |
| 2018/0292309 A1 | 10/2018 | Prasad |
| 2018/0292374 A1 | 10/2018 | Dittberner et al. |
| 2018/0292520 A1 | 10/2018 | Bermudez et al. |
| 2018/0296650 A1 | 10/2018 | Fallon |
| 2018/0296719 A1 | 10/2018 | Lane et al. |
| 2018/0299150 A1 | 10/2018 | Ajax et al. |
| 2018/0299151 A1 | 10/2018 | Ajax et al. |
| 2018/0299156 A1 | 10/2018 | Ajax et al. |
| 2018/0299159 A1 | 10/2018 | Ajax et al. |
| 2018/0303963 A1 | 10/2018 | Park et al. |
| 2018/0305010 A1 | 10/2018 | Baracaldo Angel et al. |
| 2018/0305734 A1 | 10/2018 | Sato et al. |
| 2018/0308340 A1 | 10/2018 | Thiyagarajah et al. |
| 2018/0312562 A1 | 11/2018 | Zhang et al. |
| 2018/0318189 A1 | 11/2018 | Hatt et al. |
| 2018/0320646 A1 | 11/2018 | Naclerio |
| 2018/0320916 A1 | 11/2018 | Vincitore et al. |
| 2018/0322405 A1 | 11/2018 | Fadell et al. |
| 2018/0334010 A1* | 11/2018 | Wang ................ B60H 1/00864 |
| 2018/0335409 A1 | 11/2018 | Kao et al. |
| 2018/0335413 A1 | 11/2018 | Jouper |
| 2018/0346130 A1 | 12/2018 | Jouper |
| 2018/0350220 A1 | 12/2018 | Gonzales |
| 2018/0353891 A1 | 12/2018 | Cho et al. |
| 2018/0356357 A1 | 12/2018 | Samarao |
| 2018/0356383 A1 | 12/2018 | Phelipot et al. |
| 2018/0357871 A1 | 12/2018 | Siminoff |
| 2018/0362579 A1 | 12/2018 | Wilson et al. |
| 2018/0363577 A1 | 12/2018 | Ulrey et al. |
| 2018/0369442 A1 | 12/2018 | Kelsen |
| 2018/0369847 A1 | 12/2018 | Kihm et al. |
| 2018/0372011 A1 | 12/2018 | Hagari |
| 2018/0372330 A1 | 12/2018 | Ronda et al. |
| 2018/0372637 A1 | 12/2018 | He et al. |
| 2018/0375820 A1 | 12/2018 | Smith et al. |
| 2019/0001015 A1 | 1/2019 | Fiedler et al. |
| 2019/0002952 A1 | 1/2019 | Rodenrys |
| 2019/0003480 A1 | 1/2019 | Hall et al. |
| 2019/0004021 A1 | 1/2019 | Yu |
| 2019/0005811 A1 | 1/2019 | Saia et al. |
| 2019/0011336 A1 | 1/2019 | Mou et al. |
| 2019/0011390 A1 | 1/2019 | Mou et al. |
| 2019/0011391 A1 | 1/2019 | Mou et al. |
| 2019/0011392 A1 | 1/2019 | Mou et al. |
| 2019/0011394 A1 | 1/2019 | Mou et al. |
| 2019/0011949 A1 | 1/2019 | Mou et al. |
| 2019/0017427 A1 | 1/2019 | Dudar |
| 2019/0017453 A1 | 1/2019 | Dudar |
| 2019/0018378 A1 | 1/2019 | Varikooty et al. |
| 2019/0019033 A1 | 1/2019 | Chang et al. |
| 2019/0022132 A1 | 1/2019 | Wager et al. |
| 2019/0025243 A1 | 1/2019 | Yu et al. |
| 2019/0025246 A1 | 1/2019 | Liu et al. |
| 2019/0025264 A1 | 1/2019 | Peng et al. |
| 2019/0033170 A1 | 1/2019 | Dudar |
| 2019/0033177 A1 | 1/2019 | Mou et al. |
| 2019/0033253 A1 | 1/2019 | Yu et al. |
| 2019/0033278 A1 | 1/2019 | Mou et al. |
| 2019/0033280 A1 | 1/2019 | Mou et al. |
| 2019/0033290 A1 | 1/2019 | Koo et al. |
| 2019/0041370 A1 | 2/2019 | Gao et al. |
| 2019/0041371 A1 | 2/2019 | Dinsmore |
| 2019/0051639 A1 | 2/2019 | Hussain et al. |
| 2019/0056125 A1 | 2/2019 | Mou et al. |
| 2019/0056292 A1 | 2/2019 | Mou et al. |
| 2019/0056366 A1 | 2/2019 | Mou et al. |
| 2019/0056367 A1 | 2/2019 | Mou et al. |
| 2019/0056368 A1 | 2/2019 | Mou et al. |
| 2019/0056369 A1 | 2/2019 | Mou et al. |
| 2019/0056766 A1 | 2/2019 | Mou et al. |
| 2019/0059725 A1 | 2/2019 | Greiner |
| 2019/0060821 A1 | 2/2019 | Mou et al. |
| 2019/0061466 A1 | 2/2019 | MacNeille et al. |
| 2019/0063421 A1 | 2/2019 | Mou et al. |
| 2019/0063678 A1 | 2/2019 | Ganiger et al. |
| 2019/0063762 A1 | 2/2019 | Lee et al. |
| 2019/0064104 A1 | 2/2019 | Mou et al. |
| 2019/0064134 A1 | 2/2019 | Mou et al. |
| 2019/0066483 A1 | 2/2019 | Darling et al. |
| 2019/0066488 A1 | 2/2019 | Locke et al. |
| 2019/0069516 A1 | 3/2019 | Pearce et al. |
| 2019/0070086 A1 | 3/2019 | Cetti et al. |
| 2019/0070547 A1 | 3/2019 | Sappok et al. |
| 2019/0072020 A1 | 3/2019 | Hagiwara et al. |
| 2019/0082737 A1 | 3/2019 | Smith et al. |
| 2019/0086410 A1 | 3/2019 | Wright et al. |
| 2019/0095078 A1 | 3/2019 | Marshall et al. |
| 2019/0097833 A1 | 3/2019 | Doerner et al. |
| 2019/0101033 A1 | 4/2019 | Yoda et al. |
| 2019/0101302 A1 | 4/2019 | Rainone et al. |
| 2019/0101501 A1 | 4/2019 | Sahu et al. |
| 2019/0101515 A1 | 4/2019 | Konieczka et al. |
| 2019/0105250 A1 | 4/2019 | Singer et al. |
| 2019/0105960 A1 | 4/2019 | Dudar |
| 2019/0106458 A1 | 4/2019 | Liu et al. |
| 2019/0106639 A1 | 4/2019 | Rovani, Jr. et al. |
| 2019/0107081 A1 | 4/2019 | Dudar |
| 2019/0108738 A1 | 4/2019 | Al Hajjaj |
| 2019/0108739 A1 | 4/2019 | Wedig et al. |
| 2019/0112330 A1 | 4/2019 | Wright et al. |
| 2019/0112993 A1 | 4/2019 | Noh et al. |
| 2019/0113491 A1 | 4/2019 | Xie et al. |
| 2019/0113494 A1 | 4/2019 | Desjardins |
| 2019/0114671 A1 | 4/2019 | Briggs et al. |
| 2019/0114891 A1 | 4/2019 | Eck |
| 2019/0114904 A1 | 4/2019 | Subramanian |
| 2019/0117815 A1 | 4/2019 | Wei et al. |
| 2019/0120101 A1 | 4/2019 | Dadam et al. |
| 2019/0124194 A1 | 4/2019 | Stolte |
| 2019/0128780 A1 | 5/2019 | Pilon et al. |
| 2019/0130718 A1 | 5/2019 | Alpert |
| 2019/0135270 A1 | 5/2019 | Dudar |
| 2019/0135271 A1 | 5/2019 | Garcia |
| 2019/0135552 A1 | 5/2019 | Martono et al. |
| 2019/0137464 A1 | 5/2019 | Kasper et al. |
| 2019/0137476 A1 | 5/2019 | Davis et al. |
| 2019/0137480 A1 | 5/2019 | Arregui San Martin et al. |
| 2019/0142326 A1 | 5/2019 | Mills |

(56) References Cited

U.S. PATENT DOCUMENTS

| | | |
|---|---|---|
| 2019/0142329 A1 | 5/2019 | Mills |
| 2019/0144353 A1 | 5/2019 | Wang et al. |
| 2019/0145644 A1 | 5/2019 | Karamanos et al. |
| 2019/0152995 A1 | 5/2019 | Gunasekaran et al. |
| 2019/0154285 A1 | 5/2019 | Pham et al. |
| 2019/0154571 A1 | 5/2019 | Kuczynski et al. |
| 2019/0154645 A1 | 5/2019 | Kim et al. |
| 2019/0156940 A1 | 5/2019 | Jackson |
| 2019/0160195 A1 | 5/2019 | Kelsen |
| 2019/0160425 A1 | 5/2019 | Beaulieu et al. |
| 2019/0160907 A1 | 5/2019 | Velazquez et al. |
| 2019/0162154 A1 | 5/2019 | Pompea et al. |
| 2019/0162159 A1 | 5/2019 | Dudar |
| 2019/0166413 A1 | 5/2019 | Klinger et al. |
| 2019/0167152 A1 | 6/2019 | Weda et al. |
| 2019/0167831 A1 | 6/2019 | Chan et al. |
| 2019/0168711 A1 | 6/2019 | Oesterling et al. |
| 2019/0169916 A1 | 6/2019 | Morgan et al. |
| 2019/0170061 A1 | 6/2019 | Dudar |
| 2019/0170690 A1 | 6/2019 | Qiu et al. |
| 2019/0170691 A1 | 6/2019 | Hsi et al. |
| 2019/0172332 A1 | 6/2019 | Kraz et al. |
| 2019/0172333 A1 | 6/2019 | Combe |
| 2019/0176810 A1 | 6/2019 | Dudar |
| 2019/0178187 A1 | 6/2019 | Smith et al. |
| 2019/0180596 A1 | 6/2019 | Glasgow et al. |
| 2019/0183887 A1 | 6/2019 | Koo et al. |
| 2019/0186392 A1 | 6/2019 | Dudar et al. |
| 2019/0187035 A1 | 6/2019 | Mou et al. |
| 2019/0187120 A1 | 6/2019 | Russell et al. |
| 2019/0195112 A1 | 6/2019 | Negishi et al. |
| 2019/0195160 A1 | 6/2019 | Negishi et al. |
| 2019/0195464 A1 | 6/2019 | Dong et al. |
| 2019/0195828 A1 | 6/2019 | Knoefler et al. |
| 2019/0195845 A1 | 6/2019 | Kim |
| 2019/0195848 A1 | 6/2019 | Mou et al. |
| 2019/0195849 A1 | 6/2019 | Mou et al. |
| 2019/0195850 A1 | 6/2019 | Mou et al. |
| 2019/0197856 A1 | 6/2019 | Gracin |
| 2019/0197858 A1 | 6/2019 | Moses |
| 2019/0197868 A1 | 6/2019 | Guerin |
| 2019/0197876 A1 | 6/2019 | Mullins et al. |
| 2019/0197878 A1 | 6/2019 | Rubio Corredera |
| 2019/0200206 A1 | 6/2019 | Rubio Corredera |
| 2019/0203256 A1 | 7/2019 | Koo et al. |
| 2019/0203300 A1 | 7/2019 | Darling et al. |
| 2019/0203668 A1 | 7/2019 | Dudar et al. |
| 2019/0203959 A1 | 7/2019 | Aleti |
| 2019/0203960 A1 | 7/2019 | Hoyda et al. |
| 2019/0204279 A1 | 7/2019 | Luo |
| 2019/0204282 A1 | 7/2019 | Gong et al. |
| 2019/0209022 A1 | 7/2019 | Sobol et al. |
| 2019/0211736 A1 | 7/2019 | Reitmeier et al. |
| 2019/0211768 A1 | 7/2019 | Dudar |
| 2019/0212012 A1 | 7/2019 | Le |
| 2019/0212242 A1 | 7/2019 | Mou et al. |
| 2019/0213867 A1 | 7/2019 | Tani et al. |
| 2019/0219540 A1 | 7/2019 | Mohanty et al. |
| 2019/0221095 A1 | 7/2019 | Bonnard et al. |
| 2019/0221101 A1 | 7/2019 | Golob |
| 2019/0221108 A1 | 7/2019 | Harris et al. |
| 2019/0225632 A1 | 7/2019 | Braddock-Wilking et al. |
| 2019/0225659 A1 | 7/2019 | Takahashi et al. |
| 2019/0227015 A1 | 7/2019 | Kuczynski et al. |
| 2019/0227042 A1 | 7/2019 | Hashizume et al. |
| 2019/0227044 A1 | 7/2019 | Ando et al. |
| 2019/0227053 A1 | 7/2019 | Rinberg et al. |
| 2019/0230402 A1 | 7/2019 | Fox |
| 2019/0231267 A1 | 8/2019 | Oren et al. |
| 2019/0232951 A1 | 8/2019 | Dudar |
| 2019/0234326 A1 | 8/2019 | Dudar |
| 2019/0234521 A1 | 8/2019 | Halbheer et al. |
| 2019/0234838 A1 | 8/2019 | Mou et al. |
| 2019/0234839 A1 | 8/2019 | Mou et al. |
| 2019/0234840 A1 | 8/2019 | Mou et al. |
| 2019/0234851 A1 | 8/2019 | Mou et al. |
| 2019/0234895 A1 | 8/2019 | Smilanich et al. |
| 2019/0236678 A1 | 8/2019 | Wilkinson et al. |
| 2019/0239564 A1 | 8/2019 | Utley et al. |
| 2019/0242599 A1 | 8/2019 | Sakai et al. |
| 2019/0249622 A1 | 8/2019 | Dudar et al. |
| 2019/0250133 A1 | 8/2019 | Shao et al. |
| 2019/0250136 A1 | 8/2019 | Kim et al. |
| 2019/0250148 A1 | 8/2019 | Matsunami |
| 2019/0251767 A1 | 8/2019 | Makita et al. |
| 2019/0256082 A1 | 8/2019 | Eloy et al. |
| 2019/0257143 A1 | 8/2019 | Nagel et al. |
| 2019/0257235 A1 | 8/2019 | Van Nieuwstadt et al. |
| 2019/0257236 A1 | 8/2019 | Pfister et al. |
| 2019/0257241 A1 | 8/2019 | Heinken |
| 2019/0257543 A1 | 8/2019 | Martin |
| 2019/0258278 A1 | 8/2019 | Zokaei et al. |
| 2019/0263226 A1 | 8/2019 | Gruenbeck et al. |
| 2019/0264628 A1 | 8/2019 | Dudar |
| 2019/0265132 A1 | 8/2019 | Mou et al. |
| 2019/0266860 A1 | 8/2019 | Lakshmipathy et al. |
| 2019/0266871 A1 | 8/2019 | Verna et al. |
| 2019/0268458 A1 | 8/2019 | DeBates et al. |
| 2019/0271254 A1 | 9/2019 | Frobert et al. |
| 2019/0271685 A1 | 9/2019 | Haick et al. |
| 2019/0273817 A1 | 9/2019 | Ueno et al. |
| 2019/0275465 A1 | 9/2019 | Shirasawa et al. |
| 2019/0276602 A1 | 9/2019 | De Castro et al. |
| 2019/0277522 A1 | 9/2019 | Soyyigit |
| 2019/0277731 A1 | 9/2019 | Hur et al. |
| 2019/0285020 A1 | 9/2019 | Dudar et al. |
| 2019/0289803 A1 | 9/2019 | Gagne et al. |
| 2019/0292600 A1 | 9/2019 | Spira et al. |
| 2019/0292969 A1 | 9/2019 | Van Nieuwstadt et al. |
| 2019/0293008 A1 | 9/2019 | Wodausch et al. |
| 2019/0293288 A1 | 9/2019 | DeYoung et al. |
| 2019/0293628 A1 | 9/2019 | Hanson et al. |
| 2019/0301761 A1 | 10/2019 | Scheja et al. |
| 2019/0302072 A1 | 10/2019 | Mou et al. |
| 2019/0302073 A1 | 10/2019 | Mou et al. |
| 2019/0302075 A1 | 10/2019 | Mou et al. |
| 2019/0302076 A1 | 10/2019 | Mou et al. |
| 2019/0304280 A1 | 10/2019 | Bajaj et al. |
| 2019/0309671 A1 | 10/2019 | Rajagopal et al. |
| 2019/0310097 A1 | 10/2019 | Makita et al. |
| 2019/0311595 A1 | 10/2019 | Lacy |
| 2019/0311598 A1 | 10/2019 | Johnston |
| 2019/0313944 A1 | 10/2019 | Sun et al. |
| 2019/0315003 A1 | 10/2019 | Iwanami |
| 2019/0316538 A1 | 10/2019 | Martin et al. |
| 2019/0317073 A1 | 10/2019 | Horvath |
| 2019/0317079 A1 | 10/2019 | Trenholm et al. |
| 2019/0318598 A1 | 10/2019 | Aponte Luis |
| 2019/0319316 A1 | 10/2019 | Fifield |
| 2019/0323441 A1 | 10/2019 | Yuan et al. |
| 2019/0323985 A1 | 10/2019 | Xiao et al. |
| 2019/0324004 A1 | 10/2019 | Feinstein et al. |
| 2019/0328924 A1 | 10/2019 | Peterson et al. |
| 2019/0331038 A1 | 10/2019 | Brahma et al. |
| 2019/0331044 A1 | 10/2019 | Minaz et al. |
| 2019/0331062 A1 | 10/2019 | Dudar et al. |
| 2019/0331068 A1 | 10/2019 | Badawy et al. |
| 2019/0331359 A1 | 10/2019 | Sakaguchi et al. |
| 2019/0331558 A1 | 10/2019 | Mou et al. |
| 2019/0331582 A1 | 10/2019 | Mou et al. |
| 2019/0331619 A1 | 10/2019 | Choi et al. |
| 2019/0334740 A1 | 10/2019 | Mohiuddin et al. |
| 2019/0336374 A1 | 11/2019 | McClain |
| 2019/0338354 A1 | 11/2019 | Gonzales, Jr. |
| 2019/0339279 A1 | 11/2019 | Duhamel et al. |
| 2019/0340913 A1 | 11/2019 | Downs et al. |
| 2019/0342948 A1 | 11/2019 | Louveau et al. |
| 2019/0342973 A1 | 11/2019 | Schiffer et al. |
| 2019/0346401 A1 | 11/2019 | Kralicek et al. |
| 2019/0346417 A1 | 11/2019 | Benefield |
| 2019/0347924 A1 | 11/2019 | Trundle et al. |
| 2019/0353418 A1 | 11/2019 | Akinci et al. |
| 2019/0355234 A1 | 11/2019 | Kim |
| 2019/0357763 A1 | 11/2019 | Malkar et al. |

(56) References Cited

U.S. PATENT DOCUMENTS

| | | | |
|---|---|---|---|
| 2019/0359056 A1 | 11/2019 | Wilson et al. |
| 2019/0360413 A1 | 11/2019 | Uhrich et al. |
| 2019/0360434 A1 | 11/2019 | Dudar et al. |
| 2019/0360963 A1 | 11/2019 | Shuk et al. |
| 2019/0360985 A1 | 11/2019 | Hong |
| 2019/0365572 A1 | 12/2019 | Park et al. |
| 2019/0365941 A1 | 12/2019 | Elrod |
| 2019/0367963 A1 | 12/2019 | Yoshikawa et al. |
| 2019/0369073 A1 | 12/2019 | Gafsou |
| 2019/0369139 A1 | 12/2019 | Mohtashami et al. |
| 2019/0371137 A1 | 12/2019 | Fortin et al. |
| 2019/0375395 A1 | 12/2019 | Jentz et al. |
| 2019/0376433 A1 | 12/2019 | Wiebenga et al. |
| 2019/0376877 A1 | 12/2019 | Mou et al. |
| 2019/0376903 A1 | 12/2019 | Kurata et al. |
| 2019/0381996 A1 | 12/2019 | Kaneko et al. |
| 2019/0383557 A1 | 12/2019 | Jensen et al. |
| 2019/0383772 A1 | 12/2019 | Kuroki et al. |
| 2019/0383779 A1 | 12/2019 | Bruchet et al. |
| 2019/0387375 A1 | 12/2019 | Gao |
| 2019/0391082 A1 | 12/2019 | Yoon |
| 2019/0393699 A1 | 12/2019 | Shastri et al. |
| 2020/0000369 A1 | 1/2020 | Tiemann et al. |
| 2020/0002399 A1 | 1/2020 | Pfister et al. |
| 2020/0003142 A1 | 1/2020 | Pachner et al. |
| 2020/0003143 A1 | 1/2020 | Dudar |
| 2020/0003144 A1 | 1/2020 | Faied |
| 2020/0003774 A1 | 1/2020 | Hanson et al. |
| 2020/0005059 A1 | 1/2020 | Yamada et al. |
| 2020/0005617 A1 | 1/2020 | Janscha et al. |
| 2020/0008395 A1 | 1/2020 | Mischley |
| 2020/0011560 A1 | 1/2020 | Minamida et al. |
| 2020/0012883 A1 | 1/2020 | Kuo et al. |
| 2020/0013273 A1 | 1/2020 | Souloglou |
| 2020/0016564 A1 | 1/2020 | Surwade et al. |
| 2020/0018714 A1 | 1/2020 | Carr |
| 2020/0019168 A1 | 1/2020 | Guzman et al. |
| 2020/0020220 A1 | 1/2020 | Stefanski et al. |
| 2020/0024406 A1 | 1/2020 | Zhao et al. |
| 2020/0025717 A1 | 1/2020 | Manginell et al. |
| 2020/0025734 A1 | 1/2020 | Amin et al. |
| 2020/0025735 A1 | 1/2020 | Bardoni et al. |
| 2020/0025737 A1 | 1/2020 | Al Madani et al. |
| 2020/0027322 A1 | 1/2020 | Mundra et al. |
| 2020/0029858 A1 | 1/2020 | Reddy |
| 2020/0033020 A1 | 1/2020 | Fujii et al. |
| 2020/0033279 A1 | 1/2020 | Hur et al. |
| 2020/0033900 A1 | 1/2020 | Allen et al. |
| 2020/0036310 A1 | 1/2020 | Sarder et al. |
| 2020/0049043 A1 | 2/2020 | Nose et al. |
| 2020/0049048 A1 | 2/2020 | Franz et al. |
| 2020/0049091 A1 | 2/2020 | Dai et al. |
| 2020/0164771 A1* | 5/2020 | Unnervik ............ B60N 2/42745 |

FOREIGN PATENT DOCUMENTS

| | | |
|---|---|---|
| CA | 2272116 A1 | 11/2000 |
| CA | 2307443 A1 | 11/2000 |
| CA | 2379540 A1 | 12/2000 |
| CA | 2326848 A1 | 3/2001 |
| CA | 2384742 A1 | 3/2001 |
| CA | 2287028 A1 | 4/2001 |
| CA | 2389708 A1 | 5/2001 |
| CA | 2389730 A1 | 5/2001 |
| CA | 2298355 A1 | 8/2001 |
| CA | 2298359 A1 | 8/2001 |
| CA | 2402379 A1 | 8/2001 |
| CA | 2402371 A1 | 9/2001 |
| CA | 2402870 A1 | 9/2001 |
| CA | 2314237 A1 | 1/2002 |
| CA | 2416084 A1 | 2/2002 |
| CA | 2421772 A1 | 3/2002 |
| CA | 2373374 A1 | 8/2002 |
| CA | 2442581 A1 | 10/2002 |
| CA | 2429854 A1 | 11/2002 |
| CA | 2353759 A1 | 1/2003 |
| CA | 2381871 A1 | 2/2003 |
| CA | 2369720 A1 | 7/2003 |
| CA | 2310279 C | 8/2003 |
| CA | 2484770 A1 | 11/2003 |
| CA | 2488451 A1 | 12/2003 |
| CA | 2489309 A1 | 12/2003 |
| CA | 2437420 A1 | 2/2004 |
| CA | 2498864 A1 | 4/2004 |
| CA | 2504452 A1 | 5/2004 |
| CA | 2452464 A1 | 6/2004 |
| CA | 2507044 A1 | 6/2004 |
| CA | 2316535 C | 7/2004 |
| CA | 2507300 A1 | 7/2004 |
| CA | 2360616 C | 8/2004 |
| CA | 2511379 A1 | 8/2004 |
| CA | 2515144 A1 | 8/2004 |
| CA | 2423512 A1 | 9/2004 |
| CA | 2523602 A1 | 11/2004 |
| CA | 2496025 A1 | 1/2005 |
| CA | 2535419 A1 | 2/2005 |
| CA | 2499198 A1 | 9/2005 |
| CA | 2418612 C | 12/2005 |
| CA | 2502031 A1 | 12/2005 |
| CA | 2540709 A1 | 12/2005 |
| CA | 2566606 A1 | 12/2005 |
| CA | 2403417 C | 1/2006 |
| CA | 2360595 C | 2/2006 |
| CA | 2395563 C | 3/2006 |
| CA | 2529880 A1 | 4/2006 |
| CA | 2338006 C | 5/2006 |
| CA | 2353033 C | 5/2006 |
| CA | 2593716 A1 | 8/2006 |
| CA | 2597762 A1 | 8/2006 |
| CA | 2500116 A1 | 9/2006 |
| CA | 2600438 A1 | 9/2006 |
| CA | 2601405 A1 | 9/2006 |
| CA | 2274572 C | 10/2006 |
| CA | 2603956 A1 | 10/2006 |
| CA | 2400109 C | 11/2006 |
| CA | 2606664 A1 | 11/2006 |
| CA | 2609759 A1 | 12/2006 |
| CA | 2433314 C | 3/2007 |
| CA | 2453224 C | 3/2007 |
| CA | 2623003 A1 | 3/2007 |
| CA | 2630577 A1 | 6/2007 |
| CA | 3008800 A1 | 6/2007 |
| CA | 2573284 A1 | 7/2007 |
| CA | 2635682 A1 | 7/2007 |
| CA | 2397790 A1 | 8/2007 |
| CA | 2449549 C | 8/2007 |
| CA | 2526148 C | 8/2007 |
| CA | 2633826 A1 | 8/2007 |
| CA | 2583447 A1 | 9/2007 |
| CA | 2582967 A1 | 10/2007 |
| CA | 2587814 A1 | 11/2007 |
| CA | 2651482 A1 | 11/2007 |
| CA | 2450172 C | 1/2008 |
| CA | 2660623 A1 | 2/2008 |
| CA | 2341065 C | 5/2008 |
| CA | 2452124 C | 5/2008 |
| CA | 2679597 A1 | 6/2008 |
| CA | 2616362 A1 | 7/2008 |
| CA | 2446710 C | 8/2008 |
| CA | 2515250 C | 9/2008 |
| CA | 2692948 A1 | 9/2008 |
| CA | 2446315 C | 10/2008 |
| CA | 2478112 C | 11/2008 |
| CA | 2725319 A1 | 11/2008 |
| CA | 2687494 A1 | 12/2008 |
| CA | 2448849 C | 1/2009 |
| CA | 2452465 C | 1/2009 |
| CA | 2440357 C | 2/2009 |
| CA | 2694918 A1 | 2/2009 |
| CA | 2696044 A1 | 2/2009 |
| CA | 2604184 A1 | 4/2009 |
| CA | 2374987 C | 6/2009 |
| CA | 2715403 A1 | 8/2009 |
| CA | 2370835 C | 9/2009 |

(56) References Cited

FOREIGN PATENT DOCUMENTS

| | | | |
|---|---|---|---|
| CA | 2417149 | C | 9/2009 |
| CA | 2525523 | C | 9/2009 |
| CA | 2511519 | C | 10/2009 |
| CA | 2572422 | C | 10/2009 |
| CA | 2720633 | A1 | 10/2009 |
| CA | 2444072 | C | 12/2009 |
| CA | 2480915 | C | 12/2009 |
| CA | 2727617 | A1 | 12/2009 |
| CA | 2769663 | A1 | 2/2010 |
| CA | 2703218 | A1 | 4/2010 |
| CA | 2419110 | C | 6/2010 |
| CA | 2419124 | C | 6/2010 |
| CA | 2483684 | C | 7/2010 |
| CA | 2750019 | A1 | 7/2010 |
| CA | 2750292 | A1 | 7/2010 |
| CA | 2751223 | A1 | 8/2010 |
| CA | 2749597 | A1 | 9/2010 |
| CA | 2767496 | A1 | 9/2010 |
| CA | 2669861 | A1 | 10/2010 |
| CA | 2757541 | A1 | 10/2010 |
| CA | 2668302 | A1 | 12/2010 |
| CA | 2388591 | C | 1/2011 |
| CA | 2401046 | C | 1/2011 |
| CA | 2769266 | A1 | 2/2011 |
| CA | 2772744 | A1 | 3/2011 |
| CA | 2477722 | C | 4/2011 |
| CA | 2529669 | C | 4/2011 |
| CA | 2777622 | A1 | 4/2011 |
| CA | 2777623 | A1 | 4/2011 |
| CA | 2777624 | A1 | 4/2011 |
| CA | 2777625 | A1 | 4/2011 |
| CA | 2466324 | C | 5/2011 |
| CA | 2604264 | C | 6/2011 |
| CA | 2787303 | A1 | 7/2011 |
| CA | 2413279 | C | 8/2011 |
| CA | 2385599 | C | 9/2011 |
| CA | 2791937 | A1 | 9/2011 |
| CA | 2794130 | A1 | 10/2011 |
| CA | 2794388 | A1 | 10/2011 |
| CA | 2473735 | C | 11/2011 |
| CA | 2491490 | C | 12/2011 |
| CA | 2703594 | C | 1/2012 |
| CA | 2375021 | C | 2/2012 |
| CA | 2810678 | A1 | 3/2012 |
| CA | 2811394 | A1 | 3/2012 |
| CA | 2471897 | C | 4/2012 |
| CA | 2813721 | A1 | 4/2012 |
| CA | 2758665 | A1 | 5/2012 |
| CA | 2761030 | A1 | 6/2012 |
| CA | 2698926 | C | 8/2012 |
| CA | 2746893 | C | 8/2012 |
| CA | 2563790 | C | 10/2012 |
| CA | 2486221 | C | 12/2012 |
| CA | 2583455 | C | 12/2012 |
| CA | 2731162 | C | 12/2012 |
| CA | 2838505 | A1 | 12/2012 |
| CA | 2548252 | C | 1/2013 |
| CA | 2840209 | A1 | 1/2013 |
| CA | 2648068 | C | 2/2013 |
| CA | 2709084 | C | 2/2013 |
| CA | 2564393 | C | 3/2013 |
| CA | 2588074 | C | 3/2013 |
| CA | 2753400 | A1 | 3/2013 |
| CA | 2789481 | A1 | 3/2013 |
| CA | 2847348 | A1 | 3/2013 |
| CA | 2847886 | A1 | 3/2013 |
| CA | 2665677 | C | 4/2013 |
| CA | 2666662 | C | 4/2013 |
| CA | 2571080 | C | 5/2013 |
| CA | 2616631 | C | 5/2013 |
| CA | 2854677 | A1 | 5/2013 |
| CA | 2858550 | A1 | 6/2013 |
| CA | 2536375 | C | 7/2013 |
| CA | 2541756 | C | 7/2013 |
| CA | 2734770 | C | 7/2013 |
| CA | 2802306 | A1 | 7/2013 |
| CA | 2679927 | C | 8/2013 |
| CA | 2863835 | A1 | 8/2013 |
| CA | 2867491 | A1 | 9/2013 |
| CA | 2470115 | C | 10/2013 |
| CA | 2887367 | A1 | 11/2013 |
| CA | 2584498 | C | 12/2013 |
| CA | 2820237 | A1 | 1/2014 |
| CA | 2879131 | A1 | 1/2014 |
| CA | 2789248 | A1 | 3/2014 |
| CA | 2816340 | C | 3/2014 |
| CA | 2827173 | A1 | 3/2014 |
| CA | 2359625 | C | 4/2014 |
| CA | 2390261 | C | 4/2014 |
| CA | 2730527 | C | 4/2014 |
| CA | 2575998 | C | 5/2014 |
| CA | 2833846 | A1 | 5/2014 |
| CA | 2889843 | A1 | 5/2014 |
| CA | 2801978 | A1 | 7/2014 |
| CA | 2803125 | A1 | 7/2014 |
| CA | 2814256 | C | 7/2014 |
| CA | 2899195 | A1 | 9/2014 |
| CA | 2904262 | A1 | 9/2014 |
| CA | 2905091 | A1 | 9/2014 |
| CA | 2906458 | A1 | 9/2014 |
| CA | 2906963 | A1 | 9/2014 |
| CA | 2699171 | C | 10/2014 |
| CA | 2909892 | A1 | 10/2014 |
| CA | 2918594 | A1 | 11/2014 |
| CA | 2914259 | A1 | 12/2014 |
| CA | 2916204 | A1 | 12/2014 |
| CA | 2679102 | C | 1/2015 |
| CA | 2918680 | A1 | 1/2015 |
| CA | 3033768 | A1 | 1/2015 |
| CA | 2803152 | C | 2/2015 |
| CA | 2861749 | A1 | 3/2015 |
| CA | 2866032 | A1 | 4/2015 |
| CA | 2925542 | A1 | 4/2015 |
| CA | 2926442 | A1 | 4/2015 |
| CA | 2926453 | A1 | 4/2015 |
| CA | 2926811 | A1 | 4/2015 |
| CA | 2964002 | A1 | 4/2015 |
| CA | 2633326 | C | 5/2015 |
| CA | 2870508 | C | 5/2015 |
| CA | 2932408 | A1 | 6/2015 |
| CA | 2938039 | A1 | 7/2015 |
| CA | 2889380 | A1 | 10/2015 |
| CA | 2946448 | A1 | 10/2015 |
| CA | 2951690 | A1 | 12/2015 |
| CA | 2456621 | C | 1/2016 |
| CA | 2896120 | A1 | 1/2016 |
| CA | 2608943 | C | 2/2016 |
| CA | 2674528 | C | 2/2016 |
| CA | 2958077 | A1 | 2/2016 |
| CA | 2770150 | C | 3/2016 |
| CA | 2814372 | C | 3/2016 |
| CA | 2734783 | C | 4/2016 |
| CA | 2963635 | A1 | 4/2016 |
| CA | 2963780 | A1 | 4/2016 |
| CA | 2964416 | A1 | 4/2016 |
| CA | 2794670 | C | 5/2016 |
| CA | 2965455 | A1 | 5/2016 |
| CA | 2966524 | A1 | 5/2016 |
| CA | 2641889 | C | 6/2016 |
| CA | 2789869 | C | 6/2016 |
| CA | 2707457 | C | 7/2016 |
| CA | 2670457 | C | 8/2016 |
| CA | 2887929 | A1 | 9/2016 |
| CA | 2923265 | A1 | 9/2016 |
| CA | 2978703 | A1 | 9/2016 |
| CA | 2918662 | C | 11/2016 |
| CA | 2928212 | A1 | 11/2016 |
| CA | 2983380 | A1 | 11/2016 |
| CA | 2558851 | C | 12/2016 |
| CA | 2663126 | C | 12/2016 |
| CA | 2986845 | A1 | 12/2016 |
| CA | 2989000 | A1 | 12/2016 |
| CA | 2935406 | A1 | 1/2017 |
| CA | 2935820 | A1 | 1/2017 |

(56) References Cited

FOREIGN PATENT DOCUMENTS

| | | | |
|---|---|---|---|
| CA | 2991087 A1 | 1/2017 |
| CA | 2945501 A1 | 4/2017 |
| CA | 3000566 A1 | 4/2017 |
| CA | 2645534 C | 5/2017 |
| CA | 2950795 A1 | 6/2017 |
| CA | 2884660 C | 7/2017 |
| CA | 2952364 A1 | 7/2017 |
| CA | 3009143 A1 | 7/2017 |
| CA | 2921709 A1 | 8/2017 |
| CA | 3019528 A1 | 10/2017 |
| CA | 2625286 C | 11/2017 |
| CA | 2804068 C | 11/2017 |
| CA | 2809419 C | 11/2017 |
| CA | 2966817 A1 | 11/2017 |
| CA | 3026146 A1 | 12/2017 |
| CA | 3026379 A1 | 12/2017 |
| CA | 2976874 A1 | 2/2018 |
| CA | 2859140 C | 4/2018 |
| CA | 3032714 A1 | 4/2018 |
| CA | 2764045 C | 5/2018 |
| CA | 2817135 C | 5/2018 |
| CA | 2947079 A1 | 5/2018 |
| CA | 3046342 A1 | 6/2018 |
| CA | 2853284 C | 8/2018 |
| CA | 2994589 A1 | 8/2018 |
| CA | 2963648 A1 | 10/2018 |
| CA | 3060412 A1 | 10/2018 |
| CA | 3002086 A1 | 11/2018 |
| CA | 3061928 A1 | 11/2018 |
| CA | 3009858 A1 | 12/2018 |
| CA | 3063741 A1 | 12/2018 |
| CA | 3064886 A1 | 12/2018 |
| CA | 2827187 C | 1/2019 |
| CA | 2844108 C | 1/2019 |
| CA | 2895089 C | 2/2019 |
| CA | 2949211 C | 2/2019 |
| CA | 2953117 C | 2/2019 |
| CA | 3013693 A1 | 2/2019 |
| CA | 3056670 A1 | 2/2019 |
| CA | 2890523 C | 4/2019 |
| CA | 2918683 C | 4/2019 |
| CA | 3020553 A1 | 4/2019 |
| CA | 3024061 A1 | 5/2019 |
| CA | 3030730 A1 | 7/2019 |
| CA | 2993966 A1 | 8/2019 |
| CA | 2788495 C | 9/2019 |
| CA | 2872239 C | 9/2019 |
| CA | 3004073 A1 | 11/2019 |
| CA | 2943993 C | 2/2020 |
| CA | 2907132 C | 6/2020 |
| CA | 2863441 C | 7/2020 |
| CA | 2877128 C | 7/2020 |
| CA | 2841288 C | 10/2020 |
| CA | 2956623 C | 10/2020 |
| CA | 2929504 C | 11/2020 |
| MX | PA01013256 A | 7/2002 |
| MX | PA02004467 A | 9/2002 |
| MX | PA02004618 A | 9/2002 |
| MX | PA03005234 A | 10/2003 |
| MX | PA02001134 A | 4/2004 |
| MX | PA03009556 A | 12/2004 |
| MX | PA04011283 A | 2/2005 |
| MX | PA03009997 A | 4/2005 |
| MX | PA03007340 A | 10/2005 |
| MX | PA04007528 A | 1/2006 |
| MX | PA06003733 A | 6/2006 |
| MX | 2011001916 A | 8/2011 |
| MX | 2012002602 A | 7/2012 |
| MX | 2011013405 A | 10/2012 |
| MX | 2014009852 A | 10/2014 |
| MX | 2014012086 A | 11/2014 |
| MX | 2015004232 A | 6/2015 |
| MX | 2015001896 A | 8/2015 |
| MX | 2015003835 A | 2/2016 |
| MX | 338943 B | 5/2016 |
| MX | 2015017943 A | 5/2016 |
| MX | 340191 B | 6/2016 |
| MX | 2016006252 A | 2/2017 |
| MX | 2017001652 A | 4/2017 |
| MX | 347634 B | 5/2017 |
| MX | 350020 B | 8/2017 |
| MX | 350527 B | 9/2017 |
| MX | 2017015691 A | 4/2018 |
| MX | 2017006324 A | 8/2018 |
| MX | 2018001801 A | 11/2018 |
| MX | 361392 B | 12/2018 |
| MX | 2018014848 A | 4/2019 |
| MX | 365571 B | 5/2019 |
| MX | 2017015162 A | 5/2019 |
| MX | 2019002299 A | 7/2019 |
| WO | WO-2017138873 A1 | 8/2017 |
| WO | WO-2017165220 A1 | 9/2017 |
| WO | WO-2017186519 A1 | 11/2017 |
| WO | WO-2017189747 A1 | 11/2017 |
| WO | WO-2017203131 A1 | 11/2017 |
| WO | WO-2017211521 A1 | 12/2017 |
| WO | WO-2017216440 A1 | 12/2017 |
| WO | WO-2017216496 A1 | 12/2017 |
| WO | WO-2018013039 A1 | 1/2018 |
| WO | WO-2018013764 A1 | 1/2018 |
| WO | WO-2018029230 A1 | 2/2018 |
| WO | WO-2018035540 A1 | 2/2018 |
| WO | WO-2018041502 A1 | 3/2018 |
| WO | WO-2018041637 A1 | 3/2018 |
| WO | WO-2018046037 A1 | 3/2018 |
| WO | WO-2018046845 A1 | 3/2018 |
| WO | WO-2018054912 A1 | 3/2018 |
| WO | WO-2018065141 A1 | 4/2018 |
| WO | WO-2018084039 A1 | 5/2018 |
| WO | WO-2018096894 A1 | 5/2018 |
| WO | WO-2018097246 A1 | 5/2018 |
| WO | WO-2018102583 A1 | 6/2018 |
| WO | WO-2018104425 A1 | 6/2018 |
| WO | WO-2018111761 A1 | 6/2018 |
| WO | WO-2018115620 A1 | 6/2018 |
| WO | WO-2018122556 A1 | 7/2018 |
| WO | WO-2018128272 A1 | 7/2018 |
| WO | WO-2018132007 A1 | 7/2018 |
| WO | WO-2018132560 A1 | 7/2018 |
| WO | WO-2018132746 A1 | 7/2018 |
| WO | WO-2018133302 A1 | 7/2018 |
| WO | WO-2018135550 A1 | 7/2018 |
| WO | WO-2018136263 A1 | 7/2018 |
| WO | WO-2018139899 A1 | 8/2018 |
| WO | WO-2018140330 A1 | 8/2018 |
| WO | WO-2018141620 A1 | 8/2018 |
| WO | WO-2018142162 A1 | 8/2018 |
| WO | WO-2018142961 A1 | 8/2018 |
| WO | WO-2018143256 A1 | 8/2018 |
| WO | WO-2018145706 A1 | 8/2018 |
| WO | WO-2018148740 A1 | 8/2018 |
| WO | WO-2018154567 A1 | 8/2018 |
| WO | WO-2018154614 A2 | 8/2018 |
| WO | WO-2018155260 A1 | 8/2018 |
| WO | WO-2018156001 A1 | 8/2018 |
| WO | WO-2018156002 A1 | 8/2018 |
| WO | WO-2018156003 A1 | 8/2018 |
| WO | WO-2018158083 A1 | 9/2018 |
| WO | WO-2018159164 A1 | 9/2018 |
| WO | WO-2018159165 A1 | 9/2018 |
| WO | WO-2018159518 A1 | 9/2018 |
| WO | WO-2018160668 A1 | 9/2018 |
| WO | WO-2018160835 A1 | 9/2018 |
| WO | WO-2018162638 A1 | 9/2018 |
| WO | WO-2018168672 A1 | 9/2018 |
| WO | WO-2018170154 A1 | 9/2018 |
| WO | WO-2018170187 A1 | 9/2018 |
| WO | WO-2018173060 A1 | 9/2018 |
| WO | WO-2018174823 A1 | 9/2018 |
| WO | WO-2018177699 A1 | 10/2018 |
| WO | WO-2018182037 A1 | 10/2018 |
| WO | WO-2018182323 A1 | 10/2018 |
| WO | WO-2018182324 A1 | 10/2018 |
| WO | WO-2018183215 A1 | 10/2018 |

(56) References Cited

FOREIGN PATENT DOCUMENTS

| | | |
|---|---|---|
| WO | WO-2018183506 A1 | 10/2018 |
| WO | WO-2018183675 A1 | 10/2018 |
| WO | WO-2018184162 A1 | 10/2018 |
| WO | WO-2018187266 A1 | 10/2018 |
| WO | WO-2018188941 A1 | 10/2018 |
| WO | WO-2018189926 A1 | 10/2018 |
| WO | WO-2018190003 A1 | 10/2018 |
| WO | WO-2018191044 A1 | 10/2018 |
| WO | WO-2018191688 A2 | 10/2018 |
| WO | WO-2018191699 A1 | 10/2018 |
| WO | WO-2018191716 A1 | 10/2018 |
| WO | WO-2018194650 A1 | 10/2018 |
| WO | WO-2018194943 A1 | 10/2018 |
| WO | WO-2018198869 A1 | 11/2018 |
| WO | WO-2018201135 A1 | 11/2018 |
| WO | WO-2018202004 A1 | 11/2018 |
| WO | WO-2018202416 A1 | 11/2018 |
| WO | WO-2018202975 A2 | 11/2018 |
| WO | WO-2018202977 A2 | 11/2018 |
| WO | WO-2018206385 A1 | 11/2018 |
| WO | WO-2018207879 A1 | 11/2018 |
| WO | WO-2018207997 A1 | 11/2018 |
| WO | WO-2018209943 A1 | 11/2018 |
| WO | WO-2018211126 A1 | 11/2018 |
| WO | WO-2018211642 A1 | 11/2018 |
| WO | WO-2018212423 A1 | 11/2018 |
| WO | WO-2018213435 A1 | 11/2018 |
| WO | WO-2018214861 A1 | 11/2018 |
| WO | WO-2018215220 A1 | 11/2018 |
| WO | WO-2018215430 A1 | 11/2018 |
| WO | WO-2018215505 A1 | 11/2018 |
| WO | WO-2018216192 A1 | 11/2018 |
| WO | WO-2018216848 A1 | 11/2018 |
| WO | WO-2018218090 A1 | 11/2018 |
| WO | WO-2018218868 A1 | 12/2018 |
| WO | WO-2018218869 A1 | 12/2018 |
| WO | WO-2018218870 A1 | 12/2018 |
| WO | WO-2018220830 A1 | 12/2018 |
| WO | WO-2018221889 A1 | 12/2018 |
| WO | WO-2018222789 A1 | 12/2018 |
| WO | WO-2018222905 A1 | 12/2018 |
| WO | WO-2018222980 A1 | 12/2018 |
| WO | WO-2018224373 A1 | 12/2018 |
| WO | WO-2018225058 A1 | 12/2018 |
| WO | WO-2018230766 A1 | 12/2018 |
| WO | WO-2018231850 A1 | 12/2018 |
| WO | WO-2018235073 A1 | 12/2018 |
| WO | WO-2018235148 A1 | 12/2018 |
| WO | WO-2018236026 A1 | 12/2018 |
| WO | WO-2019003181 A1 | 1/2019 |
| WO | WO-2019006584 A1 | 1/2019 |
| WO | WO-2019008089 A1 | 1/2019 |
| WO | WO-2019021275 A1 | 1/2019 |
| WO | WO-2019023294 A1 | 1/2019 |
| WO | WO-2019025662 A1 | 2/2019 |
| WO | WO-2019025769 A1 | 2/2019 |
| WO | WO-2019027328 A1 | 2/2019 |
| WO | WO-2019027701 A1 | 2/2019 |
| WO | WO-2019028106 A1 | 2/2019 |
| WO | WO-2019028429 A1 | 2/2019 |
| WO | WO-2019032336 A1 | 2/2019 |
| WO | WO-2019034606 A1 | 2/2019 |
| WO | WO-2019034949 A1 | 2/2019 |
| WO | WO-2019035476 A1 | 2/2019 |
| WO | WO-2019035950 A1 | 2/2019 |
| WO | WO-2019036889 A1 | 2/2019 |
| WO | WO-2019036958 A1 | 2/2019 |
| WO | WO-2019037665 A1 | 2/2019 |
| WO | WO-2019037983 A1 | 2/2019 |
| WO | WO-2019040002 A1 | 2/2019 |
| WO | WO-2019040937 A1 | 2/2019 |
| WO | WO-2019041488 A1 | 3/2019 |
| WO | WO-2019046182 A1 | 3/2019 |
| WO | WO-2019046970 A1 | 3/2019 |
| WO | WO-2019051826 A1 | 3/2019 |
| WO | WO-2019051893 A1 | 3/2019 |
| WO | WO-2019052037 A1 | 3/2019 |
| WO | WO-2019053259 A1 | 3/2019 |
| WO | WO-2019053700 A2 | 3/2019 |
| WO | WO-2019054649 A1 | 3/2019 |
| WO | WO-2019054650 A1 | 3/2019 |
| WO | WO-2019055876 A2 | 3/2019 |
| WO | WO-2019056159 A1 | 3/2019 |
| WO | WO-2019056323 A1 | 3/2019 |
| WO | WO-2019059276 A1 | 3/2019 |
| WO | WO-2019060950 A1 | 4/2019 |
| WO | WO-2019061825 A1 | 4/2019 |
| WO | WO-2019067454 A1 | 4/2019 |
| WO | WO-2019068851 A1 | 4/2019 |
| WO | WO-2019069893 A1 | 4/2019 |
| WO | WO-2019072352 A2 | 4/2019 |
| WO | WO-2019072730 A1 | 4/2019 |
| WO | WO-2019073280 A1 | 4/2019 |
| WO | WO-2019074526 A1 | 4/2019 |
| WO | WO-2019075110 A1 | 4/2019 |
| WO | WO-2019075365 A1 | 4/2019 |
| WO | WO-2019076418 A1 | 4/2019 |
| WO | WO-2019077478 A1 | 4/2019 |
| WO | WO-2019077558 A1 | 4/2019 |
| WO | WO-2019079039 A1 | 4/2019 |
| WO | WO-2019080784 A1 | 5/2019 |
| WO | WO-2019082836 A1 | 5/2019 |
| WO | WO-2019085369 A1 | 5/2019 |
| WO | WO-2019086082 A1 | 5/2019 |
| WO | WO-2019088839 A1 | 5/2019 |
| WO | WO-2019090549 A1 | 5/2019 |
| WO | WO-2019093162 A1 | 5/2019 |
| WO | WO-2019095790 A1 | 5/2019 |
| WO | WO-2019096568 A1 | 5/2019 |
| WO | WO-2019097534 A1 | 5/2019 |
| WO | WO-2019097634 A1 | 5/2019 |
| WO | WO-2019098432 A1 | 5/2019 |
| WO | WO-2019098977 A2 | 5/2019 |
| WO | WO-2019099387 A1 | 5/2019 |
| WO | WO-2019099425 A1 | 5/2019 |
| WO | WO-2019099431 A1 | 5/2019 |
| WO | WO-2019101812 A2 | 5/2019 |
| WO | WO-2019102654 A1 | 5/2019 |
| WO | WO-2019102660 A1 | 5/2019 |
| WO | WO-2019104130 A1 | 5/2019 |
| WO | WO-2019105859 A1 | 6/2019 |
| WO | WO-2019106379 A2 | 6/2019 |
| WO | WO-2019107370 A1 | 6/2019 |
| WO | WO-2019107965 A1 | 6/2019 |
| WO | WO-2019110155 A1 | 6/2019 |
| WO | WO-2019111262 A1 | 6/2019 |
| WO | WO-2019111471 A1 | 6/2019 |
| WO | WO-2019111850 A1 | 6/2019 |
| WO | WO-2019114052 A1 | 6/2019 |
| WO | WO-2019116543 A1 | 6/2019 |
| WO | WO-2019117321 A1 | 6/2019 |
| WO | WO-2019122889 A1 | 6/2019 |
| WO | WO-2019123864 A1 | 6/2019 |
| WO | WO-2019123865 A1 | 6/2019 |
| WO | WO-2019124625 A1 | 6/2019 |
| WO | WO-2019124993 A1 | 6/2019 |
| WO | WO-2019126181 A1 | 6/2019 |
| WO | WO-2019126811 A1 | 6/2019 |
| WO | WO-2019128203 A1 | 7/2019 |
| WO | WO-2019129028 A1 | 7/2019 |
| WO | WO-2019130255 A1 | 7/2019 |
| WO | WO-2019131789 A1 | 7/2019 |
| WO | WO-2019132269 A1 | 7/2019 |
| WO | WO-2019134955 A1 | 7/2019 |
| WO | WO-2019136110 A1 | 7/2019 |
| WO | WO-2019137604 A1 | 7/2019 |
| WO | WO-2019140543 A1 | 7/2019 |
| WO | WO-2019146971 A1 | 8/2019 |
| WO | WO-2019147537 A1 | 8/2019 |
| WO | WO-2019149230 A1 | 8/2019 |
| WO | WO-2019149231 A1 | 8/2019 |
| WO | WO-2019149232 A1 | 8/2019 |
| WO | WO-2019149233 A1 | 8/2019 |
| WO | WO-2019149234 A1 | 8/2019 |

(56) References Cited

FOREIGN PATENT DOCUMENTS

| | | |
|---|---|---|
| WO | WO-2019149235 A1 | 8/2019 |
| WO | WO-2019150182 A1 | 8/2019 |
| WO | WO-2019150735 A1 | 8/2019 |
| WO | WO-2019152047 A1 | 8/2019 |
| WO | WO-2019152832 A1 | 8/2019 |
| WO | WO-2019156229 A1 | 8/2019 |
| WO | WO-2019157302 A1 | 8/2019 |
| WO | WO-2019157784 A1 | 8/2019 |
| WO | WO-2019158433 A1 | 8/2019 |
| WO | WO-2019162949 A1 | 8/2019 |
| WO | WO-2019162960 A1 | 8/2019 |
| WO | WO-2019163966 A1 | 8/2019 |
| WO | WO-2019165422 A1 | 8/2019 |
| WO | WO-2019168427 A1 | 9/2019 |
| WO | WO-2019169803 A1 | 9/2019 |
| WO | WO-2019172251 A1 | 9/2019 |
| WO | WO-2019172859 A1 | 9/2019 |
| WO | WO-2019179699 A1 | 9/2019 |
| WO | WO-2019180985 A1 | 9/2019 |
| WO | WO-2019182114 A1 | 9/2019 |
| WO | WO-2019185107 A1 | 10/2019 |
| WO | WO-2019185764 A1 | 10/2019 |
| WO | WO-2019186527 A1 | 10/2019 |
| WO | WO-2019187671 A1 | 10/2019 |
| WO | WO-2019188408 A1 | 10/2019 |
| WO | WO-2019189128 A1 | 10/2019 |
| WO | WO-2019189964 A1 | 10/2019 |
| WO | WO-2019195764 A1 | 10/2019 |
| WO | WO-2019198648 A1 | 10/2019 |
| WO | WO-2019200021 A1 | 10/2019 |
| WO | WO-2019204779 A1 | 10/2019 |
| WO | WO-2019204785 A1 | 10/2019 |
| WO | WO-2019204788 A1 | 10/2019 |
| WO | WO-2019204789 A1 | 10/2019 |
| WO | WO-2019204790 A1 | 10/2019 |
| WO | WO-2019206541 A1 | 10/2019 |
| WO | WO-2019206610 A1 | 10/2019 |
| WO | WO-2019207888 A1 | 10/2019 |
| WO | WO-2019210718 A1 | 11/2019 |
| WO | WO-2019210719 A1 | 11/2019 |
| WO | WO-2019210720 A1 | 11/2019 |
| WO | WO-2019213280 A1 | 11/2019 |
| WO | WO-2019213439 A1 | 11/2019 |
| WO | WO-2019213998 A1 | 11/2019 |
| WO | WO-2019214433 A1 | 11/2019 |
| WO | WO-2019214821 A1 | 11/2019 |
| WO | WO-2019216755 A1 | 11/2019 |
| WO | WO-2019217191 A1 | 11/2019 |
| WO | WO-2019217267 A1 | 11/2019 |
| WO | WO-2019218395 A1 | 11/2019 |
| WO | WO-2019222202 A1 | 11/2019 |
| WO | WO-2019222964 A1 | 11/2019 |
| WO | WO-2019224542 A1 | 11/2019 |
| WO | WO-2019224628 A1 | 11/2019 |
| WO | WO-2019224865 A1 | 11/2019 |
| WO | WO-2019225894 A1 | 11/2019 |
| WO | WO-2019226357 A1 | 11/2019 |
| WO | WO-2019227388 A1 | 12/2019 |
| WO | WO-2019228617 A1 | 12/2019 |
| WO | WO-2019231199 A1 | 12/2019 |
| WO | WO-2019232014 A1 | 12/2019 |
| WO | WO-2019234978 A1 | 12/2019 |
| WO | WO-2019236032 A2 | 12/2019 |
| WO | WO-2019236974 A1 | 12/2019 |
| WO | WO-2019239025 A1 | 12/2019 |
| WO | WO-2019239360 A1 | 12/2019 |
| WO | WO-2019239855 A1 | 12/2019 |
| WO | WO-2019240100 A1 | 12/2019 |
| WO | WO-2019241126 A1 | 12/2019 |
| WO | WO-2019243361 A1 | 12/2019 |
| WO | WO-2020002667 A1 | 1/2020 |
| WO | WO-2020003532 A1 | 1/2020 |
| WO | WO-2020004959 A1 | 1/2020 |
| WO | WO-2020005874 A1 | 1/2020 |
| WO | WO-2020010026 A1 | 1/2020 |
| WO | WO-2020010921 A1 | 1/2020 |
| WO | WO-2020012002 A1 | 1/2020 |
| WO | WO-2020012162 A1 | 1/2020 |
| WO | WO-2020012800 A1 | 1/2020 |

\* cited by examiner

VEHICLE FEATURE CONTROL SYSTEMS AND METHODS BASED ON SMOKING

CROSS-REFERENCE TO RELATED APPLICATIONS

This application claims the benefit of U.S. Provisional Application No. 63/067,932, filed on Aug. 20, 2020. The entire disclosure of the application referenced above is incorporated herein by reference.

FIELD

The present disclosure relates to vehicles and more particularly to systems and methods for controlling features of vehicles based on smoking.

BACKGROUND

This section provides background information related to the present disclosure which is not necessarily prior art.

Vehicles have been recalled due to carbon monoxide entering their passenger cabins and for other reasons. Humans may be overcome by carbon monoxide and lose consciousness.

There may be numerous other situations where chemicals could be present within a passenger cabin of a vehicle. For example, a user may bring an aerosol can in to the passenger cabin of a vehicle and forget to take it out. Due to heat or cold, the aerosol can could emit its contents into the passenger cabin. One or more users could enter the vehicle later and breathe the contents without knowledge.

Electric vehicles include one or more batteries that contain chemicals, such as lithium. The batteries may be located under the passenger cabin and, under some circumstances, can rupture and emit chemicals. Some chemicals that may be present within a passenger cabin of a vehicle may be odorless and colorless.

SUMMARY

In a feature, a vehicle system includes: at least one of: a sensor configured to measure an amount of a chemical in air within a passenger cabin of a vehicle; and a camera configured to capture images within the passenger cabin of the vehicle; and a control module configured to: detect smoking within the passenger cabin based on the at least one of the amount of the chemical and at least one of the images; and in response to smoking being detected within the passenger cabin, adjust operation of at least one of a luxury feature of the vehicle and a comfort feature of the vehicle.

In further features: the vehicle includes the sensor; the sensor is configured to measure an amount of volatile organic compounds (VOCs) in the air within the passenger cabin; and the control module is configured to detect smoking within the passenger cabin when the amount of the VOCs is greater than a predetermined value.

In further features: the vehicle includes the sensor; the sensor is a smoke sensor configured to measure an amount of smoke in the air within the passenger cabin; and the control module is configured to detect smoking within the passenger cabin when the amount of the smoke is greater than a predetermined value.

In further features, the smoke sensor is a photoelectric smoke sensor.

In further features, the smoke sensor is an ionization smoke sensor.

In further features, the control module is configured to, in response to smoking being detected within the passenger cabin, disable heating and cooling of the passenger cabin by a heating ventilation and air conditioning (HVAC) system of the vehicle.

In further features, the control module is configured to, in response to smoking being detected within the passenger cabin while cooling of the passenger cabin is being provided by a heating ventilation and air conditioning (HVAC) system of the vehicle, adjust operation of the HVAC system and warm the passenger cabin.

In further features, the control module is configured to, in response to smoking being detected within the passenger cabin, disable a seat heater configured to heat a seat within the passenger cabin.

In further features, the control module is configured to, in response to smoking being detected within the passenger cabin while a seat heater configured to heat a seat within the passenger cabin is on, disable the seat heater and turn on a seat cooler configured to cool the seat.

In further features, the control module is configured to, in response to smoking being detected within the passenger cabin while a seat heater configured to heat a seat within the passenger cabin is on, adjust operation of the seat heater and increase heating of the seat.

In further features, the control module is configured to, in response to smoking being detected within the passenger cabin, disable a seat cooler configured to cool a seat within the passenger cabin.

In further features, the control module is configured to, in response to smoking being detected within the passenger cabin while a seat cooler configured to cool a seat within the passenger cabin is on, disable the seat cooler and turn on a seat heater configured to heat the seat.

In further features, the control module is configured to, in response to smoking being detected within the passenger cabin while a seat cooler configured to cool a seat within the passenger cabin is on, adjust operation of the seat cooler and increase cooling of the seat.

In further features, the control module is configured to, in response to smoking being detected within the passenger cabin, disable a seat massager of a seat within the passenger cabin.

In further features, the control module is configured to, in response to smoking being detected within the passenger cabin, adjust operation of a seat massager of a seat within the passenger cabin.

In further features, the control module is configured to, in response to smoking being detected within the passenger cabin, disable a WiFi transceiver configured to provide WiFi within the passenger cabin.

In further features: the vehicle includes the camera; and the control module is configured to detect smoking within the passenger cabin based on one or more objects detected in an image captured using the camera.

In further features, the control module is further configured to, in response to smoking being detected within the passenger cabin, open at least one window of the vehicle.

In further features, the control module is further configured to, in response to smoking being detected within the passenger cabin, turn on a blower of a heating ventilation and air conditioning (HVAC) system of the vehicle.

In a feature, a method includes: at least one of: measuring an amount of a chemical in air within a passenger cabin of a vehicle; and capturing images within the passenger cabin of the vehicle; detecting smoking within the passenger cabin based on the at least one of the amount of the chemical and at least one of the images; and in response to smoking being detected within the passenger cabin, adjusting operation of at least one of a luxury feature of the vehicle and a comfort feature of the vehicle.

Further areas of applicability of the present disclosure will become apparent from the detailed description, the claims and the drawings. The detailed description and specific examples are intended for purposes of illustration only and are not intended to limit the scope of the disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

The smell of smoking (e.g., cigarette, marijuana, tobacco, etc.) within a vehicle may remain within the vehicle after the smoking occurs. The smell of smoke within a vehicle may decrease a user experience during transportation using the vehicle.

The present application involves detecting smoking within the vehicle, such as using a VOC sensor, a smoke sensor, and/or a camera. When smoking is detected, a notification to stop smoking may be output (e.g., visibly and/or audibly) and one or more luxury and/or comfort features of the vehicle may be disabled or adjusted to make the user experience more uncomfortable. For example, when air conditioning is on and smoking is detected, the air conditioning may be disabled and heating may be performed to make the user experience more uncomfortable. Disabling or adjusting the luxury and/or comfort features may help encourage the smoker to stop smoking by making the vehicle less comfortable and/or luxurious. For example, disabling air conditioning of the vehicle and/or heating the vehicle on a hot day may encourage the smoker to stop smoking within the vehicle.

Figure 1:
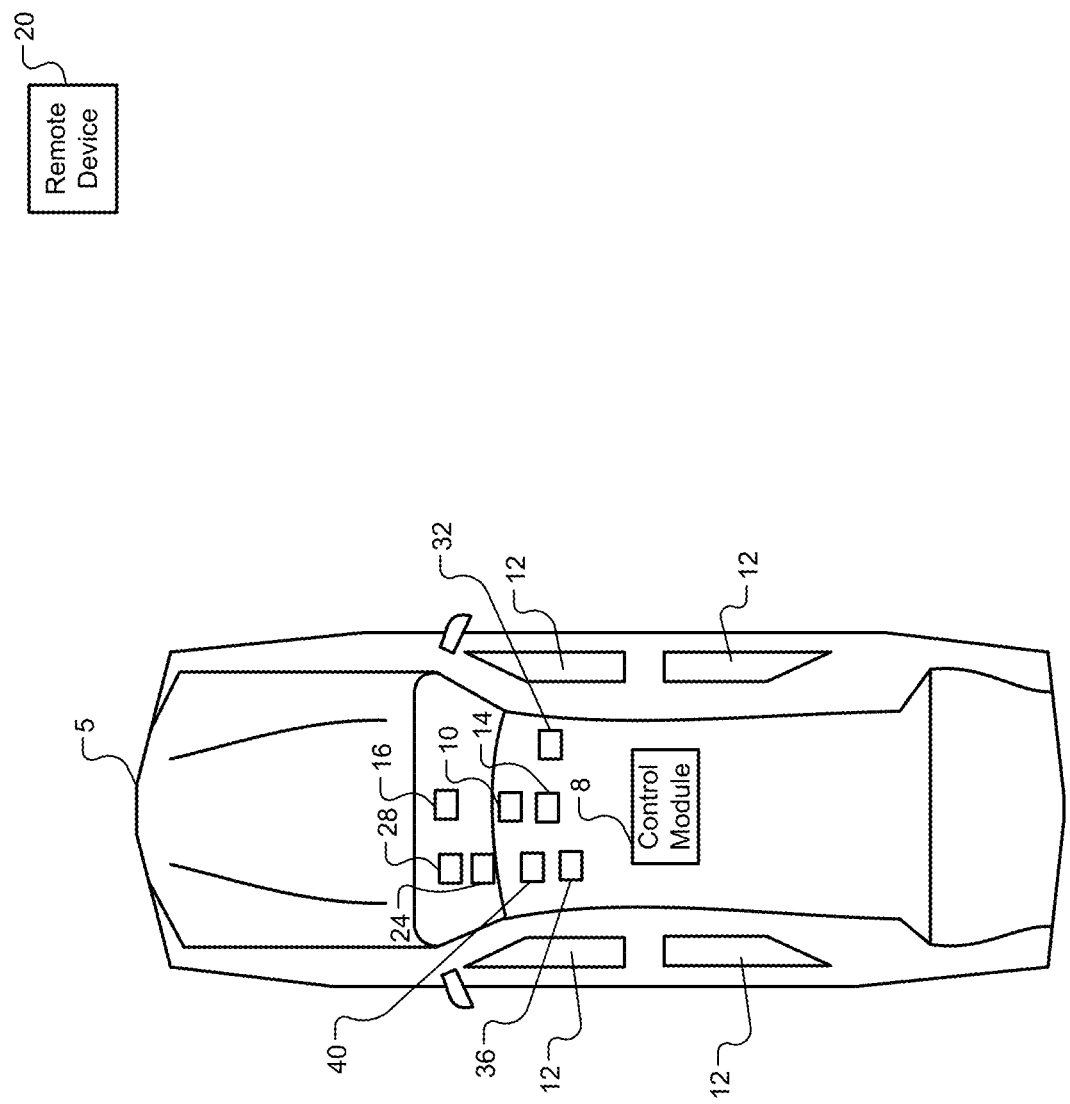
FIG. 1 is a functional block diagram of an example vehicle system.

FIG. 1 includes a functional block diagram including an example vehicle 5. The vehicle 5 includes a control module 8 and one or more olfaction sensors, such as olfaction sensor 10. Examples of olfaction sensors in vehicles include, for example, particulate matter sensors, carbon monoxide (or other carbon oxide) sensors, volatile organic compound (VOC) sensors, and other types of sensors. The vehicle 5 may include one or more different types of olfaction sensors.

The olfaction sensor(s) are each configured to measure an amount of one or more chemicals within a passenger cabin of the vehicle 5. For example, the vehicle 5 may include a particulate matter sensor configured to measure one or more amounts (e.g., concentrations or mass flow rates) of particulate of one or more different sizes in air within the passenger cabin. Additionally or alternatively, the vehicle 5 may include a carbon monoxide sensor configured to measure an amount (e.g., concentration) of carbon monoxide in air within the passenger cabin. Additionally or alternatively, the vehicle 5 may include a VOC sensor configured to measure an amount (e.g., concentration) of VOCs within the passenger cabin.

The control module 8 may receive the measurements from the olfaction sensor(s) and take one or more remedial actions based on the measurements. For example, when one or more amount of one or more chemicals (e.g., particulate, carbon monoxide, VOCs) measured by one or more olfaction sensors is/are greater than one or more respective predetermined amount/s (e.g., of particulate matter, carbon monoxide, or VOCs, respectively), the control module 8 may take one or more remedial actions. The predetermined amount/s is/are greater than zero.

For example, the control module 8 may open one or more windows 12 of the vehicle 5 when the amount of a chemical is greater than the predetermined amount. Additionally or alternatively, the control module 8 may generate an alert within the vehicle 5 when the amount of a chemical is greater than the predetermined amount.

For example, the control module 8 may generate or display a visual alert, such as via a visual indicator 14 that is visible within the passenger cabin of the vehicle 5. The visual indicator 14 may be, for example, one or more indicator lights, a display, or another suitable type of visual indicator. Additionally or alternatively, the control module 8 may output an audible alert, such as via one or more speakers. Additionally or alternatively, the control module 8 may output a tactile alert, such as via turning on one or more vibrating devices, such as located in one or more seats, in a steering wheel, or in another suitable location. Additionally or alternatively, the control module 8 may wirelessly transmit an alert to mobile devices of occupants for output by the mobile devices. The control module 8 may transmit the alert wirelessly, for example, using a Bluetooth low energy (BLE) communication protocol, a WiFi communication protocol, an ultra wideband (UWB) communication protocol, or another suitable type of wireless communication.

Additionally or alternatively, the control module 8 may turn on a heating ventilation and air conditioning (HVAC) system 16 of the vehicle 5 when the amount of a chemical is greater than the predetermined amount. The control module 8 may, for example, turn on a blower of the HVAC system 16 and control one or more actuators of the HVAC system 16 to recirculate air from within the passenger cabin to outside of the passenger cabin. This is discussed in more detail below.

Additionally or alternatively, the control module 8 may store an indicator in memory of the vehicle when the amount of a chemical is greater than the predetermined amount. The indicator may indicate that the amount of the chemical was greater than the predetermined amount. The control module 8 may also store a time stamp (e.g., including a date and a time of the occurrence) with the indicator.

Additionally or alternatively, the control module 8 may transmit an indicator to a remote device 20, such as of a fleet operator, when the amount of a chemical is greater than the predetermined amount. The control module 8 may transmit the indicator via one or more communication networks, such as a cellular communication network, a satellite communication network, a Wi-Fi communication network, or another suitable type of communication network.

The olfaction sensor 10 may be implemented within the HVAC system 16 (e.g., in a duct of the HVAC system 16) or in another location to measure air within the passenger cabin of the vehicle 5.

The vehicle 5 may also include one or more cameras, such as camera 40. The camera 40 faces one or more occupants (and seats of the vehicle 5), such as a driver and/or one or more passengers. While only the camera 40 is shown, other cameras may function and be disposed similarly or identically and have different fields of view covering different portions within the passenger cabin. For example, one camera may face each seat or row of seats.

The present application involves systems and methods to deter vehicle occupants from smoking in the vehicle by the control module 8 disabling one or more comfort and/or luxury features of the vehicle when smoking is detected. Examples of comfort and luxury features include climate control (via the HVAC system 16), heated and/or cooled seats, massaging seats, video (e.g., television) streaming via a display (e.g., the display 36) WiFi, and/or one or more other luxury and/or comfort features.

The vehicle may include a WiFi (e.g., Institute of Electrical and Electronics Engineers (IEEE) 802.11 based) transceiver 24 configured to connect to and communicate with mobile devices within the vehicle 5. The WiFi transceiver 24 may communicate with a cellular transceiver 28. The cellular transceiver 28 may communicate with other devices via one or more networks, such as the Internet.

Mobile devices (e.g., cellular phones, tablet computers, laptop computers, etc.) of occupants of the vehicle 5 may wirelessly connect to the WiFi transceiver 24 to communicate with other devices via the cellular transceiver 28 and the network(s). In other words, mobile devices of vehicle occupants may communicate with computing devices that are remote from the vehicle 5 via the WiFi transceiver 24 and the cellular transceiver 28 without any other type of connection, such as a cellular connection, satellite connection, etc.

The control module 8 detects the occurrence of smoking (e.g., tobacco, marijuana, etc.) based on one or more inputs. For example, the control module 8 may detect that smoking is occurring when an amount of a VOC within the passenger cabin is greater than a predetermined amount. The predetermined amount may be greater than zero.

Additionally or alternatively, the control module 8 may detect that smoking is occurring based on one or more images of within the passenger cabin from one or more cameras, such as the camera 40. The control module 8 may detect that smoking is occurring, for example, using an object detection algorithm, such as an object detection algorithm to detect smoking or smoking devices (e.g., cigarettes, pipes, tanks, bongs, hookahs, etc.) in images.

Additionally or alternatively, the control module 8 may detect that smoking is occurring based on a measurement from a smoke sensor 32, such as a photoelectric smoke sensor or an ionization smoke sensor. The control module 8 may determine that smoking is occurring when the measurement from the smoke sensor 32 is greater than a predetermined amount that is greater than zero.

When smoking is detected, the control module 8 may be configured to detect which (one) occupant is doing the smoking and/or the seat within the passenger cabin where the smoking is occurring. The control module 8 may detect which occupant is doing the smoking and/or the seat where the smoking is occurring based on input from one or more olfaction sensors, input from the smoke sensors (e.g., 32), one or more images, from input received from an occupant reporting a smoking event within the vehicle via a mobile device, or in another suitable manner.

When a smoking event is detected, the control module 8 disables or adjusts one or more comfort and/or luxury features of the vehicle 5. For example, the control module 8 may disable (turn off) climate control (via the HVAC system 16). Alternatively, the control module 8 may turn on air conditioning and initiate heating via the HVAC system 16 when smoking is detected.

Additionally or alternatively, the control module 8 may disable seat heating and/or cooling when smoking is detected. In various implementations, if seat cooling is being performed, the control module 8 may disable seat cooling and turn on seat heating to provide discomfort. If seat heating is being performed, the control module 8 may disable seat heating and turn on seat cooling to provide discomfort.

Additionally or alternatively, the control module 8 may disable seat massagers when smoking is detected. Alternatively, the control module 8 may adjust seat massagers to provide uncomfortable massaging (e.g., increase a rate, magnitude, or pattern of massaging) when smoking is detected.

Additionally or alternatively, the control module 8 may disable in-vehicle video streaming on one or more displays 36 within the passenger cabin when smoking is detected. Additionally or alternatively, the control module 8 may disable the WiFi transceiver 24 when smoking is detected. Additionally or alternatively, the control module 8 may disable or adjust one or more other luxury and/or comfort features when smoking is detected.

The control module 8 also outputs a notification that the feature(s) are disabled due to the smoking when smoking is detected. The notification may be visual on one or more displays 36 within the passenger cabin and/or audible via one or more speakers.

The notification may also include that the smoking occupant will have a predetermined period (e.g., 30 seconds) to stop the smoking. The notification may also indicate that the disabled luxury and/or comfort features will be re-enabled if the smoking ends (e.g., within the predetermined period). The control module 8 may enable (turn on) the disabled one or more luxury and/or comfort features when the control module 8 determines that the smoking has ended.

The control module 8 may determine that the smoking has ended, for example, when the amount of the VOC is greater than the predetermined amount. Additionally or alternatively, the control module 8 may determine that the smoking has ended based on one or more images from one or more cameras, such as the camera 40. Additionally or alternatively, the control module 8 may determine that the smoking has ended when a measurement from the smoke sensor 32 is less than the predetermined amount.

When smoking is detected, the control module 8 may disable the luxury and/or comfort features for the entire vehicle 5 or for only the specific occupant or seat where the smoking is occurring. Disabling the luxury and/or comfort features for the entire vehicle 5 may allow other vehicle occupants to pressure the occupant doing the smoking to stop smoking so that luxury and/or comfort features for the vehicle 5 are restored.

Figure 2:
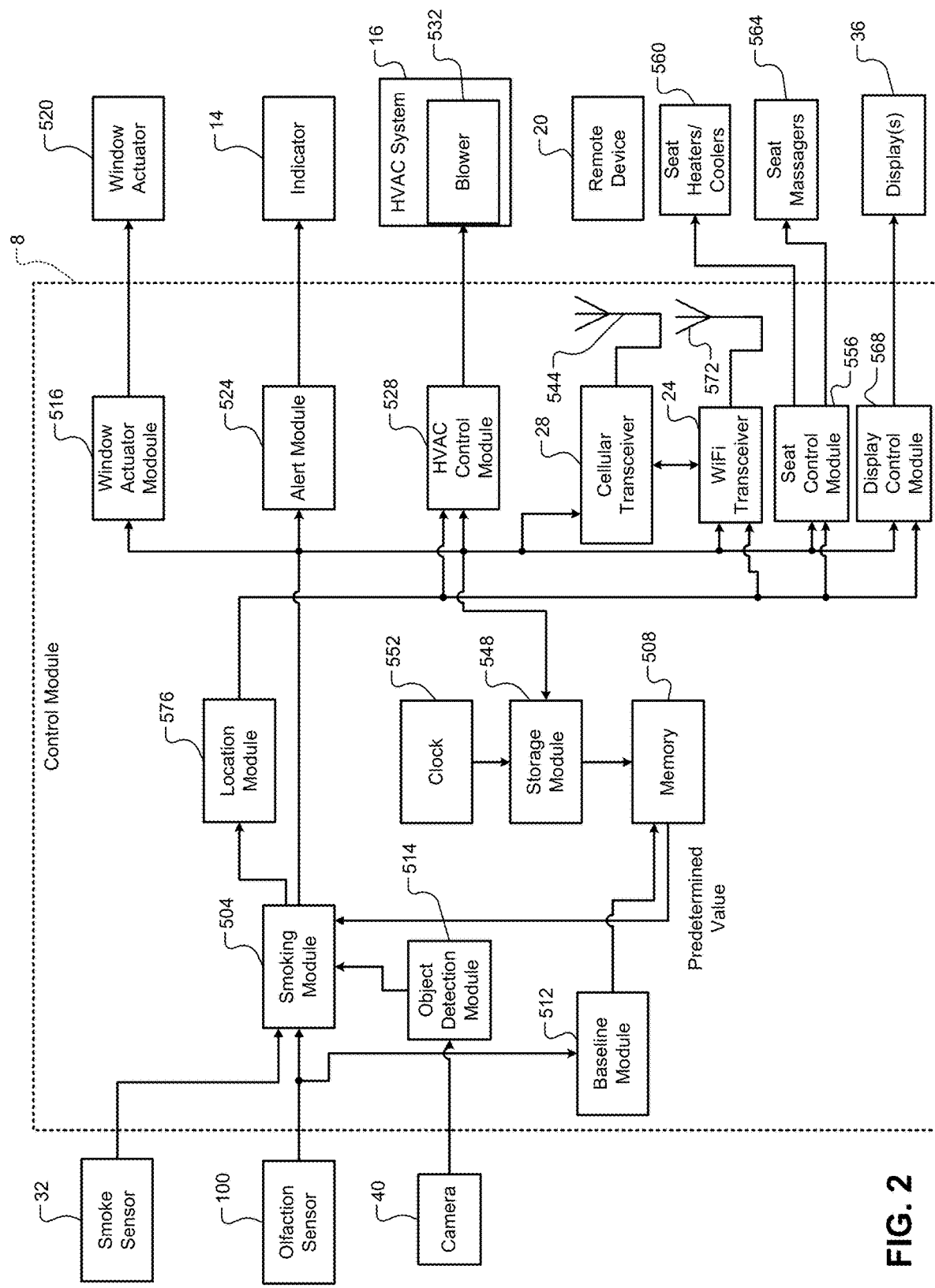
FIG. 2 is a diagram including an example control system of a vehicle.

FIG. 2 is a functional block diagram of an example implementation of a control system. As discussed above, one or more olfaction sensors may be included, such as at least one of a VOC sensor, a particulate matter sensor, and a carbon monoxide sensor. The olfaction sensor 100 of FIG. 3 may be a VOC sensor, a particulate matter sensor, or a carbon monoxide sensor. In various implementations, the olfaction sensor 100 may include two or more of a VOC sensor, a particulate matter sensor, and a carbon monoxide sensor.

A smoking module 504 determines whether smoking is occurring within the passenger cabin based on measurements from the olfaction sensor 100. For example, the smoking module 504 may compare a measurement from the olfaction sensor 100 with a predetermined value and, based on the comparison, generate an output signal based on the comparison. The measurement may be, for example, an amount of particulate, an amount of VOCs, or an amount of carbon monoxide. The smoking module 504 may set the output signal to the first state to indicate that smoking is not occurring when the measurement is less than the predetermined value and set the output signal to a second state and indicate that smoking is occurring when the measurement is greater than or equal to the predetermined value.

The smoking module 504 may obtain the predetermined value from memory 508. The predetermined value is greater than zero and may be a fixed predetermined value. Alternatively, the predetermined value may be variable. For example, a baseline module 512 may determine a baseline value and set the predetermined value to the baseline value. The baseline module 512 may set the baseline value, for example, based or equal to an average of the measurements from the olfaction sensor 100 taken over a predetermined period, such as a week or a month. An average may be determined by summing the measurements and dividing by the number of measurements summed.

The smoking module 504 may additionally or alternatively detect smoking based on images from the camera. For example, an object detection module 514 may detect and indicate objects captured in images using an object detection algorithm. For example, the object detection module 514 may be configured to detect and indicate the presence of cigarettes, smoking accessories (e.g., lighters, pipes, etc.), and other types of smoking instruments. The smoking module 504 may set the output signal to the first state to indicate that smoking is not occurring when no objects indicative of smoking are detected and set the output signal to a second state and indicate that smoking is occurring when one or more objects indicative of smoking are detected.

The smoking module 504 may additionally or alternatively detect smoking based on measurements from the smoke sensor 32. For example, the smoking module 504 may compare a measurement from the smoke sensor 32 with a predetermined value and, based on the comparison, generate an output signal based on the comparison. The smoking module 504 may set the output signal to the first state to indicate that smoking is not occurring when the measurement is less than the predetermined value and set the output signal to a second state and indicate that smoking is occurring when the measurement is greater than or equal to the predetermined value. The predetermined value may be fixed or variable like the predetermined value discussed above.

One or more remedial actions may be taken when the smoking module 504 indicates that smoking is detected (e.g., when the output signal of the smoking module 504 is in the second state). For example, a window actuator module 516 controls actuation (opening and closing) of one or more window actuators, such as window actuator 520, of the vehicle. The window actuator 520 opens (e.g., lowers) and closes (e.g., raises) a window of the vehicle. The window actuator module 516 may control one or more window actuators to open one, more than one, or all of the windows of the vehicle when the smoking module 504 indicates that smoking is detected. Opening the window(s) may include, for example, opening the window(s) to a partially open position further than the window(s) is/are presently open or opening the window(s) to a fully open position.

Additionally or alternatively, an alert module 524 may generate an alert (e.g., visually the visual indicator 14, audibly via one or more speakers, and/or haptically via one or more vibrating devices) when the smoking module 504 indicates that smoking is detected.

Additionally or alternatively, a HVAC control module 528 may turn on a blower 532 of the HVAC system 16 when the output signal of the smoking module 504 indicates that smoking is detected.

Additionally or alternatively, the cellular transceiver 28 may wirelessly transmit an indicator to the remote device 20 via one or more antennas 544 when the smoking module 504 indicates that smoking is detected. Additionally or alternatively, a storage module 548 may store an indicator in the memory 508 when the output signal of the smoking module 504 indicates that smoking is detected. The indicator may indicate that smoking was detected. The storage module 548 may also store a time stamp (e.g., including a date and a time of the occurrence) with the indicator. A clock 552 may track the date and time.

Additionally or alternatively, the control module 8 may disable or adjust one or more comfort and/or luxury features of the vehicle when smoking is detected, such as discussed above. Examples of comfort and luxury features include climate control (via the HVAC system 16), heated and/or cooled seats, massaging seats, video (e.g., television) streaming via a display (e.g., the display(s) 36), WiFi, and/or one or more other luxury and/or comfort features.

In addition to or as an alternative to the above, the HVAC control module 528 may disable (turn off) or adjust climate control (via the HVAC system 16) when smoking is detected. For example, if air conditioning is being performed, the HVAC control module 528 may disable air conditioning and start heating and/or increase a temperature setpoint for the HVAC system 16 when smoking is detected. In various implementations, the HVAC control module 528 may increase operation of the HVAC system 16 to increase heating or increase cooling when smoking is detected. For example, when heating is being performed, the HVAC control module 528 may operate the HVAC system 16 to increase heating when smoking is detected. When cooling is being performed, the HVAC control module 528 may operate the HVAC system 16 to increase cooling (and decrease temperature) when smoking is detected.

Additionally or alternatively, a seat control module 556 may disable or adjust all seat heaters and/or coolers 560 of seats of the vehicle when smoking is detected. Seat heaters warm cushions and/or backs of seats when enabled and powered. Seat coolers cool cushions and/or backs of the seats when enabled and powered. The seat control module 556 may disable the seat heaters and/or coolers 560 to prevent the seat heaters and/or coolers 560 from providing heating and/or cooling of the seats. The seat control module 556 may begin opposite operation of the seat heaters and/or coolers 560 to provide discomfort. For example, if seat cooling is being performed, seat heating may be initiated. If seat heating is being performed, seat cooling may be initiated. In various implementations, the seat control module 556 may increase operation of the seat heaters and/or coolers 560 to increase heating or increase cooling when smoking is detected. Disabling or adjusting all heating and/or cooling of seats may pressure a smoker to stop smoking.

Additionally or alternatively, the seat control module 556 may disable or adjust all seat massagers 564 when smoking is detected. Seat massagers provide massaging of cushions and/or backs of the seats when enabled and powered. The seat control module 556 may disable the seat massagers 564 to prevent the seat massagers 564 from providing massaging. The seat control module 556 may adjust the seat massagers 564 to provide discomfort or less comfort, such as by adjusting a massage rate, magnitude, and/or pattern. Disabling or adjusting all seat massagers 564 may pressure a smoker to stop smoking.

Additionally or alternatively, a display control module 568 may disable in-vehicle video streaming on one, more than one, or all of the displays 36 within the passenger cabin when smoking is detected. Video may be streamed from remote sources via the cellular transceiver 28. The display control module 568 may disable (e.g., pause) video receipt via the cellular transceiver 28 when smoking is detected, for example, to minimize energy consumption. In various implementations, the display control module 568 may simply disable the displays 36 when smoking is detected. The display control module 568 may, however, continue storing streamed video. This may enable better video playback, for example, if the detected smoking ends.

Additionally or alternatively, the WiFi transceiver 24 may disable WiFi connections with (e.g., disconnect from) all mobile devices when smoking is detected. The WiFi transceiver 24 may be configured to communicate with mobile devices via one or more antennas, such as antenna 572, when WiFi connections are enabled.

One or more modules (e.g., the alert module 524, the display control module 568, etc.) may output a notification that the luxury and/or comfort feature(s) are disabled due to the smoking when smoking is detected. The notification may be visual on one or more displays 36 within the passenger cabin and/or audible via one or more speakers. A speaker control module may control audio output via the speaker(s).

The notification may also include that the smoking occupant will have a predetermined period (e.g., 30 seconds) to stop the detected smoking. The notification may also indicate that the disabled or adjusted luxury and/or comfort features will be re-enabled (or normal control may resume) if the smoking ends (e.g., within the predetermined period). The control module 8 may resume normal operation of the one or more luxury and/or comfort features when the smoking module 504 determines and indicates that the smoking has ended (e.g., the output signal is in the first state).

The smoking module 504 may determine that the smoking has ended, for example, when the amount of the VOC is greater than the predetermined amount. Additionally or alternatively, the smoking module 504 may determine that the smoking has ended when the object detection module 514 does not detect any smoking devices, such as cigarettes, pipes, hookahs, etc. Additionally or alternatively, the smoking module 504 may determine that the smoking has ended when a measurement from the smoke sensor 32 is less than the predetermined value. Resuming normal control of the comfort and/or luxury features allows the previously disabled or adjusted features to be used by vehicle occupants.

When smoking is detected, the respective modules may disable or adjust luxury and/or comfort features for the entire vehicle 5 or for only the specific occupant or seat where the smoking is detected. Disabling or adjusting the luxury and/or comfort features for the entire vehicle 5 may allow other vehicle occupants to pressure the occupant doing the smoking to stop smoking so that luxury and/or comfort features for the vehicle 5 are restored. Disabling or adjusting the luxury and/or comfort features for a specific seat of a smoker may make transportation less pleasurable for the smoker.

When smoking is detected, a location module 576 may be configured to detect which (one) occupant is doing the smoking and/or the seat within the passenger cabin where the smoking is occurring. For example, the location module 576 may identify the seat where smoking is occurring by locating the seat within one or more images from the camera 40. As another example, olfaction sensors may be located in various locations near seats (e.g., one olfaction sensor per seat). The location module 576 may identify the seat where smoking is occurring, for example, as a seat where a highest concentration of one or more chemicals (e.g., VOCs) is measured by the associated olfaction sensor. As another example, smoke sensors 32 may be located in various locations near seats (e.g., one smoke sensor per seat). The location module 576 may identify the seat where smoking is occurring, for example, as a seat where a highest measurement by the associated smoke sensor is measured by the associated smoke sensor. The respective control modules may then disable the luxury and/or comfort features of only the seat(s) where smoking is detected. The respective control modules may maintain enabled the luxury and/or comfort features of seats where smoking is not detected.

Figure 3:
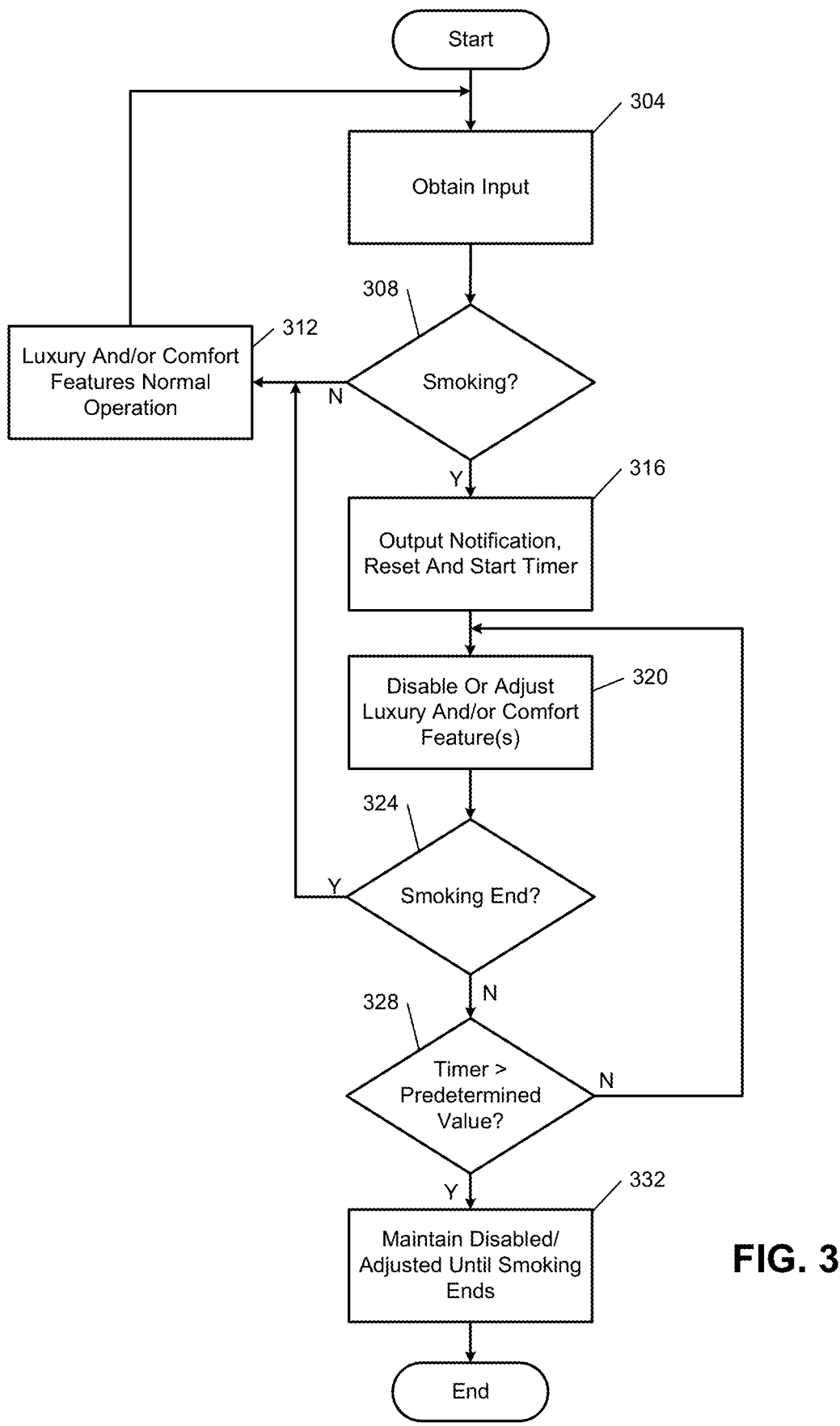
FIG. 3 is a flowchart depicting an example method of controlling luxury and/or comfort features based on smoking.

FIG. 3 is a flowchart depicting an example method of controlling luxury and/or comfort features based on smoking. Control begins with 304 where the control module 8 receives input regarding smoking, such as from the olfaction sensor 100, the smoke sensor 32, and/or the camera 40.

At 308, the smoking module 504 determines whether the input is indicative of smoking. For example, the smoking module 504 may determine whether the measurement from the smoke sensor 32 is greater than a predetermined value, whether the measurement from the olfaction sensor 100 (e.g., amount of VOCs) is greater than a predetermined value, and/or determine whether one or more smoking devices are present in an image. If 308 is true, control continues with 316. If 308 is false, the respective modules maintain normal control of the associated luxury and/or comfort features of the vehicle at 312, and control returns to 304. Normal control allows the luxury and/or comfort features to be used as desired by occupants.

At 316, the control module 8 outputs the notification to stop smoking. For example, display control module 568 may visually output the notification via one or more of the displays 36. Additionally or alternatively, the speaker control module may audibly output the notification via one or more speakers. The smoking module 504 may also reset a timer (e.g., to zero) and start the timer at 316.

At 320, one or more modules disable or adjust their associated luxury and/or comfort features. The disabled or adjusted features may be disabled or adjusted for all seats or the one or more seats where smoking is detected. For example, the HVAC control module 528 may disable the HVAC system 16 (e.g., heating and cooling), the seat control module 556 may disable the seat heaters and/or seat coolers 560, the seat control module 556 may disable the seat massagers 564, the WiFi transceiver 24 may disable streaming video, and/or the display control module 568 may disable video display on the displays 36. Alternatively, the HVAC control module 528 may warm the passenger cabin or turn on heating if cooling was being performed when smoking was detected, the seat control module 556 may provide the opposite one of seat heating and cooling, and/or the seat control module 556 may adjust seat massaging. One or more other actions may also be taken at 320, such as the window actuator module 516 may open one or more windows, and the HVAC control module 528 may turn on the blower 532 (without providing heating or cooling).

At 324, the smoking module 504 determines whether the detected smoking has ended. For example, the smoking module 504 may determine whether the measurement of the olfaction sensor 100 (e.g., the amount of VOCs) has decreased to less than the predetermined value, the measurement of the smoke sensor 32 has decreased to less than the predetermined value, and/or an image from the camera does not include any smoking devices. If 324 is true, control may return to 312 and resume normal control of all previously disabled or adjusted luxury and/or comfort features of the vehicle. If 324 is false, control may continue with 328.

At 328, the smoking module 504 may determine whether the timer is greater than a predetermined value (e.g., corresponding to a predetermined period passing after the resetting). If 328 is true, the smoking module 504 may maintain indicating smoking is detected (e.g., until all occupants have left the vehicle or until the detected smoking ends) at 332. The luxury and/or comfort features may therefore remain disabled or adjusted. If 328 is false, control may return to 320.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

In this application, including the definitions below, the terms "module" and "system" may refer to, be part of, or include circuits or circuitry that may include processor hardware (shared, dedicated, or group) that executes code and memory hardware (shared, dedicated, or group) that stores code executed by the processor hardware. The code is configured to provide the features of the modules and systems described herein. In addition, in this application the terms "module" and "system" may be replaced with the term "circuit." The term "memory hardware" may be a subset of the term computer-readable medium. The term computer-readable medium does not encompass transitory electrical and electromagnetic signals propagating through a medium, and may therefore be considered tangible and non-transitory. Non-limiting examples of a non-transitory tangible computer readable medium include nonvolatile memory, volatile memory, magnetic storage, and optical storage.

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as JavaScript Object Notation (JSON), hypertext markup language (HTML) or extensible markup language (XML); (ii) assembly code; (iii) object code generated from source code by a compiler; (iv) source code for execution by an interpreter; (v) source code for compilation and execution by a just-in-time compiler, etc. As examples only, source code may be written using syntax from languages including C, C++, C#, Objective C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A vehicle system, comprising:
   a sensor configured to measure an amount of a chemical in air within a passenger cabin of a vehicle;
   a camera configured to capture images within the passenger cabin of the vehicle;
   an object detection module configured to detect one of a lighter, a smoking pipe, a smoking tank, a smoking bong, and a hookah in at least one of one of the images using an object detection algorithm; and
   a control module configured to:
      detect smoking within the passenger cabin in response to the amount of the chemical being greater than a predetermined value and the object detection module detecting the at least one of the lighter, smoking pipe, smoking tank, smoking bong, and hookah in the at least one of the images; and
      in response to smoking being detected within the passenger cabin, output a notification to stop smoking and, after outputting the notification, adjust operation of at least one of a luxury feature of the vehicle and a comfort feature of the vehicle,
   wherein the control module is configured to, after outputting the notification in response to smoking being detected within the passenger cabin, adjust operation of a seat massager of a seat within the passenger cabin including increasing at least one of a rate, magnitude, and pattern of the seat massager thereby increasing discomfort of the massaging.

2. The vehicle system of claim 1 wherein:
   the sensor is configured to measure an amount of volatile organic compounds (VOCs) in the air within the passenger cabin; and
   the control module is configured to detect smoking within the passenger cabin when the amount of the VOCs is greater than the predetermined value.

3. The vehicle system of claim 1 wherein:
   the sensor is a smoke sensor configured to measure an amount of smoke in the air within the passenger cabin; and
   the control module is configured to detect smoking within the passenger cabin when the amount of the smoke is greater than the predetermined value.

4. The vehicle system of claim 3 wherein the smoke sensor is a photoelectric smoke sensor.

5. The vehicle system of claim 3 wherein the smoke sensor is an ionization smoke sensor.

6. The vehicle system of claim 1 wherein the control module is configured to, in response to smoking being detected within the passenger cabin, disable heating and cooling of the passenger cabin by a heating ventilation and air conditioning (HVAC) system of the vehicle.

7. The vehicle system of claim 1 wherein the control module is configured to, in response to smoking being detected within the passenger cabin while cooling of the passenger cabin is being provided by a heating ventilation and air conditioning (HVAC) system of the vehicle, adjust operation of the HVAC system and warm the passenger cabin.

8. The vehicle system of claim 1 wherein the control module is configured to, in response to smoking being detected within the passenger cabin, disable a seat heater configured to heat a seat within the passenger cabin.

9. The vehicle system of claim 1 wherein the control module is configured to, in response to smoking being detected within the passenger cabin while a seat heater configured to heat a seat within the passenger cabin is on, disable the seat heater and turn on a seat cooler configured to cool the seat.

10. The vehicle system of claim 1 wherein the control module is configured to, in response to smoking being detected within the passenger cabin while a seat heater configured to heat a seat within the passenger cabin is on, adjust operation of the seat heater and increase heating of the seat.

11. The vehicle system of claim 1 wherein the control module is configured to, in response to smoking being detected within the passenger cabin, disable a seat cooler configured to cool a seat within the passenger cabin.

12. The vehicle system of claim 1 wherein the control module is configured to, in response to smoking being detected within the passenger cabin while a seat cooler configured to cool a seat within the passenger cabin is on, disable the seat cooler and turn on a seat heater configured to heat the seat.

13. The vehicle system of claim 1 wherein the control module is configured to, in response to smoking being detected within the passenger cabin while a seat cooler configured to cool a seat within the passenger cabin is on, adjust operation of the seat cooler and increase cooling of the seat.

14. The vehicle system of claim 1 wherein the control module is configured to, in response to smoking being detected within the passenger cabin, disable a WiFi transceiver configured to provide WiFi within the passenger cabin.

15. The vehicle system of claim 1 wherein the control module is further configured to, in response to smoking being detected within the passenger cabin, open at least one window of the vehicle.

16. The vehicle system of claim 1 wherein the control module is further configured to, in response to smoking being detected within the passenger cabin, turn on a blower of a heating ventilation and air conditioning (HVAC) system of the vehicle.

17. A method, comprising:
   measuring an amount of a chemical in air within a passenger cabin of a vehicle;
   capturing images within the passenger cabin of the vehicle;
   detecting at least one of a lighter, a smoking pipe, a smoking tank, a smoking bong, and a hookah in at least one of one of the images using an object detection algorithm;
   detecting smoking within the passenger cabin in response to the amount of the chemical being greater than a predetermined value and detecting the at least one of the lighter, smoking pipe, smoking tank, smoking bong, and hookah in the at least one of the images; and in response to smoking being detected within the passenger cabin, outputting a notification to stop smoking and, after outputting the notification, adjusting operation of at least one of a luxury feature of the vehicle and a comfort feature of the vehicle, wherein the adjusting includes, in response to smoking being detected within the passenger cabin, after outputting the notification, adjusting operation of a seat massager of a seat within the passenger cabin including increasing at least one of a rate, magnitude, and pattern of the seat massager thereby increasing discomfort of the massaging.

* * * * *

UNITED STATES PATENT AND TRADEMARK OFFICE
CERTIFICATE OF CORRECTION

PATENT NO. : 12,377,711 B2
APPLICATION NO. : 17/369130
DATED : August 5, 2025
INVENTOR(S) : Sibu Varughese et al.

Page 1 of 1

It is certified that error appears in the above-identified patent and that said Letters Patent is hereby corrected as shown below:

In the Claims

Column 13, Line 27: Claim 1, delete "one of one of" and insert --one of-- therefor
Column 14, Line 64: Claim 17, delete "one of one of" and insert --one of-- therefor Signed and Sealed this
Twenty-third Day of December, 2025

John A. Squires
*Director of the United States Patent and Trademark Office*